(12) United States Patent
Rout et al.

(10) Patent No.: US 11,447,891 B2
(45) Date of Patent: Sep. 20, 2022

(54) COMPOSITIONS AND METHODS FOR RAPID PRODUCTION OF VERSATILE NANOBODY REPERTOIRES

(71) Applicant: The Rockefeller University, New York, NY (US)

(72) Inventors: Michael P. Rout, New York, NY (US); Brian T. Chait, New York, NY (US)

(73) Assignee: The Rockefeller University, New York, NY (US)

( * ) Notice: Subject to any disclaimer, the term of this patent is extended or adjusted under 35 U.S.C. 154(b) by 395 days.

(21) Appl. No.: 16/539,308

(22) Filed: Aug. 13, 2019

(65) Prior Publication Data

US 2019/0391159 A1    Dec. 26, 2019

Related U.S. Application Data

(63) Continuation of application No. 15/320,811, filed as application No. PCT/US2015/037678 on Jun. 25, 2015, now abandoned.

(60) Provisional application No. 62/017,087, filed on Jun. 25, 2014.

(51) Int. Cl.

| C40B 30/04 | (2006.01) |
|---|---|
| G16B 30/00 | (2019.01) |
| C07K 16/44 | (2006.01) |
| G01N 33/68 | (2006.01) |
| C07K 16/00 | (2006.01) |
| C12Q 1/6876 | (2018.01) |

(52) U.S. Cl.
CPC .............. *C40B 30/04* (2013.01); *C07K 16/00* (2013.01); *C07K 16/44* (2013.01); *C12Q 1/6876* (2013.01); *G01N 33/6857* (2013.01); *G16B 30/00* (2019.02); *C07K 2317/22* (2013.01); *C07K 2317/569* (2013.01); *C07K 2317/92* (2013.01)

(58) Field of Classification Search
None
See application file for complete search history.

(56) References Cited

U.S. PATENT DOCUMENTS

2011/0293606 A1* 12/2011 Lejeune .................. A61P 43/00
424/133.1

\* cited by examiner

*Primary Examiner* — Christian C Boesen
(74) *Attorney, Agent, or Firm* — Hodgson Russ LLP

(57) ABSTRACT

Provided are compositions and methods for producing large repertoires of recombinant nanobodies with high affinities and specificities against any antigen. Included are methods for making and identifying nanobodies produced by camelids, the nanobodies themselves, modifications of the nanobodies, expression vectors encoding the nanobodies, cDNAs encoding the nanobodies, cells comprising the expression vectors and/or cDNA, and methods of making the nanobodies recombinantly. Antigen-specific nanobodies and antigen binding fragments thereof having a Kd for the antigen in a sub-micromolar range are provided.

2 Claims, 28 Drawing Sheets

Specification includes a Sequence Listing.

LaG-2

MAQVQLVESGGGLVQAGGSLRLSCAASGRTFSNYAMGWFRQAPGKEREFVAAISWTGVSTYYADS
VKGRFTISRDNDKNTVYVQMNSLIPEDTAIYYCAAVRARSFSDTYSRVNEYDYWGQTQVTV

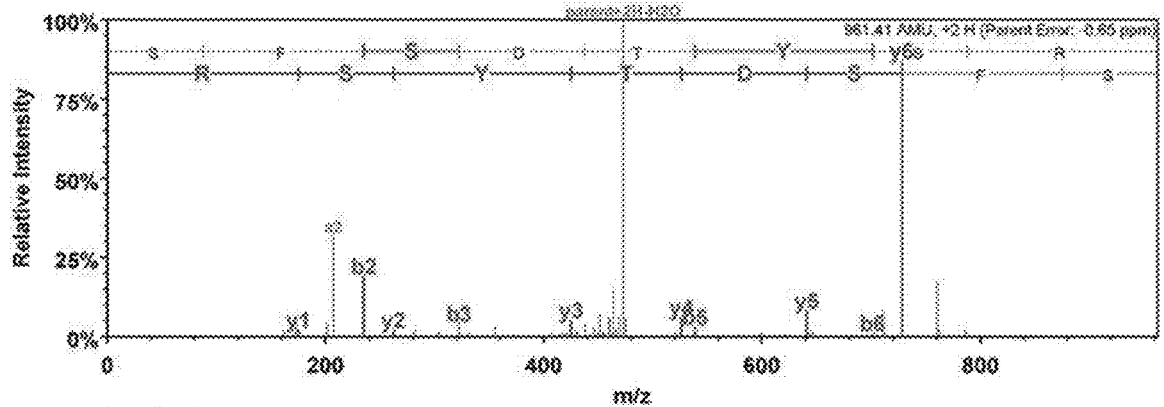

LaG-3

MAQVQLVESGGGLVQAGGSLRVSCAASGRTYSDYAMGWFRQAPGKERDFVAGISGSGGDTYYADS
VKGRFTISRDNAKNTMYLQMNSLKPEDTAVYFCAARTGTVLFTSRVDYRYWGQGTQVTV

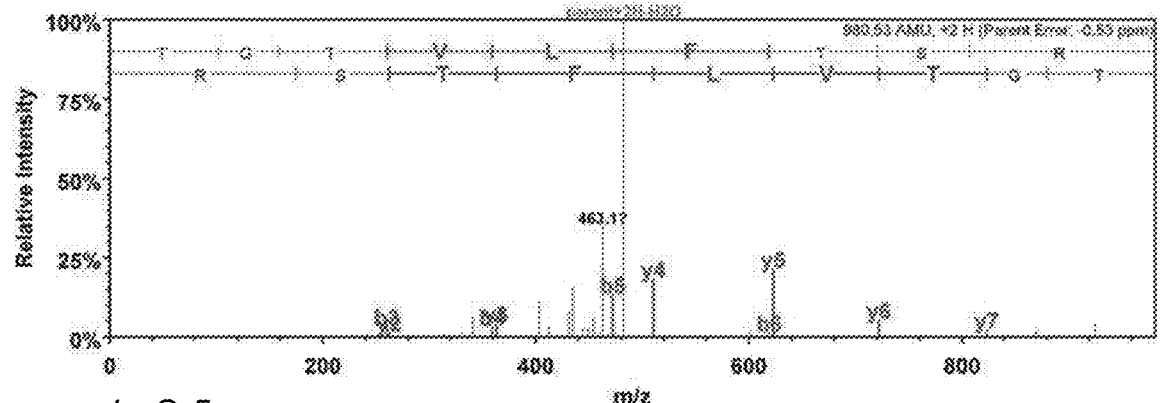

LaG-5

QVQLVESGGGLVQAGGSLRLSCAASGSIFSSNAMAWYRQTPEKQRELICDITRGGITKCADSVKGRF
TISRDNTKNTVYLQMNSLKSEDTAVYYCAAKSEGYFGFPRVENEYPYWGQGTQVTV

LaG-6

MAQVQLVESGGGLVQAGGSLRLSCAASGRTFSTSAMAWFRQAPGKEREFAAGITWISSSTYYTDSV
KGRFTISRDNAKNTVYLQMNSLKPEDTAVYYCAAKSEGYFGFPRVENEYPYWGQGTQVTV

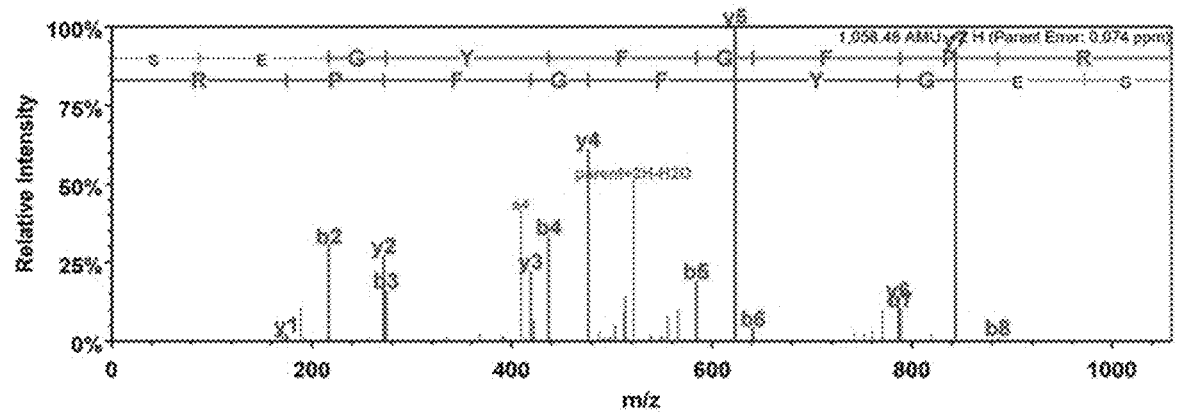

Figure 9

LaG-10

MAQVQLVESGGGLVQAGDSLQLSCAFSGGTFSTYAMGWFRQAPGKER<u>EFVGGISRSGATTNYED SVK</u>GRFTISKDNTKNTVYLQLNSLKPEDTAVYYCAAR<u>NNILPVTTIDK</u>YEYWGQGTQVTV

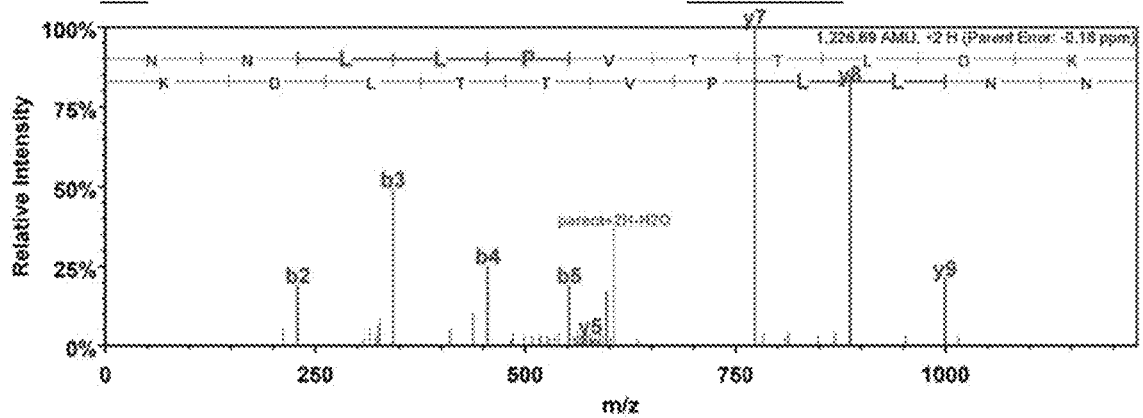

LaG-11

MADVQLVESGGRSVRAGDSLRLSCLASGGTFSLYAMGWFRQAPGKEREFVAAVTWSGGSTYYTDS VKGRF SISRDNAK<u>NTVYLQMNSLK</u>PEDTAVYYCAVR<u>TSGFFGSIPVTER</u>AFDYWGQGTQVTVS

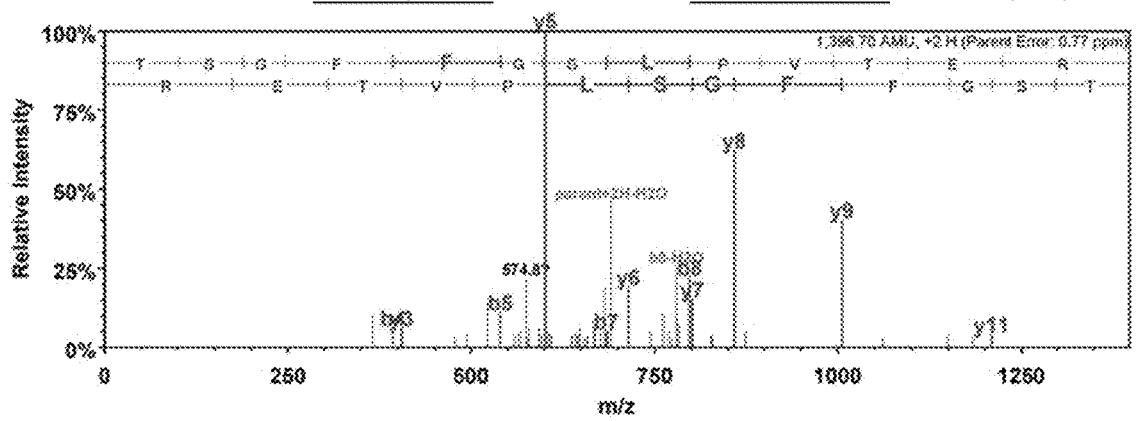

LaG-12

MASGAAGGGLGEGLVQAGGSL<u>RLSCAASGR</u>TFNSYPMAWFRQAPGKEREFVAALGWSGGSTDYA DSVKGRFTISRDNSK<u>NTVYLEMNSLK</u>PDDTGVYYCALRRR<u>GGVYNTYSGEK</u>DYDYWGQGTQVTVS

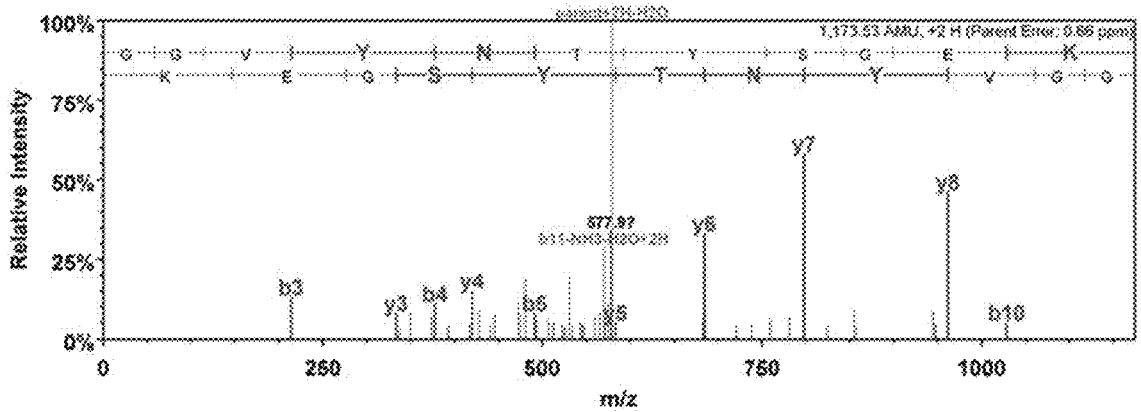

Figure 9 (continued)

LaG-14

MAQVQLVESGGGLVQAGGSLRLSCAASGRTYSISAMGWFRQAPGKEREFVAGISRSGGTTYYAD
PVKGRFTISRDNAKNTVYLQMNSLKPEDTAVYYCAARARGWTTFPAREIEYDYWGQGTQVTV

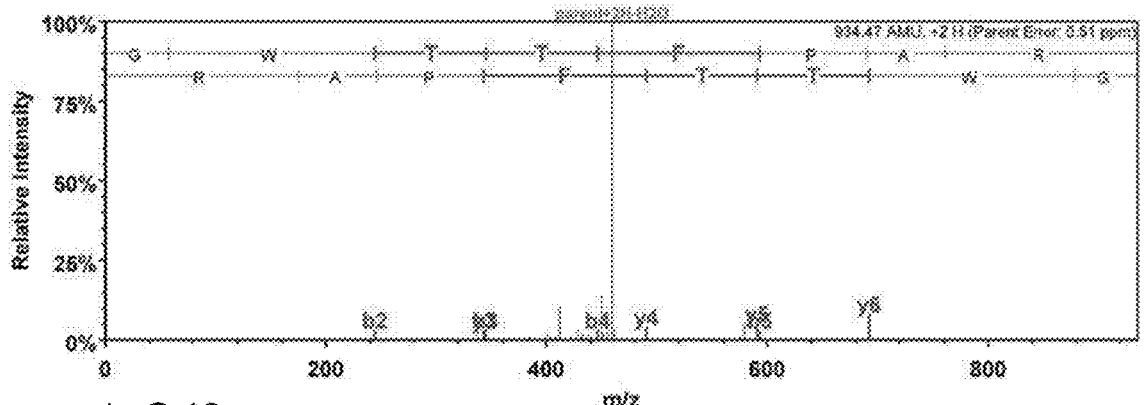

LaG-16

MAQVQLVESGGRLVQAGDSLRLSCAASGRTFSTSAMAWFRQAPGREREFVAAITWTVGNTILGDSV
KGRFTISRDRAKNTVDLQMDNLEPEDTAVYYCSARSRGYVLSVLRSVDSYDYWGQGTQVTVS

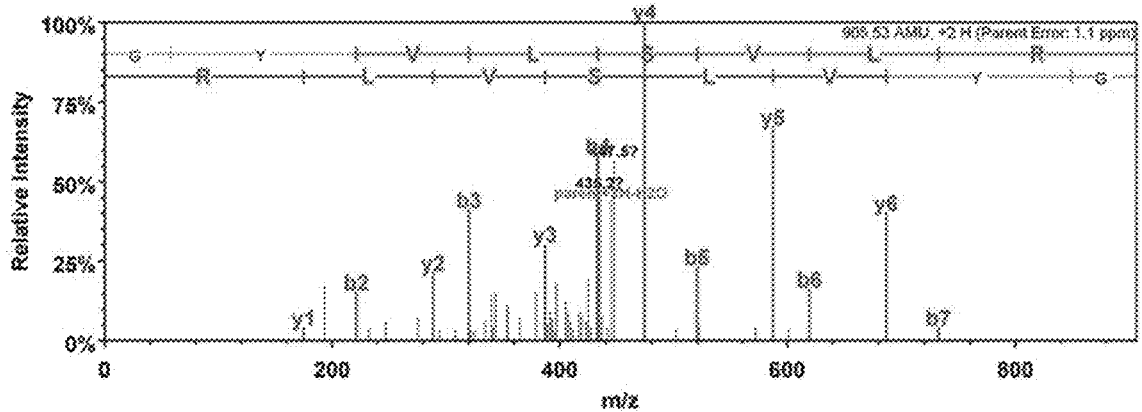

LaG-17

MADVQLVESGGGLVQAGGSLRLSCAASGRTISMAAMSWFRQAPGKEREFVAGISRSAGSAVHADSV
KGRFTISRDNTKNTLYLQMNSLKAEDTAVYYCAVRTSGFFGSIPRTGTAFDYWGQGTQVTVS

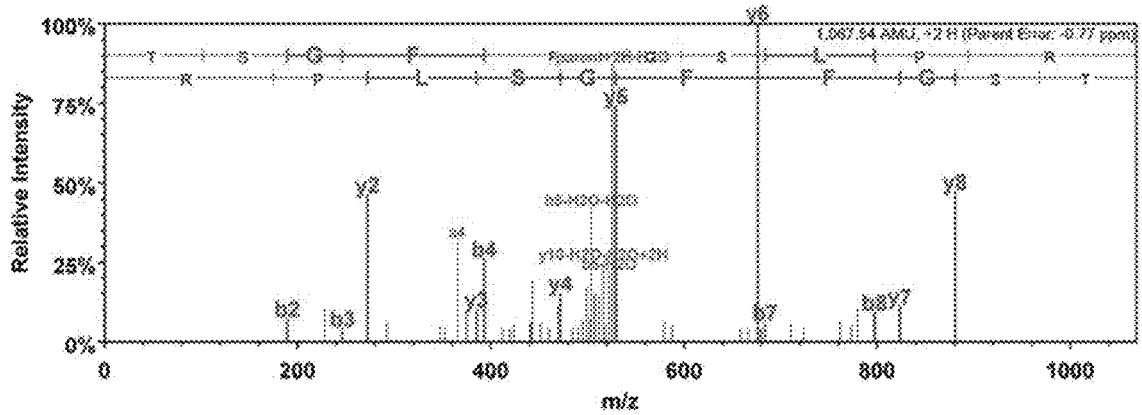

Figure 9 (continued)

LaG-18
MAQVQLVESGGGLVQTGGSLKLSCTASVRTLSYYHVGWFRQAPGKEREFVAGIHRSGESTFYADSV
KGRFTISRDNAKNTVHLQMNSLKPEDTAVYYCAQRVRGFFGPLRSTPSWYDYWGQGTQVTVS

LaG-43
MADVQLVESGGGLVQPGGSLRLSCEASGGAFSTVAMGWFRQAPGKEREFVGAITWTAGSTYYADS
AKGRFTISRDNAKNTVHLQMNSLKPEDTAVYYCAQRVRGFFGPLRTTPSWYEYWGQGTQVTVS

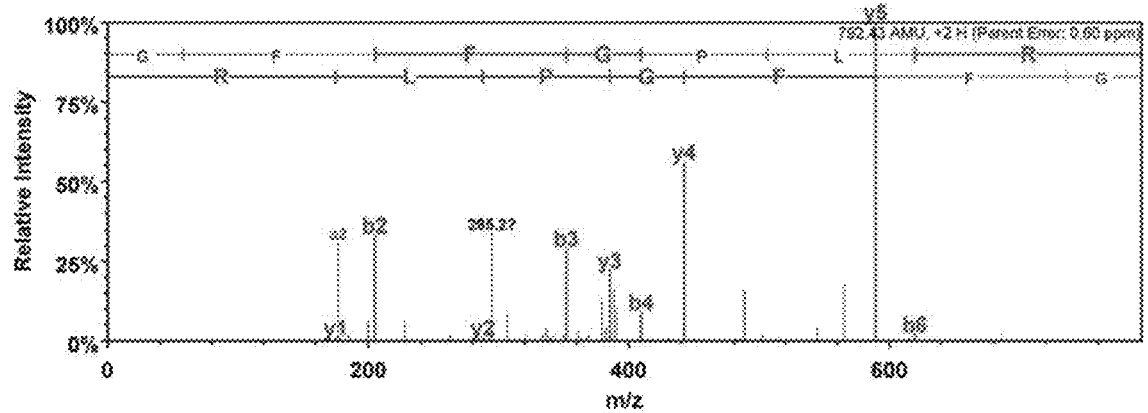

LaG-19
MAQVQLVESGGGLVQAGGSLRLSCAASGPTGAMAWFRQAPGKEREFVGGISRSGTDTYYVDSVK
G RFTIDRDNAKNTVYLQMNSLKPEDTAVYYCAARRSQILFTSRTDYEFWGQGTQVTV

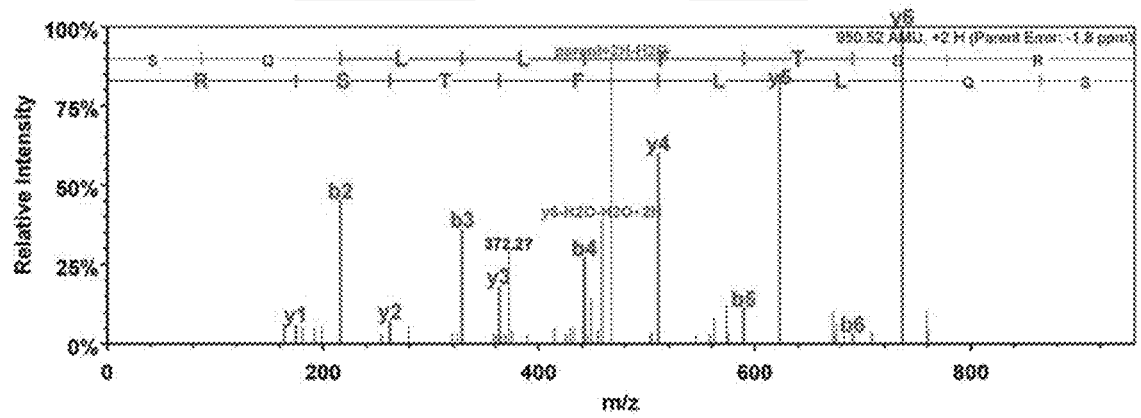

Figure 9 (continued)

LaG-21
MAQVQLVESGGGLVQAGGSLRLSCAASGPTGAMAWFRQAPGMEREFVGGISGSETDTYYADFVK
GRLTVDRDNVKNTVDLQMNSLKPEDTAVYYCAARRRVTLFTSRADYDFWGQGTQVTVS

LaG-42
MADVQLVESGGGLVQAGDSLRLSCAASGPTGAMAWFHQGLGKEREFVGGISPSGDNIYYADSVK
GRFTIDRDNAKNTVSLQMNSLKPEDMGVYYCAARRRVTLFTSRTDYEFWGRGTQVTVS

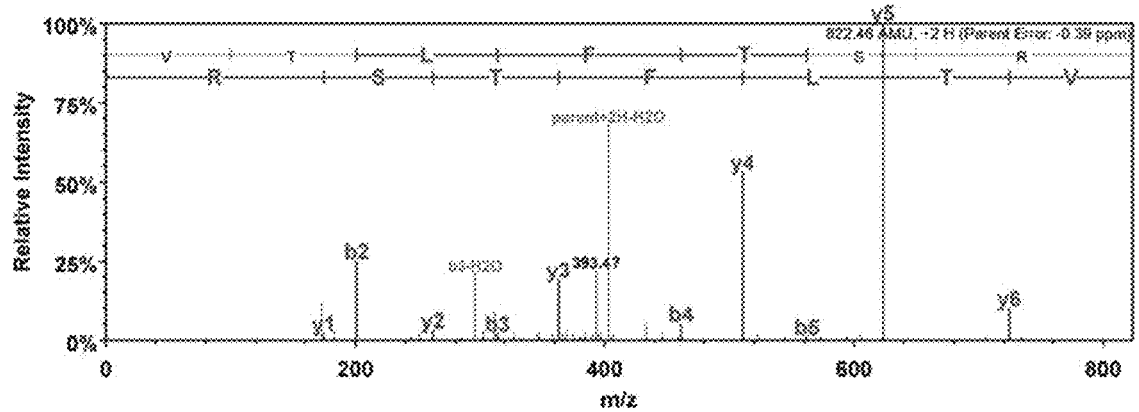

LaG-24
MADVQLVESGGGLVQPGGSLRLSCAASGEIASIIAIGWYRQAPGKQRESVALITRSGMITYGDSAQGR
FTISRDDAKNTVYLHMDDLVPEDTAVYYCNAKKVSFGDYWGQGTQVTVS

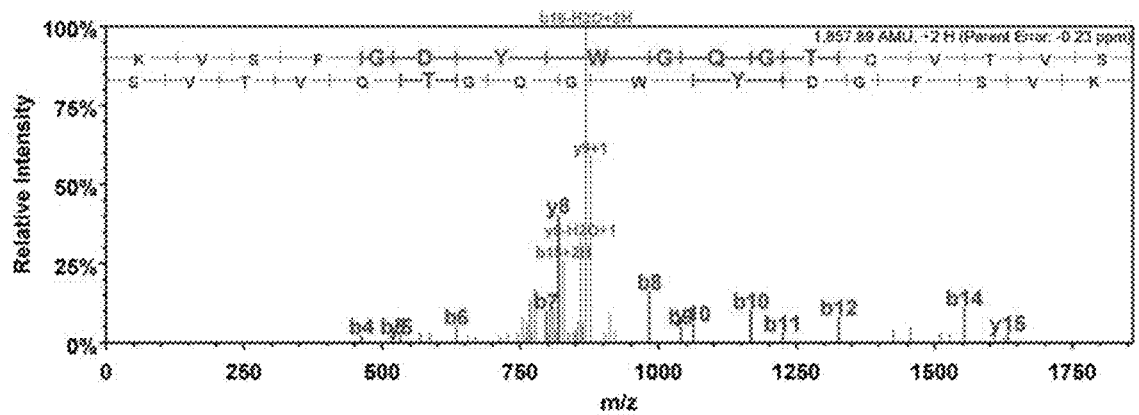

Figure 9 (continued)

LaG-26
MAQVQLVESGGGLVQAGASMRLSCAASGITFSLYHWVWFRQAAGREHEFVAGIIRSGGETLSADS
VKDRFIISRDDAKNTLYLQMNMLQPEDTATYYCAATHRADWYSSAFREYIFRGQGTQVTVS

LaG-27
MADVQLVESGGGLVQAGGSLRLSCTASGLTISTYNIGWFRQAPGKEREFVGIIRNGDTTYYADSVK
GRFTISRDNAKNTVYLQMNSVKPADAAVYSCGATVRAGAAAEQYNSYIFRGQGTQVTV

Figure 9 (continued)

LaG-29

MAQVQLVESGGGLVQAGAALRLSCAASGGTFSFYNMGWFRQAPGKEREFVVSISRSGGGTAYAD
SVKGRFTISRDNAKNTAYLQMNSLKPEDTAVYYCAAGLRDWGREGEPHYWGQGTQVTVS

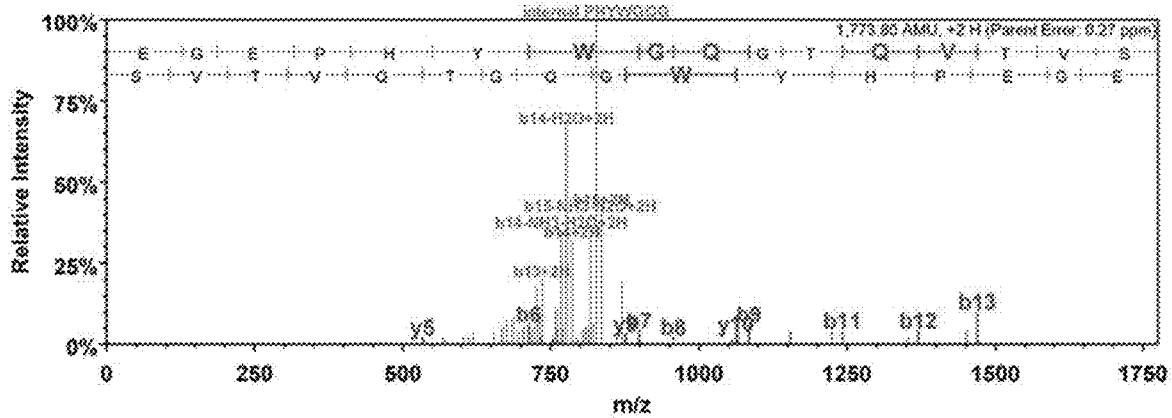

LaG-30

MAQVQLVESGGGLVQAGGSLRLSCAASGRTFSTSAMGWFRQAPGREREFVAAITWTVGNTIYGD
SMKGRFTISRDRTKNTVDLQMDSLKPEDTAVYYCTARSRGFVLSDLRSVDSFDYKGQGTQVTVS

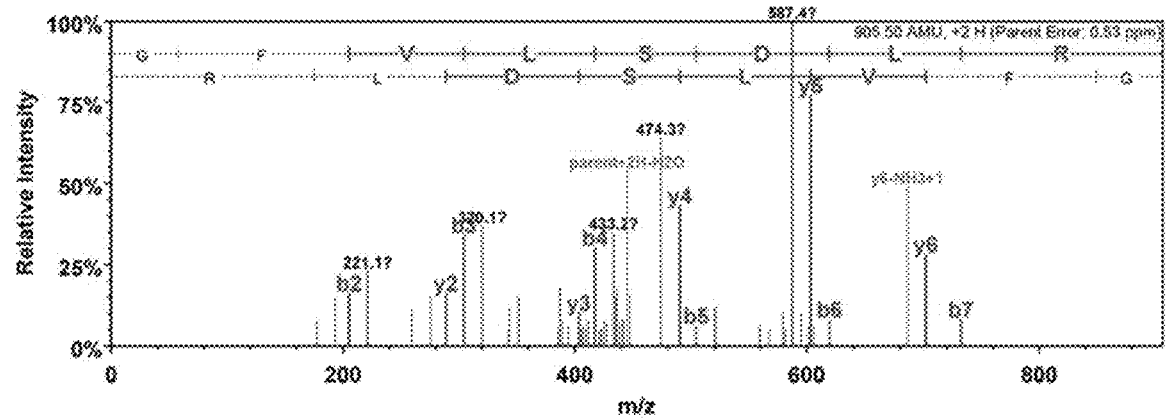

LaG-35

MADVQLVESGGGLVQAGGSLRLSCTVSGRTFSNYAMGWFRQAPGKEREFVAGISWTGGHTLYTD
SVKGRFTISRDNAKNTVYLQMNSLKPEDTALYYCAADRAADFFAQRDEYDYWGQGTQVTVS

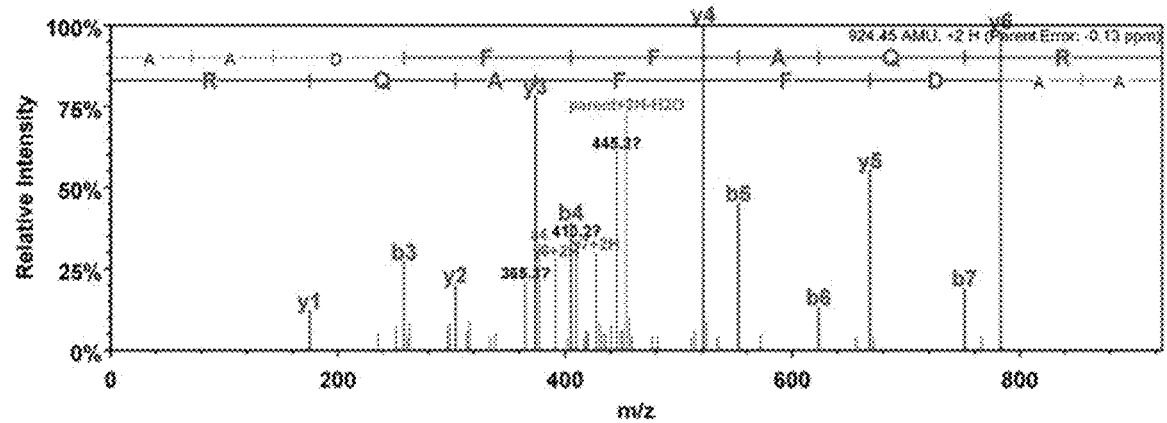

Figure 9 (continued)

LaM-1

MAQVQLVESGGGLVQAGDSLRLSCAASGRTFENYAMGWFRQAPGKEREFVGAVSWGGGRTYYAD

LaM-2

MAQVQLVESGGGLVQAGGSLRLSCATSGFTFSDYAMGWFRQAPGKEREFVAAISWSGHVTDYAD
SVKGRFTISRDNVKNTVYLQMNSLKPEDTAVYSCAAAKSGTWWYQRSENDFGSWGQGTQVTVSKEAI

LaM-3

MAQVQLVQSGGGLVQAGGSLRLSCAASGRTFSDIAVGWFRQTPGKEREFVAAISWSGLIINYGD
SVEDRFTISRDNAKSAVYLQMNSLKPEDTAVYYCAARIGMNYYYAREIEYPYWGQGTQVTVSKCY

LaM-4

MAQVQLVESGGSLVQPGGSLRLSCAASGRFAESSSMGWFRQAPGKEREFVAAISWSGGATNYAD
SAKGRFTLSRDNTKNTVYLQMNSLKPDDTAVYYCAANLGNYISSNQRLYGYWGQGTQVTVSSPFT

LaM-6

MAQVQLVESGGGLVQAGGSLRLSCVASGSAPSFFAMAWYRQSPGNERELVAALSSLGSTNYAD
SVKGRFTISMDNAKNTVYLQMNNVNAEDTAVYYCAAGDFHSCYARKSCDYWGQGTQVTVS

LaM-8

MAQVQLVESGGGLVQAGGSLRLSCAVSGRPFSEYNLGWFRQAPGKEREFVARIRSSGTTVYTD
SVKGRFSASRDNAKNMGYLQLNSLEPEDTAVYYCAMSRVDTDSPAFYDYWGQGTQVTVSTPRS

SEQUENCE LISTING

<160> NUMBER OF SEQ ID NOS: 44

<210> SEQ ID NO 1
<211> LENGTH: 255
<212> TYPE: PRT
<213> ORGANISM: artificial sequence
<220> FEATURE:
<223> OTHER INFORMATION: Artificial GFP

<400> SEQUENCE: 1

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val His Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys Gly
225                 230                 235                 240

Leu Glu Val Leu Phe Gln Gly Pro Ser His His His His His His
                245                 250                 255

<210> SEQ ID NO 2
<211> LENGTH: 237
<212> TYPE: PRT
<213> ORGANISM: artificial sequence
<220> FEATURE:
<223> OTHER INFORMATION: Artificial GFP

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg

```
                     85                  90                  95

Thr Ile Ser Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Leu Glu His His His His His His
225                 230                 235

<210> SEQ ID NO 3
<211> LENGTH: 237
<212> TYPE: PRT
<213> ORGANISM: artificial sequence
<220> FEATURE:
<223> OTHER INFORMATION: Artificial GFP

<400> SEQUENCE: 3

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Lys Leu Ser
        195                 200                 205

Lys Asp Pro Asn Glu Lys Arg Asp His Met Val Leu Leu Glu Phe Val
```

```
                210               215               220
Thr Ala Ala Gly Ile Leu Glu His His His His His His
225               230               235
```

<210> SEQ ID NO 4
<211> LENGTH: 23
<212> TYPE: DNA
<213> ORGANISM: artificial sequence
<220> FEATURE:
<223> OTHER INFORMATION: Primer

<400> SEQUENCE: 4
gtcctggctg ctcttctaca agg                                    23

<210> SEQ ID NO 5
<211> LENGTH: 23
<212> TYPE: DNA
<213> ORGANISM: artificial sequence
<220> FEATURE:
<223> OTHER INFORMATION: Primer

<400> SEQUENCE: 5
ggtacgtgct gttgaactgt tcc                                    23

<210> SEQ ID NO 6
<211> LENGTH: 54
<212> TYPE: DNA
<213> ORGANISM: artificial sequence
<220> FEATURE:
<223> OTHER INFORMATION: Primer
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 6
cgtatcgcct ccctcgcgcc atcagatggc tnangtgcag ctggtggagt ctgg    54

<210> SEQ ID NO 7
<211> LENGTH: 43
<212> TYPE: DNA
<213> ORGANISM: artificial sequence
<220> FEATURE:
<223> OTHER INFORMATION: Primer

<400> SEQUENCE: 7
ctatgcgcct tgccagcccg ctcagggaga cggtgacctg ggt               43

<210> SEQ ID NO 8
<211> LENGTH: 41
<212> TYPE: DNA
<213> ORGANISM: artificial sequence
<220> FEATURE:
<223> OTHER INFORMATION: Primer
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(21)

<223> OTHER INFORMATION: n is a, c, g, or t

<400> SEQUENCE: 8
nnnnnnnnnn nnatggctna ngtgcagctg gtggagtctg g    41

<210> SEQ ID NO 9
<211> LENGTH: 30
<212> TYPE: DNA
<213> ORGANISM: artificial sequence
<220> FEATURE:
<223> OTHER INFORMATION: Primer
<220> FEATURE:
<221> NAME/KEY: misc_feature
<222> LOCATION: (1)..(12)
<223> OTHER INFORMATION: n is a, c, g, or t

<400> SEQUENCE: 9
nnnnnnnnnn nnggagacgg tgacctgggt    30

<210> SEQ ID NO 10
<211> LENGTH: 127
<212> TYPE: PRT
<213> ORGANISM: llama

<400> SEQUENCE: 10

Met Ala Gln Val Gln Leu Val Glu Ser Gly Gly Gly Leu Val Gln Ala
1               5                   10                  15

Gly Gly Ser Leu Arg Leu Ser Cys Ala Ala Ser Gly Arg Thr Phe Ser
            20                  25                  30

Asn Tyr Ala Met Gly Trp Phe Arg Gln Ala Pro Gly Lys Glu Arg Glu
        35                  40                  45

Phe Val Ala Ala Ile Ser Trp Thr Gly Val Ser Thr Tyr Tyr Ala Asp
    50                  55                  60

Ser Val Lys Gly Arg Phe Thr Ile Ser Arg Asp Asn Asp Lys Asn Thr
65                  70                  75                  80

Val Tyr Val Gln Met Asn Ser Leu Ile Pro Glu Asp Thr Ala Ile Tyr
                85                  90                  95

Tyr Cys Ala Ala Val Arg Ala Arg Ser Phe Ser Asp Thr Tyr Ser Arg
            100                 105                 110

Val Asn Glu Tyr Asp Tyr Trp Gly Gln Gly Thr Gln Val Thr Val
        115                 120                 125

<210> SEQ ID NO 11
<211> LENGTH: 124
<212> TYPE: PRT
<213> ORGANISM: llama

<400> SEQUENCE: 11

Met Ala Gln Val Gln Leu Val Glu Ser Gly Gly Gly Leu Val Gln Ala
1               5                   10                  15

Gly Gly Ser Leu Arg Val Ser Cys Ala Ala Ser Gly Arg Thr Tyr Ser
            20                  25                  30

Asp Tyr Ala Met Gly Trp Phe Arg Gln Ala Pro Gly Lys Glu Arg Asp
        35                  40                  45

Phe Val Ala Gly Ile Ser Gly Ser Gly Gly Asp Thr Tyr Tyr Ala Asp
    50                  55                  60

Ser Val Lys Gly Arg Phe Thr Ile Ser Arg Asp Asn Ala Lys Asn Thr
65                  70                  75                  80

Met Tyr Leu Gln Met Asn Ser Leu Lys Pro Glu Asp Thr Ala Val Tyr
                85                  90                  95

-continued

Phe Cys Ala Ala Arg Thr Gly Thr Val Leu Phe Thr Ser Arg Val Asp
                100                 105                 110

Tyr Arg Tyr Trp Gly Gln Gly Thr Gln Val Thr Val
        115                 120

<210> SEQ ID NO 12
<211> LENGTH: 125
<212> TYPE: PRT
<213> ORGANISM: llama

<400> SEQUENCE: 12

Met Ala Gln Val Gln Leu Val Glu Ser Gly Gly Gly Leu Val Gln Ala
1               5                   10                  15

Gly Gly Ser Leu Arg Leu Ser Cys Ala Ala Ser Gly Ser Ile Phe Ser
            20                  25                  30

Ser Asn Ala Met Ala Trp Tyr Arg Gln Thr Pro Glu Lys Gln Arg Glu
        35                  40                  45

Leu Ile Cys Asp Ile Thr Arg Gly Gly Ile Thr Lys Cys Ala Asp Ser
    50                  55                  60

Val Lys Gly Arg Phe Thr Ile Ser Arg Asp Asn Thr Lys Asn Thr Val
65                  70                  75                  80

Tyr Leu Gln Met Asn Ser Leu Lys Ser Glu Asp Thr Ala Val Tyr Tyr
                85                  90                  95

Cys Ala Ala Lys Ser Glu Gly Tyr Phe Gly Phe Pro Arg Val Glu Asn
                100                 105                 110

Glu Tyr Pro Tyr Trp Gly Gln Gly Thr Gln Val Thr Val
        115                 120                 125

<210> SEQ ID NO 13
<211> LENGTH: 126
<212> TYPE: PRT
<213> ORGANISM: llama

<400> SEQUENCE: 13

Met Ala Gln Val Gln Leu Val Glu Ser Gly Gly Gly Leu Val Gln Ala
1               5                   10                  15

Gly Gly Ser Leu Arg Leu Ser Cys Ala Ala Ser Gly Arg Thr Phe Ser
            20                  25                  30

Thr Ser Ala Met Ala Trp Phe Arg Gln Ala Pro Gly Lys Glu Arg Glu
        35                  40                  45

Phe Ala Ala Gly Ile Thr Trp Ile Ser Ser Thr Tyr Tyr Thr Asp
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Ala Ala Lys Ser Glu Gly Tyr Phe Gly Phe Pro Arg Val Glu
                100                 105                 110

Asn Glu Tyr Pro Tyr Trp Gly Gln Gly Thr Gln Val Thr Val
            115                 120                 125

<210> SEQ ID NO 14
<211> LENGTH: 124
<212> TYPE: PRT
<213> ORGANISM: llama

<400> SEQUENCE: 14

```
Met Ala Gln Val Gln Leu Val Glu Ser Gly Gly Gly Leu Val Gln Ala
1               5                   10                  15

Gly Gly Ser Leu Arg Leu Ser Cys Val Ala Ser Gly Arg Thr Phe Ser
            20                  25                  30

Gly Tyr Ala Met Gly Trp Phe Arg Gln Thr Pro Gly Arg Glu Arg Glu
        35                  40                  45

Ala Val Ala Ala Ile Thr Trp Ser Ala His Ser Thr Tyr Tyr Ser Asp
    50                  55                  60

Ser Val Lys Asp Arg Phe Thr Ile Ser Ile Asp Asn Thr Arg Asn Thr
65                  70                  75                  80

Gly Tyr Leu Gln Met Asn Ser Leu Lys Pro Glu Asp Thr Ala Val Tyr
            85                  90                  95

Tyr Cys Thr Val Arg His Gly Thr Trp Phe Thr Thr Ser Arg Tyr Trp
            100                 105                 110

Thr Asp Trp Gly Gln Gly Thr Gln Val Thr Val Ser
            115                 120
```

```
<210> SEQ ID NO 15
<211> LENGTH: 124
<212> TYPE: PRT
<213> ORGANISM: llama

<400> SEQUENCE: 15

Met Ala Gln Val Gln Leu Val Glu Ser Gly Gly Gly Leu Val Gln His
1               5                   10                  15

Gly Gly Ser Leu Arg Leu Ser Cys Val Thr Ser Gly Phe Thr Phe Asp
            20                  25                  30

Ile His Asp Met Gly Trp Phe Arg Gln Ala Pro Gly Lys Glu Arg Asp
        35                  40                  45

Ile Val Ala Arg Ile Ser Lys Ser Gly Asp Ile Thr Tyr Tyr Ala Asp
    50                  55                  60

Ser Val Lys Gly Arg Phe Ile Ile Ser Arg Asp Asn Thr Lys Asn Thr
65                  70                  75                  80

Val Tyr Leu Gln Met Asn Ser Leu Lys Pro Glu Asp Thr Ala Val Tyr
            85                  90                  95

Tyr Cys Ala Ala Thr Leu Arg Ala Thr Ile Thr Ser Phe Asp Glu Tyr
            100                 105                 110

Val Tyr Arg Gly Gln Gly Thr Gln Val Thr Val Ser
            115                 120
```

```
<210> SEQ ID NO 16
<211> LENGTH: 127
<212> TYPE: PRT
<213> ORGANISM: llama

<400> SEQUENCE: 16

Met Ala Asp Val Gln Leu Val Glu Ser Gly Gly Gly Leu Val Gln Ala
1               5                   10                  15

Gly Gly Ser Leu Arg Leu Ser Cys Ala Ala Ser Gly Arg Thr Phe Ser
            20                  25                  30

Thr Ser Ala Met Gly Trp Phe Arg Gln Ala Pro Gly Lys Glu Arg Glu
            35                  40                  45

Phe Val Ala Arg Ile Thr Trp Ser Ala Gly Tyr Thr Ala Tyr Ser Asp
    50                  55                  60

Ser Val Lys Gly Arg Phe Thr Ile Ser Arg Asp Lys Ala Lys Asn Thr
65                  70                  75                  80
```

```
Val Tyr Leu Gln Met Asn Ser Leu Lys Pro Glu Asp Thr Ala Val Tyr
                 85                  90                  95

Tyr Cys Ala Ser Arg Ser Ala Gly Tyr Ser Ser Ser Leu Thr Arg Arg
            100                 105                 110

Glu Asp Tyr Ala Tyr Trp Gly Gln Gly Thr Gln Val Thr Val Ser
        115                 120                 125
```

<210> SEQ ID NO 17
<211> LENGTH: 124
<212> TYPE: PRT
<213> ORGANISM: llama

<400> SEQUENCE: 17

```
Met Ala Gln Val Gln Leu Val Glu Ser Gly Gly Gly Leu Val Gln Ala
1               5                   10                  15

Gly Asp Ser Leu Gln Leu Ser Cys Ala Phe Ser Gly Thr Phe Ser
            20                  25                  30

Thr Tyr Ala Met Gly Trp Phe Arg Gln Ala Pro Gly Lys Glu Arg Glu
            35                  40                  45

Phe Val Gly Gly Ile Ser Arg Ser Gly Ala Thr Thr Asn Tyr Glu Asp
        50                  55                  60

Ser Val Lys Gly Arg Phe Thr Ile Ser Lys Asp Asn Thr Lys Asn Thr
65                  70                  75                  80

Val Tyr Leu Gln Leu Asn Ser Leu Lys Pro Glu Asp Thr Ala Val Tyr
                85                  90                  95

Tyr Cys Ala Ala Arg Asn Asn Ile Leu Pro Val Thr Thr Ile Asp Lys
            100                 105                 110

Tyr Glu Tyr Trp Gly Gln Gly Thr Gln Val Thr Val
        115                 120
```

<210> SEQ ID NO 18
<211> LENGTH: 128
<212> TYPE: PRT
<213> ORGANISM: llama

<400> SEQUENCE: 18

```
Met Ala Asp Val Gln Leu Val Glu Ser Gly Gly Arg Ser Val Arg Ala
1               5                   10                  15

Gly Asp Ser Leu Arg Leu Ser Cys Leu Ala Ser Gly Gly Thr Phe Ser
            20                  25                  30

Leu Tyr Ala Met Gly Trp Phe Arg Gln Ala Pro Gly Lys Glu Arg Glu
            35                  40                  45

Phe Val Ala Ala Val Thr Trp Ser Gly Gly Ser Thr Tyr Tyr Thr Asp
        50                  55                  60

Ser Val Lys Gly Arg Phe Ser Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Ala Val Arg Thr Ser Gly Phe Phe Gly Ser Ile Pro Val Thr
            100                 105                 110

Glu Arg Ala Phe Asp Tyr Trp Gly Gln Gly Thr Gln Val Thr Val Ser
        115                 120                 125
```

<210> SEQ ID NO 19
<211> LENGTH: 129
<212> TYPE: PRT
<213> ORGANISM: llama

<400> SEQUENCE: 19

Met Ala Ser Gly Ala Gly Gly Leu Gly Glu Gly Leu Val Gln
1               5                   10                  15
Ala Gly Gly Ser Leu Arg Leu Ser Cys Ala Ala Ser Gly Arg Thr Phe
            20                  25                  30
Asn Ser Tyr Pro Met Ala Trp Phe Arg Gln Ala Pro Gly Lys Glu Arg
        35                  40                  45
Glu Phe Val Ala Ala Leu Gly Trp Ser Gly Gly Ser Thr Asp Tyr Ala
    50                  55                  60
Asp Ser Val Lys Gly Arg Phe Thr Ile Ser Arg Asp Asn Ser Lys Asn
65                  70                  75                  80
Thr Val Tyr Leu Glu Met Asn Ser Leu Lys Pro Asp Asp Thr Gly Val
                85                  90                  95
Tyr Tyr Cys Ala Leu Arg Arg Arg Gly Gly Val Tyr Asn Thr Tyr Ser
            100                 105                 110
Gly Glu Lys Asp Tyr Asp Tyr Trp Gly Gln Gly Thr Gln Val Thr Val
        115                 120                 125
Ser

<210> SEQ ID NO 20
<211> LENGTH: 126
<212> TYPE: PRT
<213> ORGANISM: llama

<400> SEQUENCE: 20

Met Ala Gln Val Gln Leu Val Glu Ser Gly Gly Gly Leu Val Gln Ala
1               5                   10                  15
Gly Gly Ser Leu Arg Leu Ser Cys Ala Ala Ser Gly Arg Thr Tyr Ser
            20                  25                  30
Ile Ser Ala Met Gly Trp Phe Arg Gln Ala Pro Gly Lys Glu Arg Glu
        35                  40                  45
Phe Val Ala Gly Ile Ser Arg Ser Gly Gly Thr Thr Tyr Tyr Ala Asp
    50                  55                  60
Pro Val Lys Gly Arg Phe Thr Ile Ser Arg Asp Asn Ala Lys Asn Thr
65                  70                  75                  80
Val Tyr Leu Gln Met Asn Ser Leu Lys Pro Glu Asp Thr Ala Val Tyr
                85                  90                  95
Tyr Cys Ala Ala Arg Ala Arg Gly Trp Thr Thr Phe Pro Ala Arg Glu
            100                 105                 110
Ile Glu Tyr Asp Tyr Trp Gly Gln Gly Thr Gln Val Thr Val
        115                 120                 125

<210> SEQ ID NO 21
<211> LENGTH: 128
<212> TYPE: PRT
<213> ORGANISM: llama

<400> SEQUENCE: 21

Met Ala Gln Val Gln Leu Val Glu Ser Gly Gly Arg Leu Val Gln Ala
1               5                   10                  15
Gly Asp Ser Leu Arg Leu Ser Cys Ala Ala Ser Gly Arg Thr Phe Ser
            20                  25                  30
Thr Ser Ala Met Ala Trp Phe Arg Gln Ala Pro Gly Arg Glu Arg Glu
        35                  40                  45
Phe Val Ala Ala Ile Thr Trp Thr Val Gly Asn Thr Ile Leu Gly Asp
    50                  55                  60

Ser Val Lys Gly Arg Phe Thr Ile Ser Arg Asp Arg Ala Lys Asn Thr
65                  70                  75                  80

Val Asp Leu Gln Met Asp Asn Leu Glu Pro Glu Asp Thr Ala Val Tyr
            85                  90                  95

Tyr Cys Ser Ala Arg Ser Arg Gly Tyr Val Leu Ser Val Leu Arg Ser
        100                 105                 110

Val Asp Ser Tyr Asp Tyr Trp Gly Gln Gly Thr Gln Val Thr Val Ser
    115                 120                 125

<210> SEQ ID NO 22
<211> LENGTH: 128
<212> TYPE: PRT
<213> ORGANISM: llama

<400> SEQUENCE: 22

Met Ala Asp Val Gln Leu Val Glu Ser Gly Gly Gly Leu Val Gln Ala
1               5                   10                  15

Gly Gly Ser Leu Arg Leu Ser Cys Ala Ala Ser Gly Arg Thr Ile Ser
            20                  25                  30

Met Ala Ala Met Ser Trp Phe Arg Gln Ala Pro Gly Lys Glu Arg Glu
        35                  40                  45

Phe Val Ala Gly Ile Ser Arg Ser Ala Gly Ser Ala Val His Ala Asp
    50                  55                  60

Ser Val Lys Gly Arg Phe Thr Ile Ser Arg Asp Asn Thr Lys Asn Thr
65                  70                  75                  80

Leu Tyr Leu Gln Met Asn Ser Leu Lys Ala Glu Asp Thr Ala Val Tyr
            85                  90                  95

Tyr Cys Ala Val Arg Thr Ser Gly Phe Phe Gly Ser Ile Pro Arg Thr
        100                 105                 110

Gly Thr Ala Phe Asp Tyr Trp Gly Gln Gly Thr Gln Val Thr Val Ser
    115                 120                 125

<210> SEQ ID NO 23
<211> LENGTH: 128
<212> TYPE: PRT
<213> ORGANISM: llama

<400> SEQUENCE: 23

Met Ala Gln Val Gln Leu Val Glu Ser Gly Gly Gly Leu Val Gln Thr
1               5                   10                  15

Gly Gly Ser Leu Lys Leu Ser Cys Thr Ala Ser Val Arg Thr Leu Ser
            20                  25                  30

Tyr Tyr His Val Gly Trp Phe Arg Gln Ala Pro Gly Lys Glu Arg Glu
        35                  40                  45

Phe Val Ala Gly Ile His Arg Ser Gly Glu Ser Thr Phe Tyr Ala Asp
    50                  55                  60

Ser Val Lys Gly Arg Phe Thr Ile Ser Arg Asp Asn Ala Lys Asn Thr
65                  70                  75                  80

Val His Leu Gln Met Asn Ser Leu Lys Pro Glu Asp Thr Ala Val Tyr
            85                  90                  95

Tyr Cys Ala Gln Arg Val Arg Gly Phe Phe Gly Pro Leu Arg Ser Thr
        100                 105                 110

Pro Ser Trp Tyr Asp Tyr Trp Gly Gln Gly Thr Gln Val Thr Val Ser
    115                 120                 125

<210> SEQ ID NO 24

<211> LENGTH: 122
<212> TYPE: PRT
<213> ORGANISM: llama

<400> SEQUENCE: 24

```
Met Ala Gln Val Gln Leu Val Glu Ser Gly Gly Gly Leu Val Gln Ala
1               5                   10                  15
Gly Gly Ser Leu Arg Leu Ser Cys Ala Ala Ser Gly Pro Thr Gly Ala
            20                  25                  30
Met Ala Trp Phe Arg Gln Ala Pro Gly Lys Glu Arg Glu Phe Val Gly
        35                  40                  45
Gly Ile Ser Arg Ser Gly Thr Asp Thr Tyr Tyr Val Asp Ser Val Lys
    50                  55                  60
Gly Arg Phe Thr Ile Asp Arg Asp Asn Ala Lys Asn Thr Val Tyr Leu
65                  70                  75                  80
Gln Met Asn Ser Leu Lys Pro Glu Asp Thr Ala Val Tyr Tyr Cys Ala
                85                  90                  95
Ala Arg Arg Ser Gln Ile Leu Phe Thr Ser Arg Thr Asp Tyr Glu Phe
            100                 105                 110
Trp Gly Gln Gly Thr Gln Val Thr Val Ser
        115                 120
```

<210> SEQ ID NO 25
<211> LENGTH: 122
<212> TYPE: PRT
<213> ORGANISM: llama

<400> SEQUENCE: 25

```
Met Ala Gln Val Gln Leu Val Glu Ser Gly Gly Gly Leu Val Gln Ala
1               5                   10                  15
Gly Gly Ser Leu Arg Leu Ser Cys Ala Ala Ser Gly Pro Thr Gly Ala
            20                  25                  30
Met Ala Trp Phe Arg Gln Ala Pro Gly Met Glu Arg Glu Phe Val Gly
        35                  40                  45
Gly Ile Ser Gly Ser Glu Thr Asp Thr Tyr Tyr Ala Asp Phe Val Lys
    50                  55                  60
Gly Arg Leu Thr Val Asp Arg Asp Asn Val Lys Asn Thr Val Asp Leu
65                  70                  75                  80
Gln Met Asn Ser Leu Lys Pro Glu Asp Thr Ala Val Tyr Tyr Cys Ala
                85                  90                  95
Ala Arg Arg Arg Val Thr Leu Phe Thr Ser Arg Ala Asp Tyr Asp Phe
            100                 105                 110
Trp Gly Gln Gly Thr Gln Val Thr Val Ser
        115                 120
```

<210> SEQ ID NO 26
<211> LENGTH: 117
<212> TYPE: PRT
<213> ORGANISM: llama

<400> SEQUENCE: 26

```
Met Ala Asp Val Gln Leu Val Glu Ser Gly Gly Gly Leu Val Gln Pro
1               5                   10                  15
Gly Gly Ser Leu Arg Leu Ser Cys Ala Ala Ser Gly Glu Ile Ala Ser
            20                  25                  30
Ile Ile Ala Ile Gly Trp Tyr Arg Gln Ala Pro Gly Lys Gln Arg Glu
        35                  40                  45
```

```
Ser Val Ala Leu Ile Thr Arg Ser Gly Met Ile Thr Tyr Gly Asp Ser
    50                  55                  60

Ala Gln Gly Arg Phe Thr Ile Ser Arg Asp Asp Ala Lys Asn Thr Val
 65                  70                  75                  80

Tyr Leu His Met Asp Asp Leu Val Pro Glu Asp Thr Ala Val Tyr Tyr
                 85                  90                  95

Cys Asn Ala Lys Lys Val Ser Phe Gly Asp Tyr Trp Gly Gln Gly Thr
                100                 105                 110

Gln Val Thr Val Ser
            115

<210> SEQ ID NO 27
<211> LENGTH: 126
<212> TYPE: PRT
<213> ORGANISM: llama

<400> SEQUENCE: 27

Met Ala Gln Val Gln Leu Val Glu Ser Gly Gly Gly Leu Val Gln Ala
 1               5                  10                  15

Gly Ala Ser Met Arg Leu Ser Cys Ala Ala Ser Gly Ile Thr Phe Ser
                 20                  25                  30

Leu Tyr His Trp Val Trp Phe Arg Gln Ala Ala Gly Arg Glu His Glu
             35                  40                  45

Phe Val Ala Gly Ile Ile Arg Ser Gly Gly Thr Leu Ser Ala Asp
    50                  55                  60

Ser Val Lys Asp Arg Phe Ile Ile Ser Arg Asp Asp Ala Lys Asn Thr
 65                  70                  75                  80

Leu Tyr Leu Gln Met Asn Met Leu Gln Pro Glu Asp Thr Ala Thr Tyr
                 85                  90                  95

Tyr Cys Ala Ala Thr His Arg Ala Asp Trp Tyr Ser Ser Ala Phe Arg
                100                 105                 110

Glu Tyr Ile Phe Arg Gly Gln Gly Thr Gln Val Thr Val Ser
            115                 120                 125

<210> SEQ ID NO 28
<211> LENGTH: 125
<212> TYPE: PRT
<213> ORGANISM: llama

<400> SEQUENCE: 28

Met Ala Asp Val Gln Leu Val Glu Ser Gly Gly Gly Leu Val Gln Ala
 1               5                  10                  15

Gly Gly Ser Leu Arg Leu Ser Cys Thr Ala Ser Gly Leu Thr Ile Ser
                 20                  25                  30

Thr Tyr Asn Ile Gly Trp Phe Arg Gln Ala Pro Gly Lys Glu Arg Glu
             35                  40                  45

Phe Val Gly Ile Ile Ile Arg Asn Gly Asp Thr Thr Tyr Tyr Ala Asp
    50                  55                  60

Ser Val Lys Gly Arg Phe Thr Ile Ser Arg Asp Asn Ala Lys Asn Thr
 65                  70                  75                  80

Val Tyr Leu Gln Met Asn Ser Val Lys Pro Ala Asp Ala Val Tyr
                 85                  90                  95

Ser Cys Gly Ala Thr Val Arg Ala Gly Ala Ala Ala Glu Gln Tyr Asn
                100                 105                 110

Ser Tyr Ile Phe Arg Gly Gln Gly Thr Gln Val Thr Val
            115                 120                 125
```

<210> SEQ ID NO 29
<211> LENGTH: 123
<212> TYPE: PRT
<213> ORGANISM: llama

<400> SEQUENCE: 29

Met Ala Gln Val Gln Leu Val Glu Ser Gly Gly Gly Leu Val Gln Ala
1               5                   10                  15

Gly Ala Ala Leu Arg Leu Ser Cys Ala Ala Ser Gly Gly Thr Phe Ser
            20                  25                  30

Phe Tyr Asn Met Gly Trp Phe Arg Gln Ala Pro Gly Lys Glu Arg Glu
        35                  40                  45

Phe Val Val Ser Ile Ser Arg Ser Gly Gly Thr Ala Tyr Ala Asp
    50                  55                  60

Ser Val Lys Gly Arg Phe Thr Ile Ser Arg Asp Asn Ala Lys Asn Thr
65                  70                  75                  80

Ala Tyr Leu Gln Met Asn Ser Leu Lys Pro Glu Asp Thr Ala Val Tyr
                85                  90                  95

Tyr Cys Ala Ala Gly Leu Arg Asp Trp Gly Arg Glu Gly Glu Pro His
            100                 105                 110

Tyr Trp Gly Gln Gly Thr Gln Val Thr Val Ser
        115                 120

<210> SEQ ID NO 30
<211> LENGTH: 128
<212> TYPE: PRT
<213> ORGANISM: llama

<400> SEQUENCE: 30

Met Ala Gln Val Gln Leu Val Glu Ser Gly Gly Gly Leu Val Gln Ala
1               5                   10                  15

Gly Gly Ser Leu Arg Leu Ser Cys Ala Ala Ser Gly Arg Thr Phe Ser
            20                  25                  30

Thr Ser Ala Met Gly Trp Phe Arg Gln Ala Pro Gly Arg Glu Arg Glu
        35                  40                  45

Phe Val Ala Ala Ile Thr Trp Thr Val Gly Asn Thr Ile Tyr Gly Asp
    50                  55                  60

Ser Met Lys Gly Arg Phe Thr Ile Ser Arg Asp Arg Thr Lys Asn Thr
65                  70                  75                  80

Val Asp Leu Gln Met Asp Ser Leu Lys Pro Glu Asp Thr Ala Val Tyr
                85                  90                  95

Tyr Cys Thr Ala Arg Ser Arg Gly Phe Val Leu Ser Asp Leu Arg Ser
            100                 105                 110

Val Asp Ser Phe Asp Tyr Lys Gly Gln Gly Thr Gln Val Thr Val Ser
        115                 120                 125

<210> SEQ ID NO 31
<211> LENGTH: 125
<212> TYPE: PRT
<213> ORGANISM: llama

<400> SEQUENCE: 31

Met Ala Asp Val Gln Leu Val Glu Ser Gly Gly Gly Leu Val Gln Ala
1               5                   10                  15

Gly Gly Ser Leu Arg Leu Ser Cys Thr Val Ser Gly Arg Thr Phe Ser
            20                  25                  30

Asn Tyr Ala Met Gly Trp Phe Arg Gln Ala Pro Gly Lys Glu Arg Glu

```
                35                  40                  45
Phe Val Ala Gly Ile Ser Trp Thr Gly Gly His Thr Leu Tyr Thr Asp
        50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Leu Tyr
                85                  90                  95

Tyr Cys Ala Ala Asp Arg Ala Asp Phe Phe Ala Gln Arg Asp Glu
            100                 105                 110

Tyr Asp Tyr Trp Gly Gln Gly Thr Gln Val Thr Val Ser
            115                 120                 125

<210> SEQ ID NO 32
<211> LENGTH: 128
<212> TYPE: PRT
<213> ORGANISM: llama

<400> SEQUENCE: 32

Met Ala Gln Val Gln Phe Val Glu Ser Gly Gly Thr Val Gln Asp
1               5                   10                  15

Gly Asp Phe Leu Arg Leu Ser Cys Thr Ala Ser Gly Thr Phe Ser
            20                  25                  30

Asn Tyr His Ala Gly Trp Phe Arg Gln Pro Pro Gly Arg Glu Arg Glu
        35                  40                  45

Phe Val Ala Ala Ile Ser Trp Thr Gly Glu Gly Thr Leu Tyr Ala Asp
        50                  55                  60

Ser Val Lys Gly Gln Phe Thr Ile Ser Arg Asp Asn Ala Lys Asn Ala
65                  70                  75                  80

Met Tyr Leu Gln Met Asn Arg Leu Lys Pro Glu Asp Thr Ala Val Tyr
                85                  90                  95

Tyr Cys Ala Ala Ala Arg Ser Val Gly Phe Thr Trp Arg Ser Ser Lys
            100                 105                 110

Ser Asn Asp Tyr Ala Tyr Trp Gly Gln Gly Thr Gln Val Thr Val Gly
            115                 120                 125

<210> SEQ ID NO 33
<211> LENGTH: 121
<212> TYPE: PRT
<213> ORGANISM: llama

<400> SEQUENCE: 33

Met Ala Asp Val Gln Leu Val Glu Ser Gly Gly Gly Leu Val Gln Ala
1               5                   10                  15

Gly Gly Ser Leu Arg Leu Ser Cys Ala Ala Ser Gly Pro Thr Gly Ala
            20                  25                  30

Met Ala Trp Phe Arg Gln Ala Pro Gly Lys Glu Arg Glu Phe Val Gly
            35                  40                  45

Gly Ile Ser Gly Ser Glu Thr Asp Thr Tyr Tyr Val Asp Ser Val Lys
            50                  55                  60

Gly Arg Phe Thr Val Asp Arg Asp Asn Val Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Arg Arg Ile Thr Leu Phe Thr Ser Arg Thr Asp Tyr Asp Phe
            100                 105                 110

Trp Gly Arg Gly Thr Gln Val Thr Val
```

115                 120

<210> SEQ ID NO 34
<211> LENGTH: 122
<212> TYPE: PRT
<213> ORGANISM: llama

<400> SEQUENCE: 34

Met Ala Asp Val Gln Leu Val Glu Ser Gly Gly Gly Leu Val Gln Ala
1               5                   10                  15

Gly Asp Ser Leu Arg Leu Ser Cys Ala Ala Ser Gly Pro Thr Gly Ala
            20                  25                  30

Met Ala Trp Phe His Gln Gly Leu Gly Lys Glu Arg Glu Phe Val Gly
        35                  40                  45

Gly Ile Ser Pro Ser Gly Asp Asn Ile Tyr Tyr Ala Asp Ser Val Lys
    50                  55                  60

Gly Arg Phe Thr Ile Asp Arg Asp Asn Ala Lys Asn Thr Val Ser Leu
65                  70                  75                  80

Gln Met Asn Ser Leu Lys Pro Glu Asp Met Gly Val Tyr Tyr Cys Ala
                85                  90                  95

Ala Arg Arg Arg Val Thr Leu Phe Thr Ser Arg Thr Asp Tyr Glu Phe
            100                 105                 110

Trp Gly Arg Gly Thr Gln Val Thr Val Ser
        115                 120

<210> SEQ ID NO 35
<211> LENGTH: 128
<212> TYPE: PRT
<213> ORGANISM: llama

<400> SEQUENCE: 35

Met Ala Asp Val Gln Leu Val Glu Ser Gly Gly Gly Leu Val Gln Pro
1               5                   10                  15

Gly Gly Ser Leu Arg Leu Ser Cys Glu Ala Ser Gly Gly Ala Phe Ser
            20                  25                  30

Thr Val Ala Met Gly Trp Phe Arg Gln Ala Pro Gly Lys Glu Arg Glu
        35                  40                  45

Phe Val Gly Ala Ile Thr Trp Thr Ala Gly Ser Thr Tyr Tyr Ala Asp
    50                  55                  60

Ser Ala Lys Gly Arg Phe Thr Ile Ser Arg Asp Asn Ala Lys Asn Thr
65                  70                  75                  80

Val His Leu Gln Met Asn Ser Leu Lys Pro Glu Asp Thr Ala Val Tyr
                85                  90                  95

Tyr Cys Ala Gln Arg Val Arg Gly Phe Phe Gly Pro Leu Arg Thr Thr
            100                 105                 110

Pro Ser Trp Tyr Glu Tyr Trp Gly Gln Gly Thr Gln Val Thr Val Ser
        115                 120                 125

<210> SEQ ID NO 36
<211> LENGTH: 128
<212> TYPE: PRT
<213> ORGANISM: llama

<400> SEQUENCE: 36

Met Ala Gln Val Gln Leu Val Glu Ser Gly Gly Gly Leu Val Gln Ala
1               5                   10                  15

Gly Asp Ser Leu Arg Leu Ser Cys Ala Ala Ser Gly Arg Thr Phe Glu
            20                  25                  30

Asn Tyr Ala Met Gly Trp Phe Arg Gln Ala Pro Gly Lys Glu Arg Glu
                35                  40                  45

Phe Val Gly Ala Val Ser Trp Gly Gly Arg Thr Tyr Tyr Ala Asp
 50                  55                  60

Asn Val Lys Gly Arg Phe Thr Ile Ser Arg Asp Asn Ala Lys Lys Asn
 65                  70                  75                  80

Thr Val Tyr Leu Gln Met Asn Ser Leu Lys Pro Glu Asp Thr Ala Val
                 85                  90                  95

Tyr Tyr Cys Ala Ala Lys Ser Val Leu Thr Ile Ala Thr Met Arg Val
                100                 105                 110

Pro Asp Glu Tyr Asn Tyr Trp Gly Gln Gly Thr Gln Val Thr Val Ser
                115                 120                 125

<210> SEQ ID NO 37
<211> LENGTH: 127
<212> TYPE: PRT
<213> ORGANISM: llama

<400> SEQUENCE: 37

Met Ala Gln Val Gln Leu Val Glu Ser Gly Gly Gly Leu Val Gln Ala
 1               5                  10                  15

Gly Gly Ser Leu Arg Leu Ser Cys Ala Thr Ser Gly Phe Thr Phe Ser
                 20                  25                  30

Asp Tyr Ala Met Gly Trp Phe Arg Gln Ala Pro Gly Lys Glu Arg Glu
                35                  40                  45

Phe Val Ala Ala Ile Ser Trp Ser Gly His Val Thr Asp Tyr Ala Asp
 50                  55                  60

Ser Val Lys Gly Arg Phe Thr Ile Ser Arg Asp Asn Val Lys Asn Thr
 65                  70                  75                  80

Val Tyr Leu Gln Met Asn Ser Leu Lys Pro Glu Asp Thr Ala Val Tyr
                 85                  90                  95

Ser Cys Ala Ala Ala Lys Ser Gly Thr Trp Trp Tyr Gln Arg Ser Glu
                100                 105                 110

Asn Asp Phe Gly Ser Trp Gly Gln Gly Thr Gln Val Thr Val Ser
                115                 120                 125

<210> SEQ ID NO 38
<211> LENGTH: 126
<212> TYPE: PRT
<213> ORGANISM: llama

<400> SEQUENCE: 38

Met Ala Gln Val Gln Leu Val Gln Ser Gly Gly Gly Leu Val Gln Ala
 1               5                  10                  15

Gly Gly Ser Leu Arg Leu Ser Cys Ala Ala Ser Gly Arg Thr Phe Ser
                 20                  25                  30

Asp Ile Ala Val Gly Trp Phe Arg Gln Thr Pro Gly Lys Glu Arg Glu
                35                  40                  45

Phe Val Ala Ala Ile Ser Trp Ser Gly Leu Ile Ile Asn Tyr Gly Asp
 50                  55                  60

Ser Val Glu Asp Arg Phe Thr Ile Ser Arg Asp Asn Ala Lys Ser Ala
 65                  70                  75                  80

Val Tyr Leu Gln Met Asn Ser Leu Lys Pro Glu Asp Thr Ala Val Tyr
                 85                  90                  95

Tyr Cys Ala Ala Arg Ile Gly Met Asn Tyr Tyr Ala Arg Glu Ile
                100                 105                 110

Glu Tyr Pro Tyr Trp Gly Gln Gly Thr Gln Val Thr Val Ser
            115                 120                 125

<210> SEQ ID NO 39
<211> LENGTH: 126
<212> TYPE: PRT
<213> ORGANISM: llama

<400> SEQUENCE: 39

Met Ala Gln Val Gln Leu Val Glu Ser Gly Gly Ser Leu Val Gln Pro
1               5                   10                  15

Gly Gly Ser Leu Arg Leu Ser Cys Ala Ala Ser Gly Arg Phe Ala Glu
            20                  25                  30

Ser Ser Ser Met Gly Trp Phe Arg Gln Ala Pro Gly Lys Glu Arg Glu
        35                  40                  45

Phe Val Ala Ala Ile Ser Trp Ser Gly Gly Ala Thr Asn Tyr Ala Asp
    50                  55                  60

Ser Ala Lys Gly Arg Phe Thr Leu Ser Arg Asp Asn Thr Lys Asn Thr
65                  70                  75                  80

Val Tyr Leu Gln Met Asn Ser Leu Lys Pro Asp Asp Thr Ala Val Tyr
                85                  90                  95

Tyr Cys Ala Ala Asn Leu Gly Asn Tyr Ile Ser Ser Asn Gln Arg Leu
            100                 105                 110

Tyr Gly Tyr Trp Gly Gln Gly Thr Gln Val Thr Val Ser Ser
            115                 120                 125

<210> SEQ ID NO 40
<211> LENGTH: 123
<212> TYPE: PRT
<213> ORGANISM: llama

<400> SEQUENCE: 40

Met Ala Gln Val Gln Leu Val Glu Ser Gly Gly Gly Leu Val Gln Ala
1               5                   10                  15

Gly Gly Ser Leu Arg Leu Ser Cys Val Ala Ser Gly Ser Ala Pro Ser
            20                  25                  30

Phe Phe Ala Met Ala Trp Tyr Arg Gln Ser Pro Gly Asn Glu Arg Glu
        35                  40                  45

Leu Val Ala Ala Leu Ser Ser Leu Gly Ser Thr Asn Tyr Ala Asp Ser
    50                  55                  60

Val Lys Gly Arg Phe Thr Ile Ser Met Asp Asn Ala Lys Asn Thr Val
65                  70                  75                  80

Tyr Leu Gln Met Asn Asn Val Asn Ala Glu Asp Thr Ala Val Tyr Tyr
                85                  90                  95

Cys Ala Ala Gly Asp Phe His Ser Cys Tyr Ala Arg Lys Ser Cys Asp
            100                 105                 110

Tyr Trp Gly Gln Gly Thr Gln Val Thr Val Ser
            115                 120

<210> SEQ ID NO 41
<211> LENGTH: 122
<212> TYPE: PRT
<213> ORGANISM: llama

<400> SEQUENCE: 41

Met Ala Gln Val Gln Leu Val Glu Ser Gly Gly Gly Leu Val Gln Ala
1               5                   10                  15

```
Gly Gly Ser Leu Arg Leu Ser Cys Ala Val Ser Gly Arg Pro Phe Ser
        20                  25                  30

Glu Tyr Asn Leu Gly Trp Phe Arg Gln Ala Pro Gly Lys Glu Arg Glu
            35                  40                  45

Phe Val Ala Arg Ile Arg Ser Ser Gly Thr Thr Val Tyr Thr Asp Ser
        50                  55                  60

Val Lys Gly Arg Phe Ser Ala Ser Arg Asp Asn Ala Lys Asn Met Gly
65                  70                  75                  80

Tyr Leu Gln Leu Asn Ser Leu Glu Pro Glu Asp Thr Ala Val Tyr Tyr
                85                  90                  95

Cys Ala Met Ser Arg Val Asp Thr Asp Ser Pro Ala Phe Tyr Asp Tyr
                100                 105                 110

Trp Gly Gln Gly Thr Gln Val Thr Val Ser
            115                 120

<210> SEQ ID NO 42
<211> LENGTH: 68
<212> TYPE: DNA
<213> ORGANISM: artificial sequence
<220> FEATURE:
<223> OTHER INFORMATION: Primer

<400> SEQUENCE: 42
tatgaaatac ttattgccta cggcagccgc tggattgtta ttactcgcgg cccagccggc    60
catggctg                                                             68

<210> SEQ ID NO 43
<211> LENGTH: 70
<212> TYPE: DNA
<213> ORGANISM: artificial sequence
<220> FEATURE:
<223> OTHER INFORMATION: Primer

<400> SEQUENCE: 43
gatccagcca tggccggctg ggccgcgagt aataacaatc cagcggctgc cgtaggcaat    60
aagtatttca                                                           70

<210> SEQ ID NO 44
<211> LENGTH: 5
<212> TYPE: PRT
<213> ORGANISM: artificial sequence
<220> FEATURE:
<223> OTHER INFORMATION: linker

<400> SEQUENCE: 44

Gly Gly Gly Gly Ser
1               5
```

COMPOSITIONS AND METHODS FOR RAPID PRODUCTION OF VERSATILE NANOBODY REPERTOIRES

CROSS-REFERENCE TO RELATED APPLICATIONS

This application is a continuation of U.S. patent application Ser. No. 15/320,811, filed Dec. 21, 2016, which is a National Phase entry of International Patent Application No. PCT/US2015/037678, filed Jun. 25, 2015, which claims priority to U.S. Provisional Patent Application No. 62/017,087, filed Jun. 25, 2014, the disclosures of each of which are incorporated herein by reference.

STATEMENT REGARDING FEDERALLY SPONSORED RESEARCH OR DEVELOPMENT

This invention was made with government support under contract nos. U54 GM103511 and P41 GM103314 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII file, created on May 4, 2022, is named RU_US_00055.txt, and is 49,152 bytes in size.

FIELD

The present disclosure relates generally to novel single domain antibodies and improved methods for making diverse catalogs of such antibodies against any desired antigen(s).

BACKGROUND

There is a continuing need in biomedicine for reagents such as antibodies that recognize target molecules with high affinity and specificity. When high affinity antibodies are not available, common protein tags such as GFP, FLAG, and myc have been invaluable for many cell biological and biochemical applications. However, most such studies still demand high quality antibodies against these protein tags, particularly when affinity isolation is required[1-4]. Although monoclonal or polyclonal antibodies remain the primary bait reagents available for these purposes, their large size, limited availability, batch to batch variation, and the frequent non-specific IgG contamination inherent to these reagents have often proved problematic for biochemical or proteomic studies[5].

An alternative to traditional antibodies has emerged, that of "single domain antibodies," also referred to as nanobodies[6]. Antibodies from camelids, such as llamas, include a unique subset of immunoglobulins consisting of heavy chain homodimers devoid of light chains[7-9]. Their variable region ($V_H H$) is the smallest antigen-binding fragment found in the antibody world, and as a single polypeptide chain it is especially suitable for protein engineering[8-12]. Single domain antibodies are the recombinant minimal-sized, intact antigen-binding domains derived from the $V_H H$ region of these heavy-chain antibodies. Unlike monoclonal antibodies, they can be readily produced in large amounts in simple bacterial expression systems[9,13]. Moreover, nanobodies are usually extremely stable, can bind antigens with affinities in the nanomolar range, and are smaller in size (approximately 15 kDa) and thereby easier to manipulate genetically as compared with antibody fragments such as ScFvs[11,14-18]. However, rapid and robust techniques for the isolation of extensive repertoires of high affinity nanobodies have proven elusive—the labor-intensive nature and poor efficiency of current approaches (e.g., phage display) have proven a major bottleneck for the widespread implementation of these reagents[8,12,14], explaining why demand for these reagents greatly exceeds supply[19]. The present disclosure meets these and other needs.

SUMMARY

The present disclosure relates to producing large repertoires of recombinant nanobodies with high affinities and specificities against any antigen. Representative and non-limiting examples of nanobodies that are aspects of this disclosure, and which demonstrate feasibility of generating large repertoires against any antigen are provided.

Generally the disclosure provides a method for identifying those regions of the antibodies produced by camelids from which nanobodies are derived, the nanobodies themselves, modifications of the nanobodies, expression vectors encoding the nanobodies, cDNAs encoding the nanobodies, cells comprising the expression vectors and/or cDNA, and methods of making the nanobodies.

In embodiments, the disclosure comprises nanobody production by introducing one or more antigens into the camelids, and recombinant methods for producing nanobodies that bind with specificity to the antigen(s) (Ag-specific nanobodies). The nanobodies that are a subject of this disclosure comprise a heavy chain only IgG class of antibodies (HCAbs). Accordingly, they are comprised of contain heavy chain homodimers, and do not contain antibody light chains. In embodiments, the HCAbs comprise or consist of 110 amino acids long and comprise a single variable domain (VHH) and two constant domains (CH2 and CH3). The single variable domain comprises three complementarity-determining regions (CDRs).

In one aspect the disclosure comprises a method for identifying and/or isolating Ag-specific HCAbs method comprising: i) introducing into a camelid a desired antigen such that a plurality of Ag-specific HCAbs is produced by the camelid; ii) testing lymphocytes obtained from the camelid to determine polynucleotide sequences encoding the variable region (VHH) of a mixed population of HCAbs that includes the plurality of Ag-specific HCAbs and HCAbs that are not specific for the antigen (referred to herein as non-specific HCAbs), and deducing the amino acid sequences of the VHH regions of the Ag-specific HCAbs and non-specific HCAbs in the mixed population from the polynucleotide sequences. In an embodiment the method further comprises iii) processing a sample from the camelid to separate Ag-specific HCAbs from non-specific HCAbs and determining the amino acid sequences of at least a portion of the VHH regions of the Ag-specific HCAbs, which can optionally be performed without proteolytic digestion (e.g., papain digestion), and iv) comparing deduced amino acid sequences of ii) with amino acid sequences of iii) to identify amino acid sequences of ii) that are the same as the amino acid sequences of iii), thereby identifying the Ag-specific VHH regions that are members of the mixed population of HCAbs. In embodiments, at least the comparing step is performed by a computer and using an algorithm, and may include a microprocessor implemented comparison of the amino acid sequences, such as a microprocessor implemented comparison of the calculated fragmentation patterns of the deduced amino acid sequences of ii) and the fragmentation pattern of the amino acid sequences of iii) measured by tandem mass spectrometry.

Methods of the disclosure are suited for determining large numbers of sequences. In one embodiment, determining the polynucleotide sequences of ii) comprises generating and sequencing a plurality of cDNA sequences that encode in certain embodiments at least 100, 200, 300, 400, 500, 600, 700, 800, 900, 1,000, 2,000, 3,000, 4,000, 5,000, 6,000, 7,000, 8,000, 9,000, or at least 10,000 unique VHH regions. Thus, in embodiments, the plurality of cDNAs comprises at least between 100 and 10,000 cDNAs, inclusive, and including all integers and ranges of integers there between.

In certain aspects the disclosure includes separating Ag-specific antibodies or antigen-binding fragments thereof from the non-specific antibodies by affinity purification of the Ag-specific antibodies using the antigen as an affinity capture agent.

In certain embodiments, for use in the identification of the VHH regions, lymphocytes, such as B plasma cells, are obtained from any suitable source in the camelid, including but not necessarily limited to the bone marrow of the camelid, or from, for example, a biological fluid obtained from the camelid, such as being obtained from fractionated blood, or from an affinity-isolated B cell preparation, or any other source and/or means by which plasma B cells can be obtained from the camelid.

In another aspect the disclosure further comprises providing and introducing distinct expression vectors encoding distinct Ag-specific nanobodies into host cells, wherein the nanobody sequences are designed based on the deduced Ag-specific VHH regions allowing expression of the distinct Ag-specific nanobodies from the host cells, separating the Ag-specific nanobodies from the host cells, and testing the Ag-specific nanobodies for binding to the antigen.

In embodiments, any one or any combination of Ag-specific nanobodies or antigen-binding fragments thereof have a Kd for the antigen in a sub-micromolar range.

DETAILED DESCRIPTION

Figure 1:
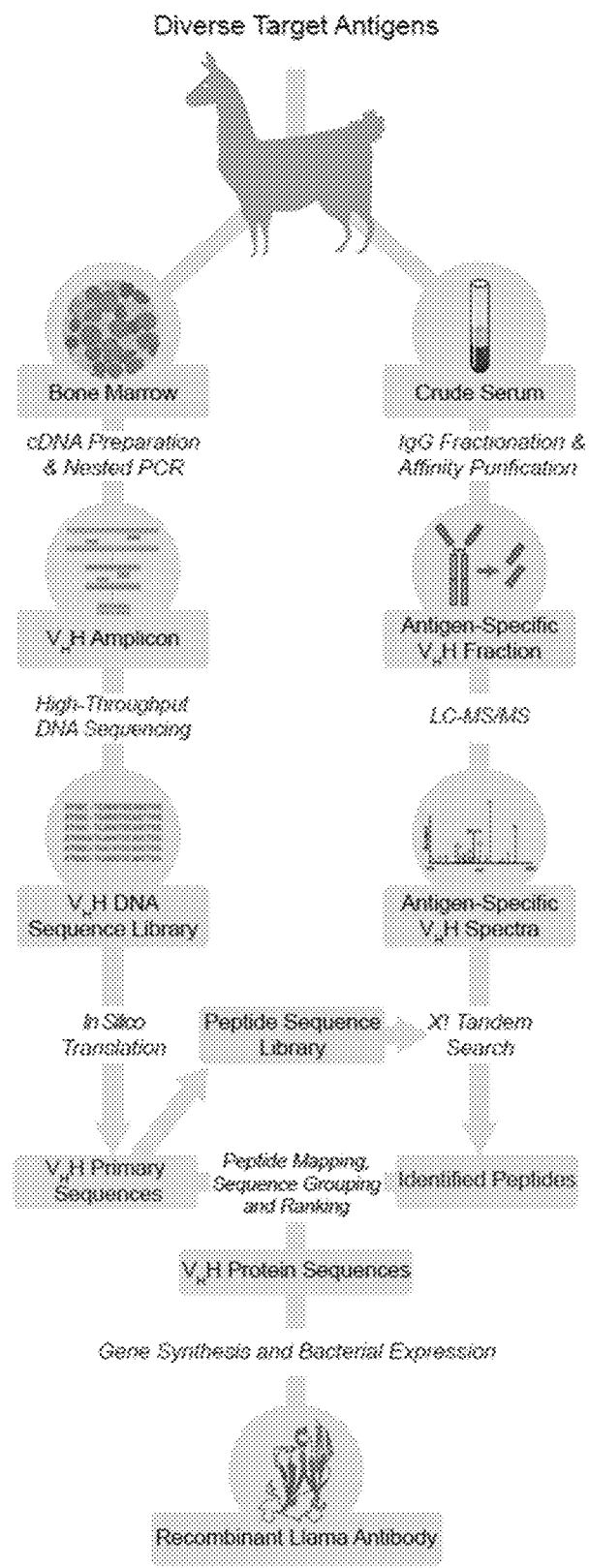
FIG. 1. Overview of nanobody identification and production pipeline. After llama immunization, cDNA from bone marrow aspirates is used for PCR amplification of the heavy-chain only variant variable region, which is then sequenced by high-throughput DNA sequencing. Separately, the serum-derived VHH protein fraction from the same llama is affinity-purified against the antigen of interest, then analyzed by LC-MS/MS. The MS data can then be searched against a sequence database generated from the DNA sequencing reads, allowing identification of corresponding VHH sequences. These sequences can then be codon-optimized for gene synthesis, allowing efficient bacterial expression of recombinant protein.

The present disclosure provides in various embodiments methods that are useful for generating large repertoires of readily expressible recombinant nanobodies with high affinities and specificities against a given antigen.

In general the disclosure comprises methods for identifying those regions of the antibodies produced by camelids from which nanobodies are derived, and recombinant methods for producing nanobodies that bind with specificity to the antigen(s) (Ag-specific nanobodies). The nanobodies referenced herein are a heavy chain only IgG class of antibodies (HCAbs), and thus contain heavy chain homodimers and do not contain antibody light chains. HCAbs are typically about 110 amino acids long and comprise a single variable domain ($V_HH$) and two constant domains (CH2 and CH3). The single variable domain comprises three complementarity-determining regions (CDRs).

In one aspect the method comprises the steps: i) introducing into a camelid an antigen such that a plurality of Ag-specific HCAbs is produced by the camelid; ii) testing lymphocytes obtained from the camelid to determine polynucleotide sequences encoding the variable region ($V_HH$) of a mixed population of HCAbs that includes the plurality of Ag-specific HCAbs as well as HCAbs that are not specific for the antigen (non-specific HCAbs), and deducing the amino acid sequences of the $V_HH$ regions of the HCAbs in the mixed population from the polynucleotide sequences; iii) processing a sample from the camelid to separate Ag-specific HCAbs from non-specific HCAbs and determining the amino acid sequences of at least a portion of the $V_HH$ regions of the Ag-specific HCAbs; and iv) comparing deduced amino acid sequences of ii) with amino acid sequences of iii) to identify amino acid sequences of ii) that are the same as the amino acid sequences of iii), thereby identifying the Ag-specific $V_HH$ regions that are members of the mixed population of HCAbs. In embodiments, the disclosure includes providing recombinant expression vectors which encode polypeptides that comprise the Ag-specific $V_HH$ regions from members of the mixed population of HCAbs, in vitro cell cultures which comprise such expression vectors, methods of making such expression vectors and cell cultures, and methods of producing polypeptides which comprise the Ag-specific $V_HH$ regions.

It is expected that any camelid, meaning any member of the biological family Camelidae, can be used to generate the HCAbs described herein. In embodiments, the camelid is selected from camels, alpacas and llamas.

We demonstrate various embodiments of the present disclosure using illustrative examples. These examples include but are not limited to recombinant production of a repertoire of 25 unique nanobodies that were initially identified by immunizing a llama with green fluorescent protein (GFP). The nanobodies exhibit $K_d$ values into the sub-nanomolar range. By utilizing the diversity of this nanobody population and mapping their binding epitopes, we were also able to design ultra-high affinity dimeric nanobodies, with $K_d$s down to ~30 pM. It will thus be recognized by those skilled in the art that aspects of the present disclosure are suitable for production of high affinity capture reagents for a multitude of biomedical applications. It is expected that various aspects of the disclosure will produce compositions that are useful for prophylaxis and/or therapy of disorders that are associated with the presence of one or more antigens, as well as for use in various diagnostic and medical imaging techniques.

The methods of this disclosure can be used to produce, identify, clone and express HCAbs that are specific for any antigen that can stimulate HCAb production in a camelid. In embodiments, the antigen is a protein or peptide antigen. In embodiments, the antigen is a polysaccharide or nucleic acid, or their derivatives. In an embodiment the antigen is any molecule, compound or composition that can stimulate antibody production. In embodiments, the antigen is a cell surface receptor. In embodiments, more than one antigen can be introduced, resulting in production of a diverse ensemble of HCAbs. In embodiments, the antigen(s) which is used to the stimulate the HCAbs can be expressed by any cell type, or by a virus. In embodiments, the antigen is expressed by a cancer cell, or by an infectious agent, such as an infectious microbe that is associated with infections in humans, or non-human animals, or both. In embodiments the antigen is a component of or is an allergen. In embodiments the antigen is component of or is a toxin. In embodiments the antigen is a component of a tag used to purify fusion proteins which comprise the tag. In an embodiment the antigen is a receptor, such as a cell surface receptor. The antigen may be well characterized, or may be unknown, such as by being part of a multimeric complex, so long as the complex can be used to capture complex-specific HCAbs as generally outlined above and according to various embodiments of this disclosure. Crude mixtures, including but not necessarily limited to cell lysates and other mixtures, could also be used provided the antigen is ultimately determined and used according to the methods of this disclosure to identify $V_HH$ regions.

In order to stimulate production of the HCAbs, the antigen or a composition comprising it can be introduced into the camelid using any suitable technique. Some non-limiting examples include oral, parenteral, subcutaneous, intraperitoneal, intrapulmonary, and intranasal. Parenteral infusions include intramuscular, intravenous, intraarterial, intraperitoneal, and subcutaneous administration. The administration can include more than one antigen if desired, meaning distinct antigens, peptides, proteins, and/or carbohydrate antigens can be administered. The composition comprising the antigen can include other components, such as pharmaceutically/veterinarially acceptable carriers, and adjuvants. In particular embodiments described herein and used to demonstrate aspects of this disclosure, animals were immunized with 5 mg of antigen, prepared with Complete Freund's Adjuvant. This was followed by three booster immunizations of 5 mg of antigen, prepared with Incomplete Freund's Adjuvant. Booster immunizations were performed 21, 42, and 62 days after the first immunization. Immunizations could alternatively be performed with smaller amounts of antigen, from 0.1 mg to 5 mg. Test serum bleeds were obtained 52 days after the first immunization, and the animal's immune response was assessed by determining the specific activity of this serum against the antigen. A production serum bleed and bone marrow aspirate were obtained 74 days after initial immunization.

Once the camelid has produced Ag-specific HCAbs, samples are obtained for analysis as generally outlined above. For use in determining sequences encoding the non-specific and Ag-specific HCAbs the sample can comprise any lymphocytes that comprise DNA sequences encoding the HCAbs. In embodiments, the sample comprises plasma cells, (i.e., plasma B cells). In embodiments, the sample comprises a biological sample from the camelid from which lymphocytes can used directly and/or can be separated. In embodiments the biological sample is a liquid biological sample. It will be recognized that any sample, including liquid biological samples that comprise the lymphocytes, can be used, and any suitable method for separating the lymphocytes (if desired) for use in the methods of the disclosure can be implemented. In non-limiting embodiments, the lymphocytes can be separated from and/or used as a component of fractionated blood, or they can be separated by affinity isolation, or they can be separated by techniques such as cell sorting, including but not necessarily limited fluorescence-activated cell sorting. In embodiments, the sample comprises bone marrow. In embodiments, the sample comprises or consists of a bone marrow aspirate. In embodiments, the sample comprises mononuclear cells that are separated from a bone marrow sample to provide a cell composition that is enriched for plasma cells.

In embodiments, the lymphocytes are processed to separate mRNA or total RNA for use in generating a cDNA library. As is well known in the art, generating a cDNA library comprises reverse transcription of the RNA to obtain DNA templates from which the $V_HH$ variable regions encoding the plurality of Ag-specific HCAbs as well as the non-specific HCAbs are amplified. The cDNA library can be produced using any suitable techniques. In embodiments, a nested PCR approach is used to amplify the plurality of Ag-specific and non-specific HCAbs. In embodiments, the cDNA library comprises as many as $10^7$ unique $V_HH$ coding sequences. The DNA sequences of the PCR amplicons from the cDNA library are then determined using any suitable technique. In general, high-throughput DNA sequencing methods are used, such as so-called deep sequencing, massively parallel sequencing and next generation sequencing, which are well known techniques and are offered commercially by a number of vendors. In embodiments, the amplified cDNAs are sequenced by high-throughput 454 sequencing or MiSeq sequencing. In embodiments, the high-throughput sequencing results in 80,000 to 5,000,000 unique reads. Determining the sequences in this manner provides a catalog of sequences encoding the $V_HH$ variable regions of the Ag-specific and non-specific HCAbs. From this catalog, the amino acid sequences of these $V_HH$ variable regions are deduced (translated in silico), thus providing a catalog of $V_HH$ variable regions, some of which are specific for one or more epitopes present the antigen administered to the camelid, and many of which are not specific for the antigen. In embodiments, the translated reads can be subjected to computational analysis, which can include but is not necessarily limited to in silico protease digestion, the results of which can be stored in a text file or indexed in a searchable peptide database stored on a computer or other digitized media. The text file or searchable database can be configured to account for a variety of parameters, such as the distinct sequences of in silico digested peptides, the number of cDNA sequencing reads that relate to each of those peptides sequences, and the sequences of the complementarity determining regions (CDR1, CDR2 and CDR3), and the framework regions if desired.

In order to determine distinct $V_HH$ variable region sequences that are responsible for specificity for the antigen, a sample from the camelid is processed to separate Ag-specific HCAbs from non-specific HCAbs. In general any suitable sample comprising HCAbs can be used for this purpose. In embodiments, one or a series of serum samples is obtained and processed, for example, to obtain an IgG fraction, such as a fraction that is enriched for $V_HH$ IgG. In embodiments, sequential purification of serum over immobilized Protein G and Protein A, with selective elution at pH 3.5 to 4.0, results in separation of $V_HH$ IgG that comprises Ag-specific and non-specific IgG components. The $V_HH$ IgG is then processed using an affinity purification approach, which involves use of the immunizing antigen as a capture agent.

Any suitable affinity capture approach can be used and will generally comprise fixing the antigen to a solid substrate, such as a bead or other material, and mixing the Ag-specific HCAbs and non-specific HCAbs (i.e., separated $V_HH$ IgG) with the substrate-fixed antigen such that only the Ag-specific HCAbs are retained on the substrate-fixed antigen. This process yields a composition comprising Ag-specific HCAbs reversibly and non-covalently bound to the substrate-fixed antigen. In embodiments, the antigen-specific HCAbs can be treated to remove the Fc portion, such as by exposure to papain, which consequently provides a composition that is enriched with antigen-specific $V_HH$ fragments bound to the capture agent. The $V_HH$ fragments can be eluted from the capture agent and purified if desired using any suitable approach. Thus, a composition comprising isolated and/or purified $V_HH$ fragments is provided for amino acid sequence analysis. Further, while papain digestion is a functional option, it sometimes produces variable results that result from using a protease digestion step, such as with batch variation in the protease, differential sensitivity, and the like. However, we have determined that, because mass spectrometry has the necessary sensitivity, dynamic range and specificity, the protease digestion step can avoided if desired, and mass spectrometry used instead to directly identify the specific separated $V_HH$ IgGs.

The amino acid sequence analysis of the $V_HH$ fragments can be performed using any appropriate technique. In an embodiment, mass spectrometric (MS) analysis of the Ag-specific $V_HH$ regions is performed and is interpreted such that the CDR sequences or portions thereof are determined. In an embodiment, a computer/microprocessor implemented comparison of the amino acid sequences determined from the Ag-specific $V_HH$ regions and the amino acid sequences deduced from the cDNA analysis is performed so that matching sequences can be identified, thus identifying Ag-specific $V_HH$ amino acid sequences. In another embodiment, the tandem mass spectra of the Ag-specific $V_HH$ regions are compared to calculated fragment masses of the amino acid sequences deduced from the cDNA analysis. In embodiments, this comparison can include data and rankings related to the MS coverage of complementarity determining regions, which in embodiments includes all of CDR1, CDR2 and CDR3 sequences, mass spectral counts, and expectation values of peptide sequences that match the cDNA and MS sequence data. Based on this analysis, the sequence of Ag-specific $V_HH$ regions can be identified.

Once the amino acid sequence of Ag-specific $V_HH$ regions are in hand they can be introduced into expression vectors so that Ag-specific HCAbs can be made recombinantly for further testing, or for use in a wide variety of other methods. In this regard, any suitable expression vector and protein expression system can be used. The expression vector is not particularly limiting other than by a requirement for the Ag-specific HCAb to be driven from a suitable promoter, and many suitable expression vectors and systems are commercially available. In embodiments the expression systems can be eukaryotic or prokaryotic expression systems, such as bacterial, yeast, mammalian, plant and insect expression systems. In general the expression vector will include at least one promoter driving expression of the HCAbs mRNA from its gene, and may include other regulatory elements to effect and/or optimize expression of the inserted HCAb coding region. The promoter can be a constitutive or inducible promoter. Suitable expression vectors can thus comprise prokaryotic and/or eukaryotic promoters, enhancer elements, origins of replication, selectable markers for use in maintaining the expression vectors in the desired cell type, polycloning sites, and may encode such features as visually detectable markers. More than one promoter can be included, and more than one HCAb can be encoded by any particular expression vector, if desired. The expression vectors can also be adapted to express HCAb-fusion proteins. The fusion proteins can include any other amino acid sequence that would be desirable for expressing in the same open reading frame as the HCAb. The HCAb sequence can be configured N-terminal or C-terminal to the fused open reading frame, depending on the particular fusion protein to be produced. In one embodiment, the protein expression is a bacterial system. In embodiments, the Ag-specific HCAbs identified and produced recombinantly according to this disclosure can exhibit a Kd in a sub-micromolar range, such as a nM range. All cDNA sequences encoding HCAbs identified by the methods of this disclosure are encompassed within its scope. The polynucleotide sequence encoding the Ag-specific HCAbs can be optimized, such as by optimizing the codon usage for the particular expression system to be used. Further, and as described briefly above, the Ag-specific HCAb protein that is expressed can be configured such that it is a component of a fusion protein. Such fusion proteins can include components for use in facilitating purification of the Ag-specific HCAb from the expression system, such as a HIS or FLAG tag, or can be designed to impart additional function to the HCAb, such as by providing a detectable label or cytotoxic moiety, or to improve solubility, secretion, or any other function. In various embodiments, the Ag-specific HCAbs and/or fragments can be conjugated to a chemotherapeutic agent to enable localization of the chemotherapeutic agent to cells which express the antigen. Chemotherapeutic agents useful in the generation of such Ag-specific HCAbs conjugates include but are not necessarily limited to enzymatically active toxins and fragments thereof. In another embodiment, the Ag-specific HCAbs and/or fragments thereof may be conjugated to a detectable label, such as a radioactive agent or a fluorescent moiety, for use in labeling cells or tissues in medical imaging techniques, or for targeted killing of cells which express the antigen. In embodiments, any of variety of radioactive isotopes are available for conjugating to Ag-specific HCAbs such that cells to which the Ag-specific HCAbs bind may be imaged or selectively destroyed. For selective destruction of cells expressing the antigen, the Ag-specific HCAbs that recognize the antigen can be conjugated to a highly radioactive atom, such as $In^{111}$, $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the Ag-specific HCAbs and/or fragments thereof are used for identifying cells expressing the antigen they can comprise comprise a radioactive atom for scintigraphic studies, for example $Tc^{99m}$ (metastable technetium-99), $I^{123}$, or a spin label for nuclear magnetic resonance (NMR) imaging (also known as magnetic resonance imaging, or "MRI"), such as $I^{123}$, $I^{131}$, $I^{124}$, $F^{19}$, $C^{13}$, $N^{15}$, $O^{17}$ or Gadolinium (III) or Manganese (II).

In embodiments, the Ag-specific HCAbs can be partially or fully humanized for use in prophylaxis and/or therapy of a condition that is positively associated with the presence of the antigen. In general, humanization involves replacing all or some of the camelid derived framework and constant regions of Ag-specific HCAbs with human counterpart sequence, with the aim being to reduce immunogenicity of the Ag-specific HCAbs in therapeutic applications. In some instances, the FR residues of the human immunoglobulin are replaced by corresponding non-human residues. In general, a humanized Ag-specific HCAb will comprise substantially all of at least one, and typically two, variable domains, in which all or substantially all of the hypervariable loops correspond to those of the non-human, camelid immunoglobulin and all or substantially all of the FRs are those of a human immunoglobulin sequence.

In embodiments, the disclosure includes making HCAb heterodimers. For example, a single HCAb heterodimer can have specificity for two distinct epitopes on the antigen, or it could have specificity for distinct epitopes on two different antigens. After identification, two or more such HCAb candidates can be genetically fused, joined with a peptide linker sequence, and joined to form multimers, including but not necessarily limited to trimers, tretramers, and oligomers having more than four HCAb members.

In another aspect, the disclosure includes use of HCAbs generated as described herein to map epitopes on the antigen that was used to raise the HCAb in the camelid. This aspect comprises binding one or more distinct HCAbs to the antigen and determining the location of the HCAb binding on the antigen, thereby identifying the epitope or amino acids which are comprised by the epitope. In embodiments the location of the HCAb can be determined by NMR. Epitope mapping provided by the disclosure are useful for instance, for determining fragments of antigens that comprise epitopes that are particularly effective in stimulating an antibody response, and accordingly could be used to generate a robust antibody response in a human or non-human animal, thereby providing optimal vaccine candidates.

This disclosure encompasses each and every amino acid sequence described herein, and each and every polynucleotide encoding the amino acid sequences. The amino acid sequences include fragments of at least 4, 5, 6, 7, 8, 9, 10, 11, 12, 13, 14, or 15, or more, contiguous amino acids of any amino acid sequence disclosed herein. In embodiments the disclosure encompasses amino acid fragments that comprise or consist of one or more complementarity determining regions (CDRs). Recombinant expression vectors encoding one or more polypeptides comprising or consisting of one or more of the CDRs are included in the disclosure. Any suitable expression vector can be used for such expression and many are known in the art and/or are commercially available and can be adapted for use according to the instant disclosure. The disclosure includes cells and cell cultures comprising the expression vectors, methods of making such cells and cell cultures comprising introducing such an expression vector into cells, methods of producing nanobodies or antigen-binding fragments thereof by allowing expression of the expression vector in the cells and separating the nanobodies or fragment thereof from the cells. The disclosure includes isolated nanobodies and antigen-binding fragments thereof, and modified nanobodies and antigen-binding fragments thereof, such as fusion proteins and protein conjugates, wherein the nanobodies and antigen-binding fragments are covalently attached to a chemical moiety. The disclosure also includes one or more cDNAs encoding the nanobodies or antigen-binding fragments thereof.

The following Example is presented to illustrate the embodiments of the disclosure. It is not intended to be limiting in any manner.

Example

Strategy for Nanobody Identification

Our approach to nanobody discovery centers on bottom-up MS identification of affinity-purified $V_HH$ antibodies isolated from an individual llama, in correlation with a DNA sequence database generated from the same animal (FIG. 1). Our approach represents a novel pipeline for nanobody production where each stage has been highly optimized.

After a series of standard immunizations, we collect both serum samples and bone marrow aspirates (FIG. 1). Plasma cells are enriched in marrow aspirates compared to blood. They produce high affinity antibodies and express elevated levels of immunoglobulin RNA and therefore are a superior source for generating cDNA libraries. Importantly, we do not create expression libraries, and thus remove the need for efficient exogenous expression, folding, and presentation of the clones; rather, we take advantage of high-throughput sequencing to produce large sequence databases from cDNA, covering the $V_HH$ variable region repertoire produced by the immunized animal. In contrast to conventional antibodies, nanobody elucidation does not require the pairing of heavy and light chains, allowing for easy generation of comprehensive sequence libraries.

In parallel, native polyclonal antigen-specific antibodies are obtained from serum isolated directly from the immunized animal. Affinity purification can be adjusted to generate fractions of antibodies with the highest affinity and specificity. We also take advantage of new advances in mass spectrometry that enable the identification of hundreds of proteins from a single sample, such as the presently considered enriched fractions of $V_HH$ antibodies (FIG. 1). We built a user-friendly MS protocol and interpretive program that allows the rapid and accurate identification of the $V_HH$ sequences. The high efficiency of this method allows us to then directly produce codon optimized nanobody expression constructs in order to enable high expression and facile purification. Finally, we use a straightforward screen to determine those recombinant nanobodies that express and bind well to the antigen.

Figure 2:
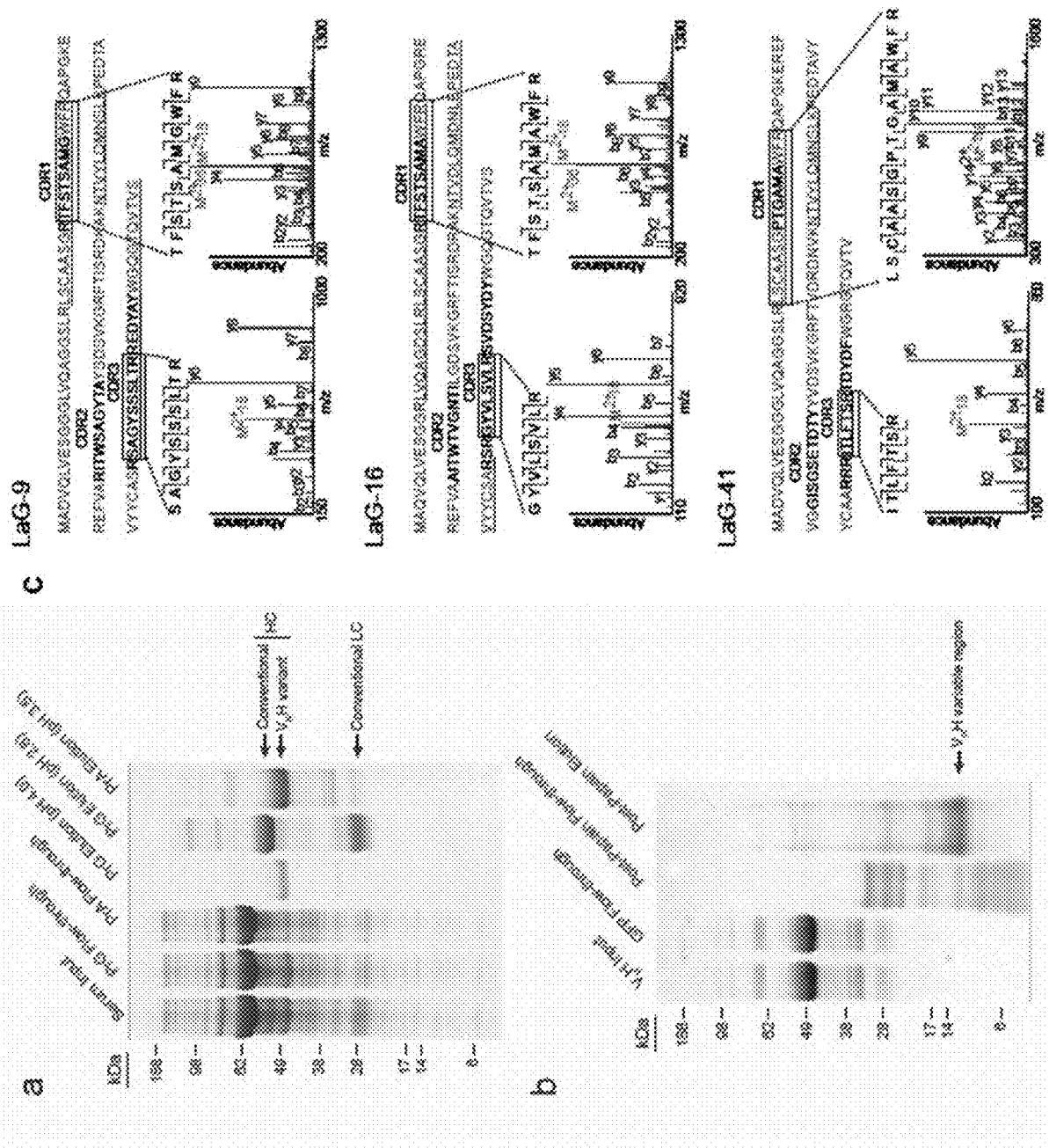
FIG. 2. Purification and mass spectrometric analysis of GFP-binding VHH IgG. (a) Llama serum fractionated by successively binding to Protein G and Protein A agarose resin. VHH variant heavy chains were specifically eluted in pH 4.0 (Protein G) and pH 3.5 (Protein A) buffers. (b) The pooled VHH fraction was bound to GFP-Sepharose resin, and washed with 3.5 M MgCl2. Bound IgG was digested on the beads with papain, releasing Fc fragments. The remaining GFP-bound VHH fragments were eluted with ammonium hydroxide. (c) Representative tandem mass spectra of identified peptides (shown boxed). Peptides were mapped to the informative CDR regions of three candidate VHH sequences, which were then chosen for production and characterization as shown in FIGS. 3 and 4. The regions of these sequences covered by MS are shown underlined. The same approach can be used with any other immunogen and is also illustrated using mCherry.
Figure 7:
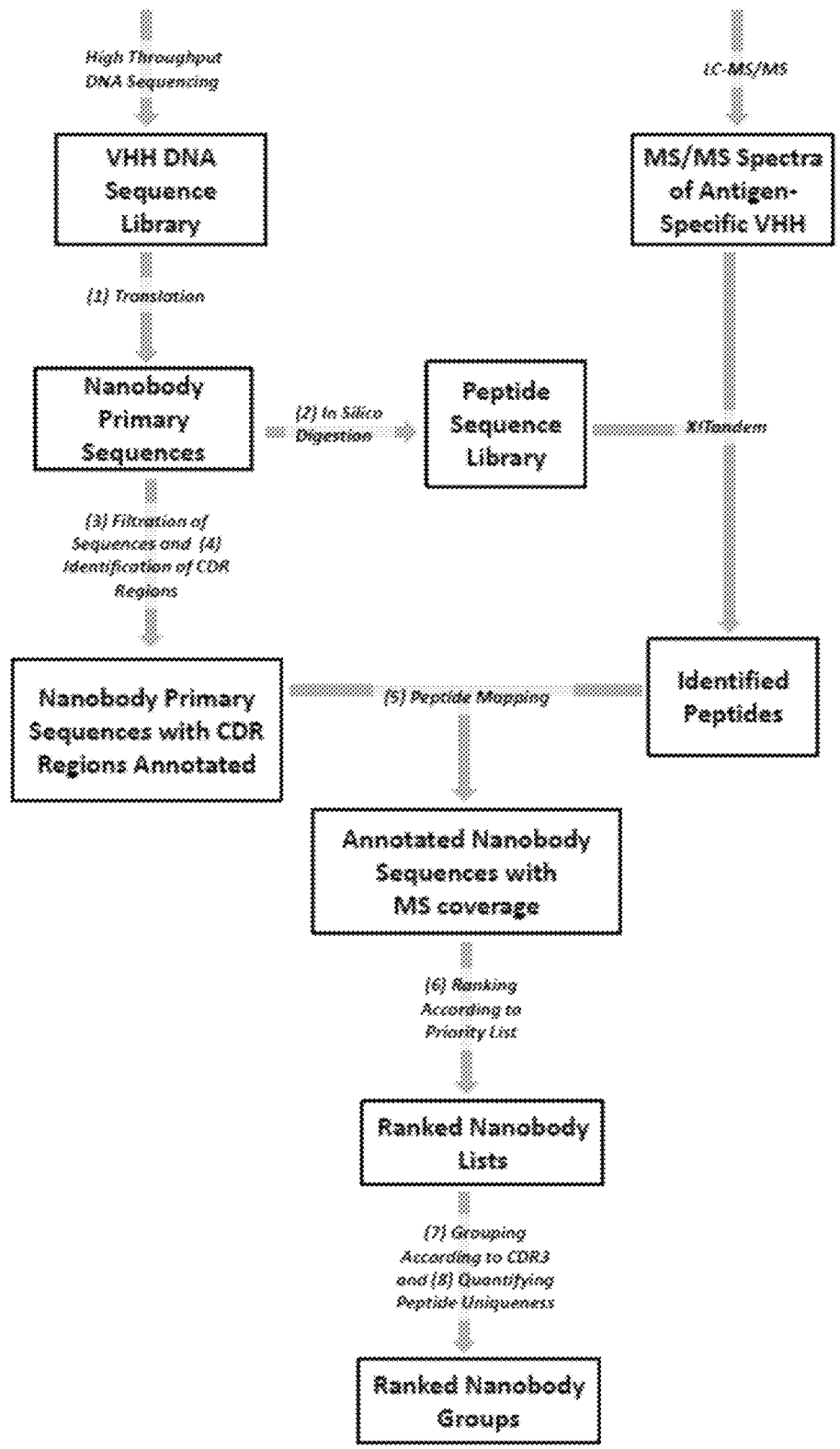
FIG. 7. Schematic overview of the analytical pipeline used to identify and nanobody sequences, starting from raw high-throughput sequence data and mass spectra.
Figure 8:
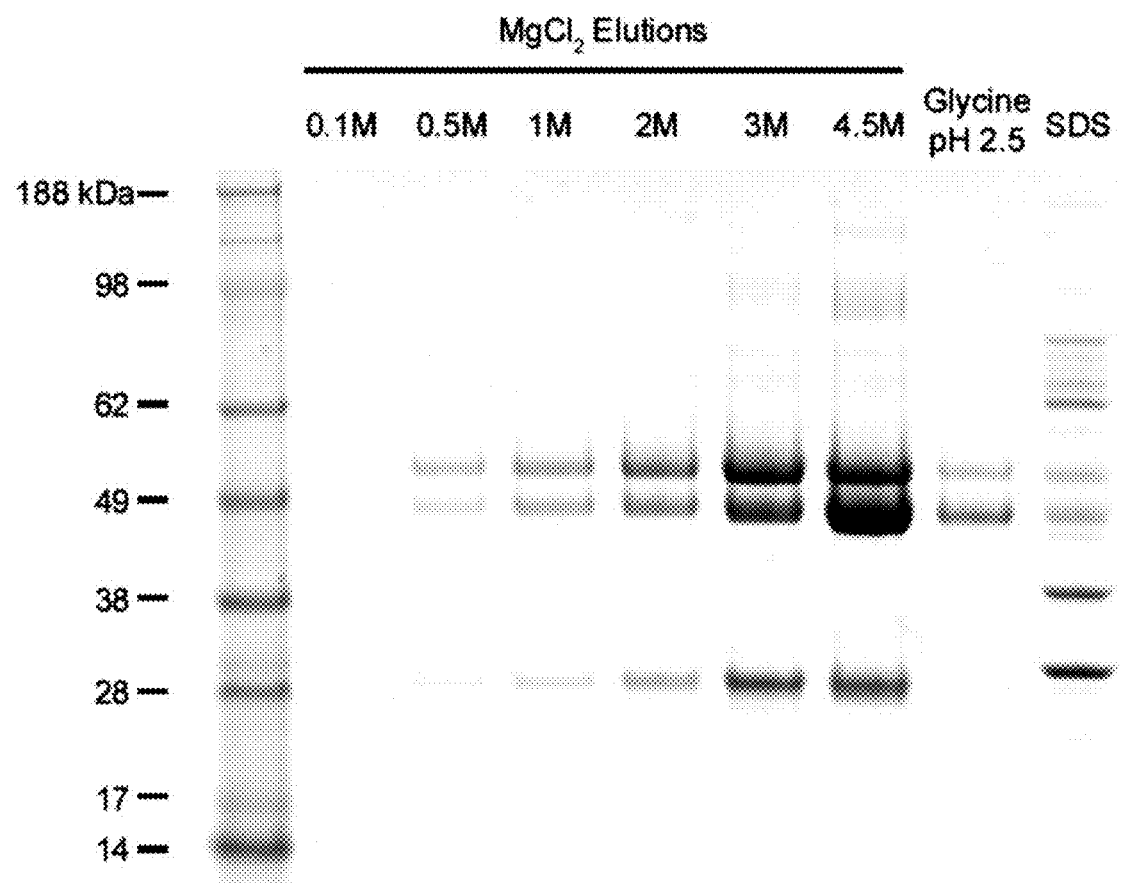
FIG. 8. The GFP affinity of serum VH and $V_HH$ IgG was assessed by resistance to high stringency $MgCl_2$ washes. A llama serum sample was bound to GFP-sepharose resin, which was then serially washed with increasing $MgCl_2$ concentrations, followed by elutions with 0.1M glycine-HCl, pH 2.5 and boiling SDS.

Testing the approach on two high utility antigens. To generate a nanobody repertoire of maximal utility, we chose the GFP and mCherry tags for our first target antigens, due to their central roles in cell biological studies and because so many cell lines and transgenic animals carry these proteins. Further, while these fluorescent proteins have a broadly similar beta barrel structure, they are in fact significantly evolutionarily divergent, being from jellyfish and coral species (separated by ~700 million years), and have only 26% sequence similarity, making for distinct immunogens[21]. After immunization of individual llamas with these antigens and confirmation of an immune response, we serially fractionated crude serum bleeds to obtain exclusively $V_HH$-containing heavy chain antibodies (FIG. 2a), taking advantage of the differential specificity of Protein A and Protein G for $V_HH$-containing heavy chain antibodies versus conventional antibodies[7]. The $V_HH$-containing heavy chain antibody fraction was then affinity purified over antigen-coupled resin, and washed with $MgCl_2$ at various stringencies, from 1 M to 3.5 M, allowing the isolation of antibodies enriched for different levels of affinity (FIG. 8). The antibodies were then digested with papain on-resin to cleave away the constant regions and leave behind the desired minimal $V_HH$ variable region fragments (FIG. 2b). Finally, the antigen-bound $V_HH$ fragments were eluted and separated by SDS-PAGE, allowing the purification of the ~15 kDa $V_HH$ fragments away from $F_{ab}$ fragments derived from contaminating conventional antibodies as well as $F_c$ fragments (both ~25 kDa), and undigested antibodies (~50 kDa) (FIG. 2b). The gel purified bands were then trypsin-digested and analyzed by liquid chromatography-MS and MS/MS (FIG. 2c). We recovered the highest affinity $V_HH$ fragments by using the highest stringency washes, which also significantly decreased the complexity of the eluted sample, aiding MS analysis when large repertoires of antibody were bound. To create an animal-specific antibody sequence database, lymphocyte mRNA samples from individual immunized llamas were obtained for high-throughput sequencing. Mononuclear cells were isolated from bone marrow aspirates, enriching for long-lived antibody secreting plasma cells[20,22,23]. Total RNA from these cells was reverse transcribed, and a nested PCR was performed to specifically amplify sequences encoding the $V_HH$ variable regions[14]. This PCR product was then sequenced by high-throughput 454 (for GFP) or MiSeq (for mCherry) sequencing, resulting in approximately 800,000 or 3,000,000 unique reads, respectively. These reads were translated, filtered and trypsin-digested in silico to create a searchable peptide database for MS analysis (FIG. 1 and FIG. 7). To illustrate one aspect of this process, for GFP cloning in a first step, CALL001 (5'-GTCCTGGCTGCTCTTCTACAAGG-3') and CALL002 (5'-GGTACGTGCTGTTGA ACTGTTCC-3') primers were used to amplify the IgG variable domain into the CH2 domain (Conrath et al, #26). The approximately 600-750 bp band from VHH variants lacking a CH1 domain was purified on an agarose gel. Next, VHH regions were specifically reamplified using framework 1- and 4-specific primers with 5' 454 adaptor sequences: 454-VHH-forward (5'-CGTATCGCCTCCCTCGCGCCATCAG ATGGCT[C/G]A[G/T]GTGCAGCTGGTGGAGTCTGG-3' (SEQ ID NO:6)) and 454-VHH-reverse (5'-CTATGCGCCTTGCCAGCCCGCTCAG GGA-GACGGTGACCTGGGT-3' (SEQ ID NO:7)). The approximately 400 bp product of this reaction was gel purified, then sequenced by high-throughput 454 sequencing, resulting in approximately 800,000 unique reads.

Figure 9:
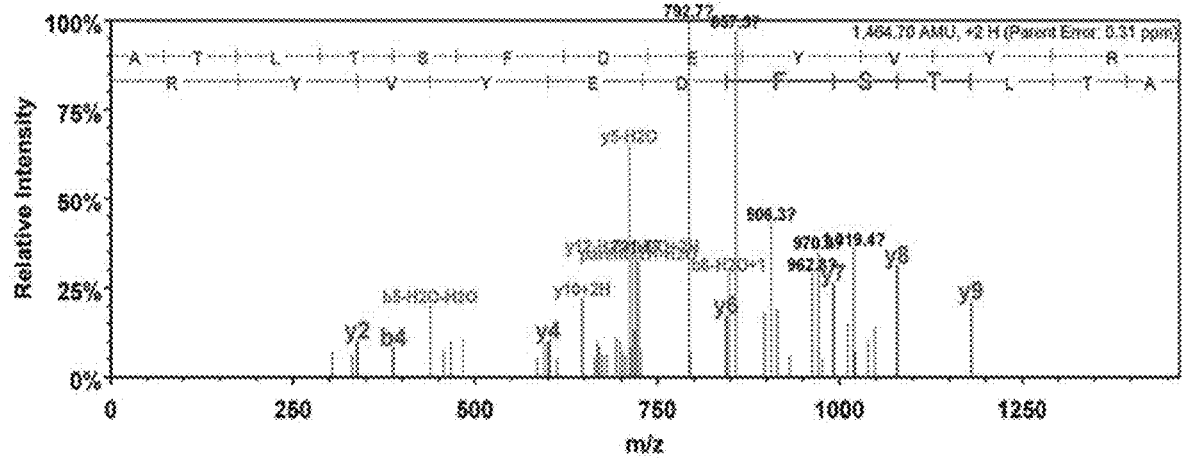
FIG. 9. Annotated tandem mass spectra of CDR3 peptides from all 25 GFP-binding LaGs. Full amino acid sequences of the identified nanobodies are shown, with regions covered by peptides underlined, and CDR regions are in lighter font. The amino acid sequences of LaG-2-LaG-35 are provided as SEQ ID NO:10-35, respectively.
Figure 9:
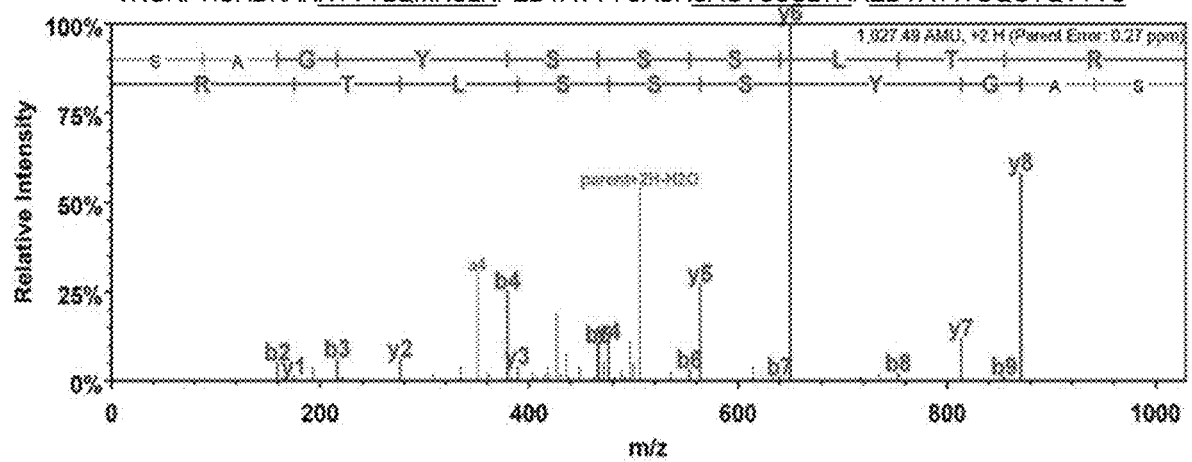
Figure 9:
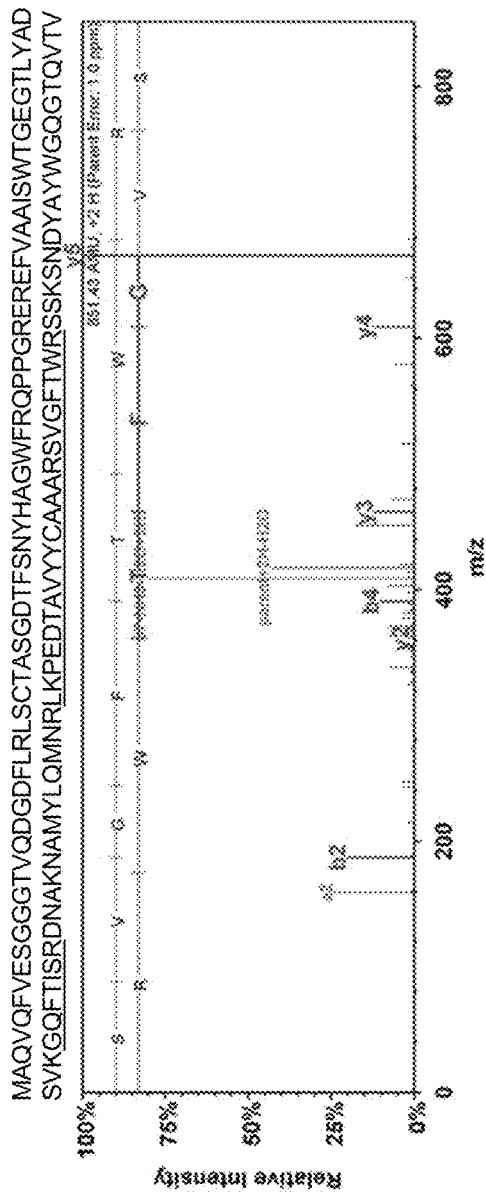
Figure 9:
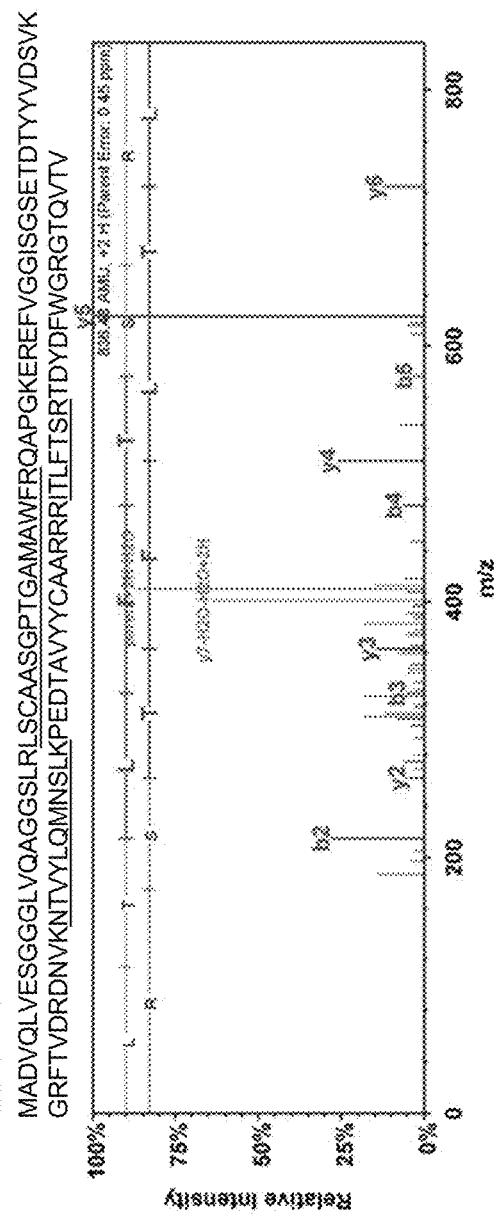

Because most proteins differ from each other throughout their sequences, they can be readily distinguished by MS-based database sequence searches. However, the identification of specific $V_HH$ sequences is more challenging because they comprise in large part highly conserved framework regions. Moreover, rather than searching well-established databases, a $V_HH$ cDNA database must be generated for each immunized animal. To deal with both challenges, we developed a bioinformatic pipeline to identify the highest probability matches from a large pool of related $V_HH$ sequences (Llama Magic software). In this pipeline, $V_HH$ sequences were ranked by a metric based on MS/MS sequence coverage of complementarity determining region 3 (CDR3, the most diverse $V_HH$ region) as well as CDR1 and CDR2 coverage, total $V_HH$ coverage, sequencing counts, mass spectral counts, and the expectation values of matched peptides (FIGS. 7 and 8). Preliminary attempts to identify $V_HH$ sequences solely by their CDR3 regions revealed that identical CDR3 sequences are frequently shared between multiple distinct $V_HH$ sequences, with diverse CDR1 and CDR2 sequences. It is likely that this is a result of somatic gene conversion, in which, after V(D)J recombination, secondary recombination occurs between upstream V gene segments and already rearranged V(D)J genes[24,25]. While this mechanism has not previously been reported in llamas, a number of mammals do exhibit such recombination, including rabbit, swine, and bovine species[26]. Our automatic ranking pipeline, coupled with careful manual inspection, overcame these issues and provided us 44 high-probability hits against GFP, classified as LaG (Llama antibody against GFP) 1-44, which we subjected to further screening (FIG. 9). As the additional test antigen, a smaller subset of eight clones was chosen for follow up (LaM 1-8) for mCherry.

Figure 6:
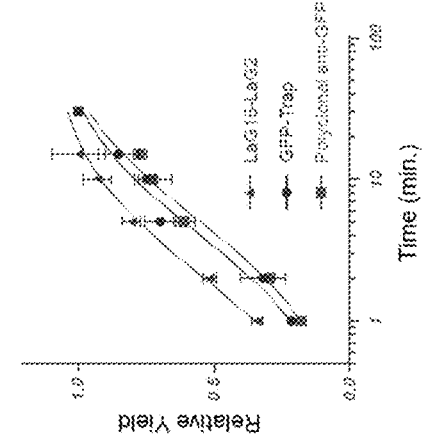
FIG. 6. LaG and LaM affinities and specificities, showing a broad range of affinities and subset of extremely tight binders in the repoertoire. (a) Characteristics of the 25 LaG clones and dimers with verified affinity for GFP. Kds for GFP binding were determined by SPR unless otherwise noted. Kds are also shown for LaG dimers fused using a glycine-rich peptide linker (3 repeats of GGGGS (SEQ ID NO:44), or G4S), or a 3.times.FLAG linker. For yeast Nup84-GFP and mammalian Rbm7-LAP affinity isolations using LaG-conjugated Dynabeads, Coomassie-stained bands from elutions separated by SDS-PAGE were quantified, and known specific and nonspecific bands were used to calculate signal to noise (S:N) ratios. Bead binding assays were used to determine affinity for variant fluorescent proteins, and divergent AmCFP binding abilities are shown. GFP epitopes were determined by NMR, and grouped into three broad classes (I-III). The number of residues identified in the binding site, and its calculated accessible surface area (ASA), are also shown. (b) Characteristics of the 6 LaM clones with verified affinity for mCherry. Kds for mCherry binding were determined by SPR. (c) Affinity isolations of yeast Nup84-GFP were performed using a LaG16-LaG2 dimer with G4S, llama polyclonal anti-GFP, or commercial GFP-Trap.RTM. nanobody. The complex was isolated at various time points, and relative yield determined by quantification of Coomassie-stained bands of known Nup84 complex components.
Figure 10:
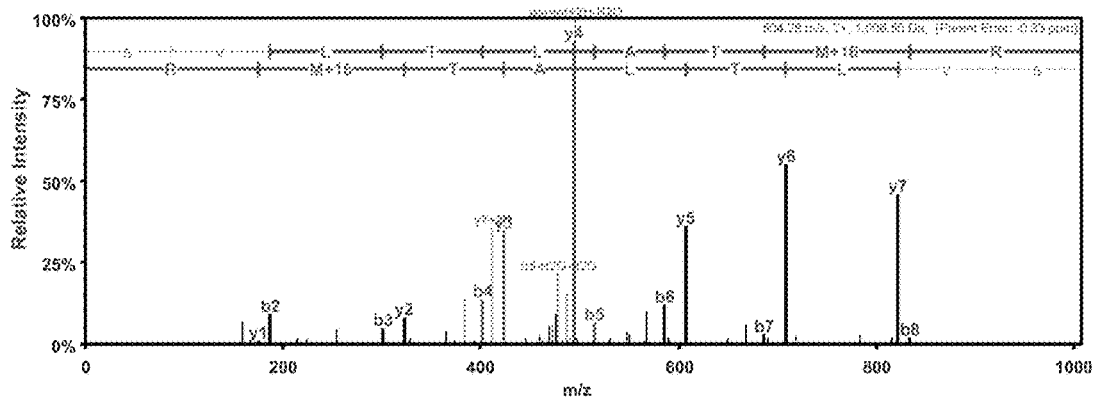
FIG. 10. Annotated tandem mass spectra of CDR3 peptides from all six mCherry-binding LaMs. Full amino acid sequences of the identified nanobodies are shown, with regions covered by peptides underlined, and CDR regions are in lighter font. The amino acid sequences of LaM-1-LaM-8 are provided as SEQ ID NO:36-41, respectively.
Figure 10:
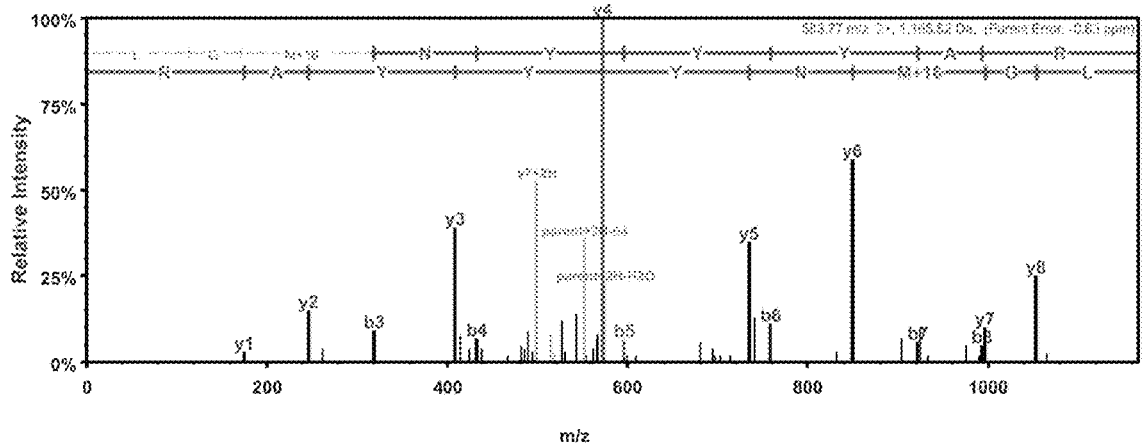
Figure 10:
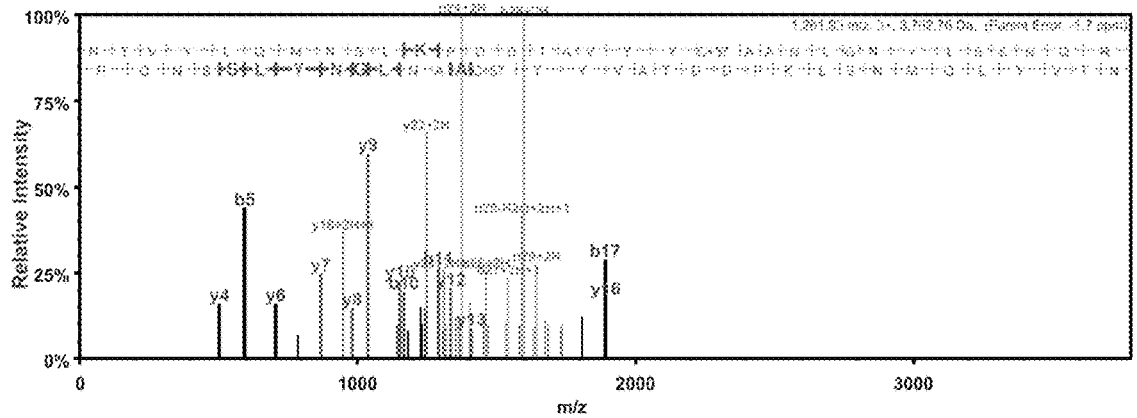
Figure 10:
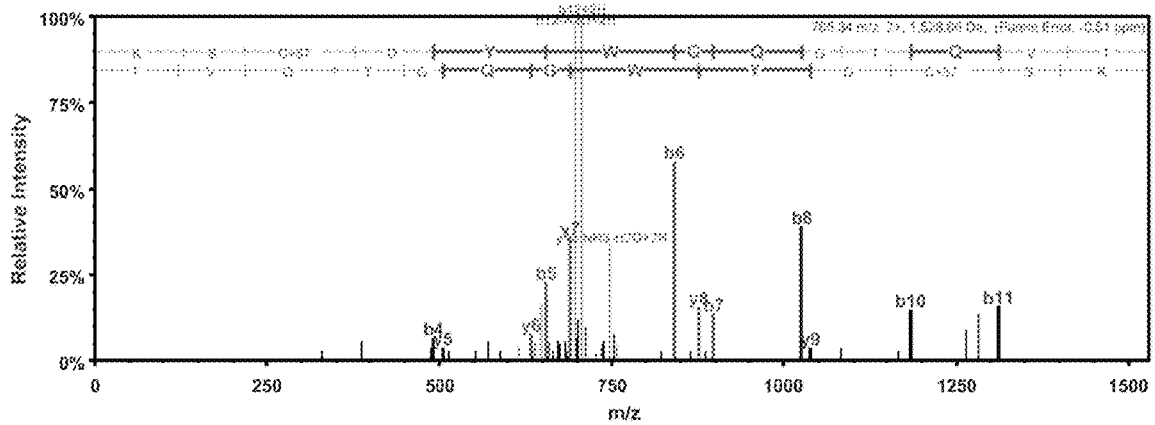
Figure 10:
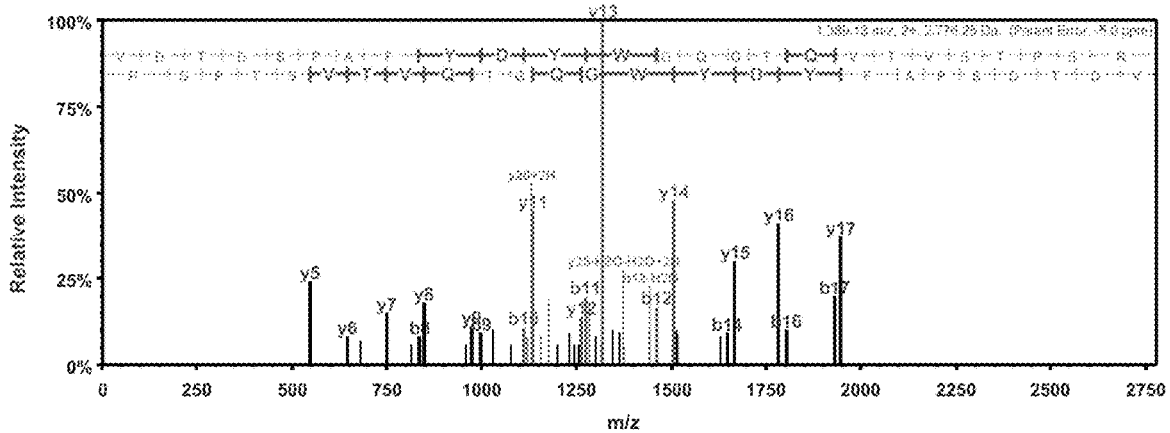
Figure 11:
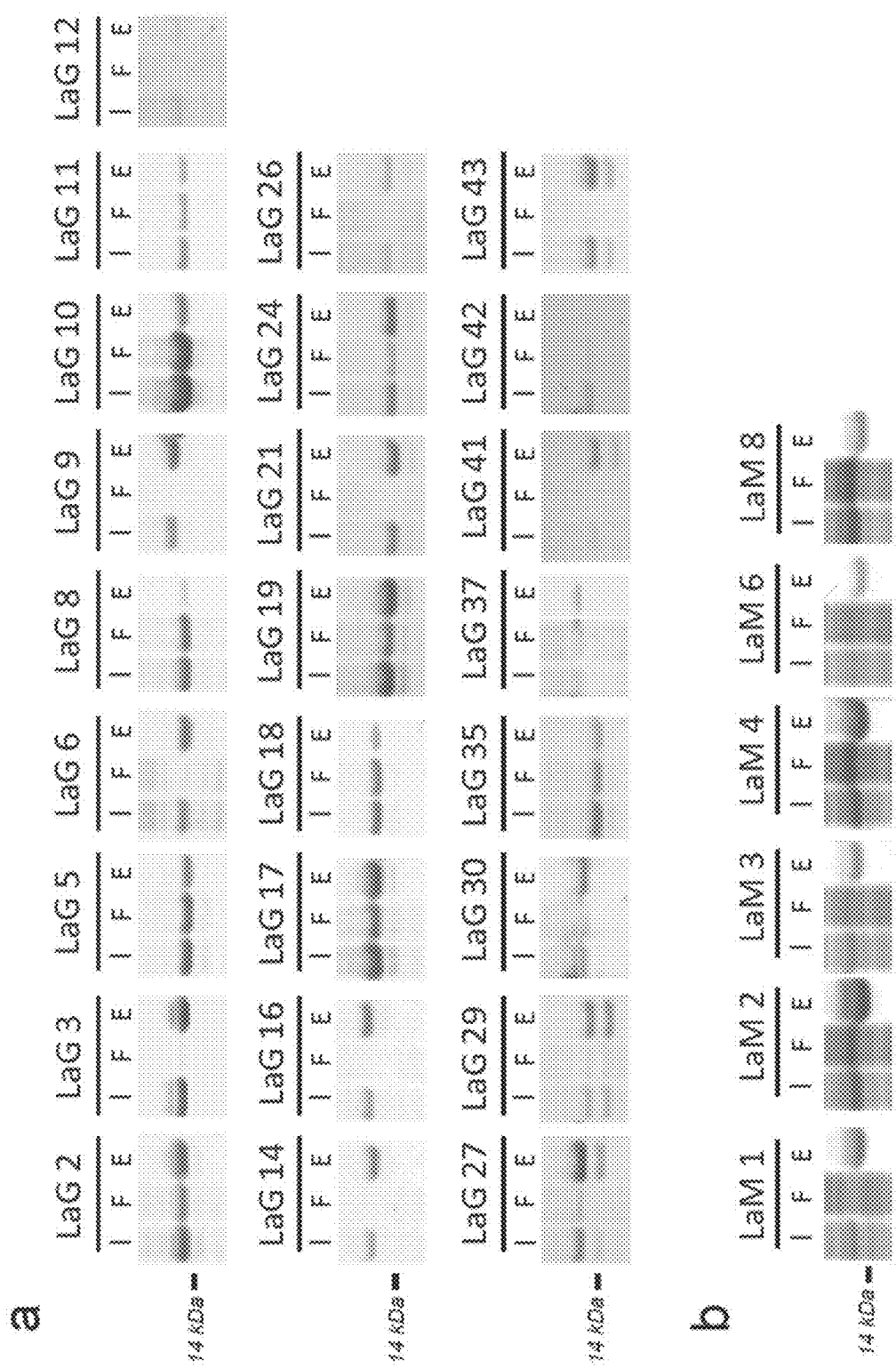
FIG. 11. To screen for GFP or mCherry binding activity, candidate (a) LaG or (b) LaM nanobodies were expressed in bacteria, and periplasmic extracts were incubated with GFP- or mCherry-conjugated sepharose. For each clone, input (I), flow-through (F), and elution (E) samples from the sepharose binding were run on SDS-PAGE, and Coomassie-stained nanobody bands are shown for the positive binders.
Figure 12:
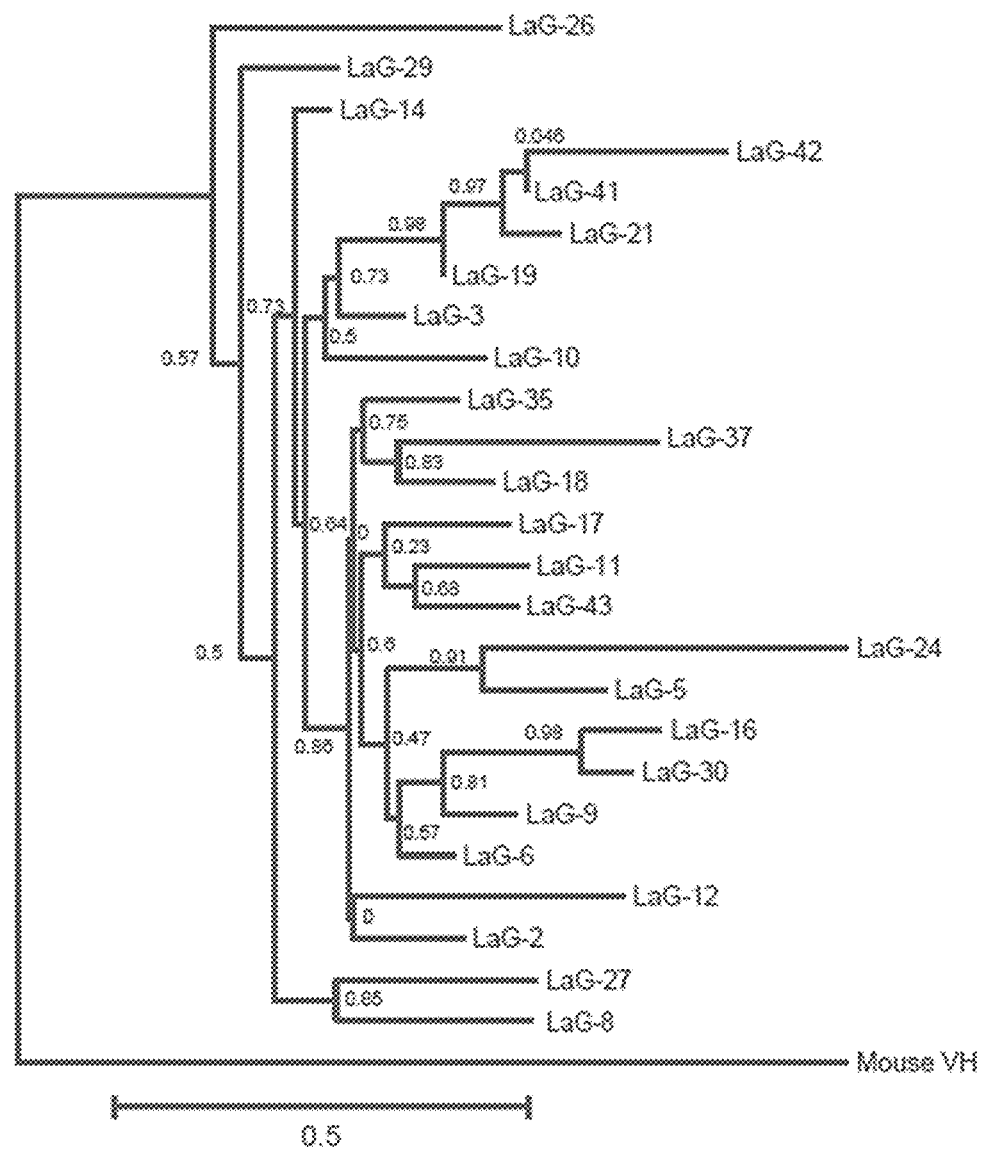
FIG. 12. Phylogenetic analysis of nanobody sequences. LaG sequences were aligned, and a phylogenetic tree was generated from LaG sequences FIG. 13. Determination of LaG $K_d$s by surface plasmon resonance (SPR). Eighteen GFP-binding LaGs were assessed for GFP affinity by SPR on a ProteOn XPR36 instrument. Three LaG fusion constructs were also assessed, with 3×FLAG or flexible gly-rich ($G_4S$) linkers. GFP was immobilized on a ProteOn sensor chip, and 4-5 concentrations of each LaG were injected. Sensorgrams from a representative injection of each LaG are shown, with corresponding protein concentrations indicated. The beginning and end of each injection are indicated by grey lines, and Langmuir binding curve fits are in black. Association ($k_a$), dissociation ($k_d$), and equilibrium ($K_D$) constants are shown.
Figure 13:
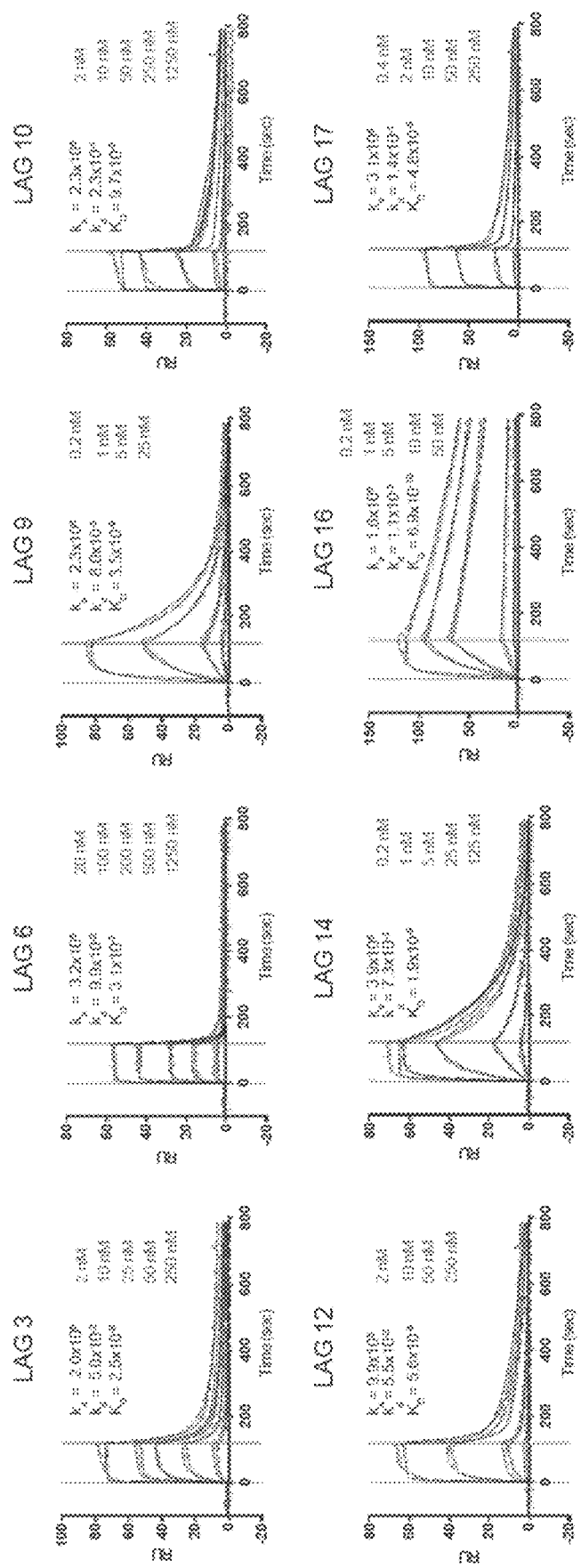
Figure 13:
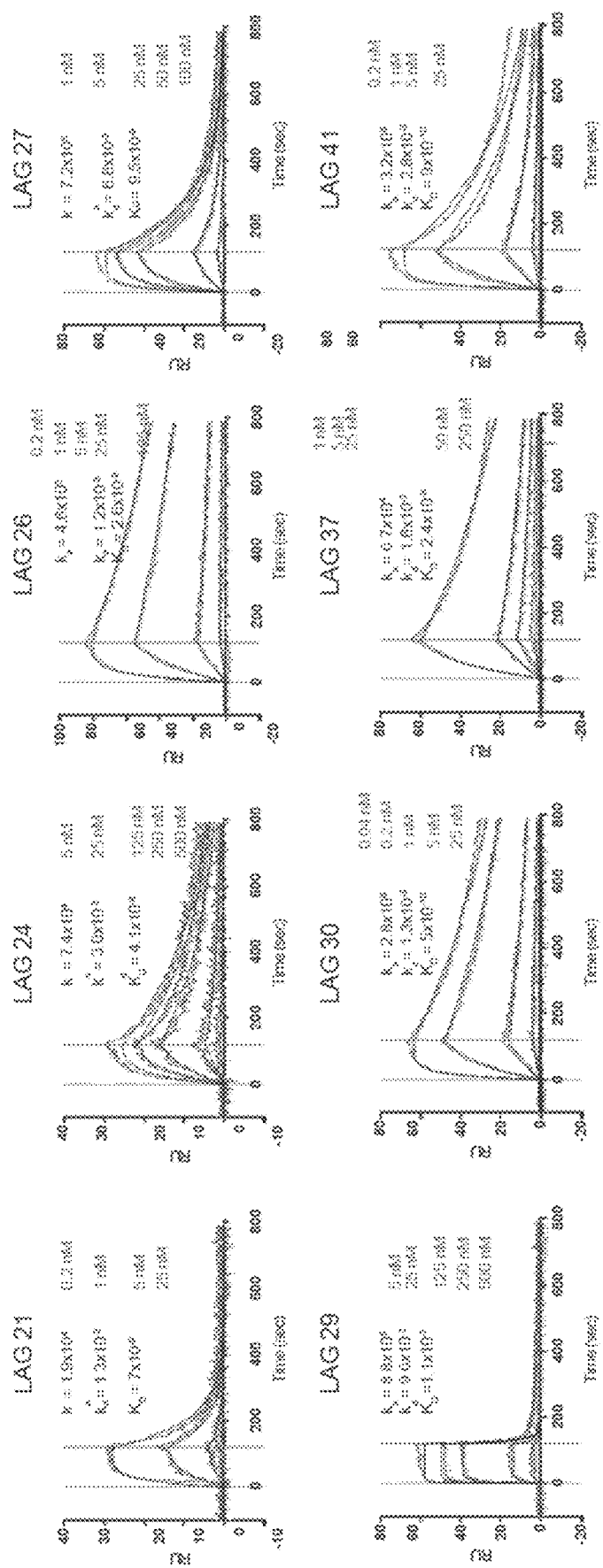
Figure 13:
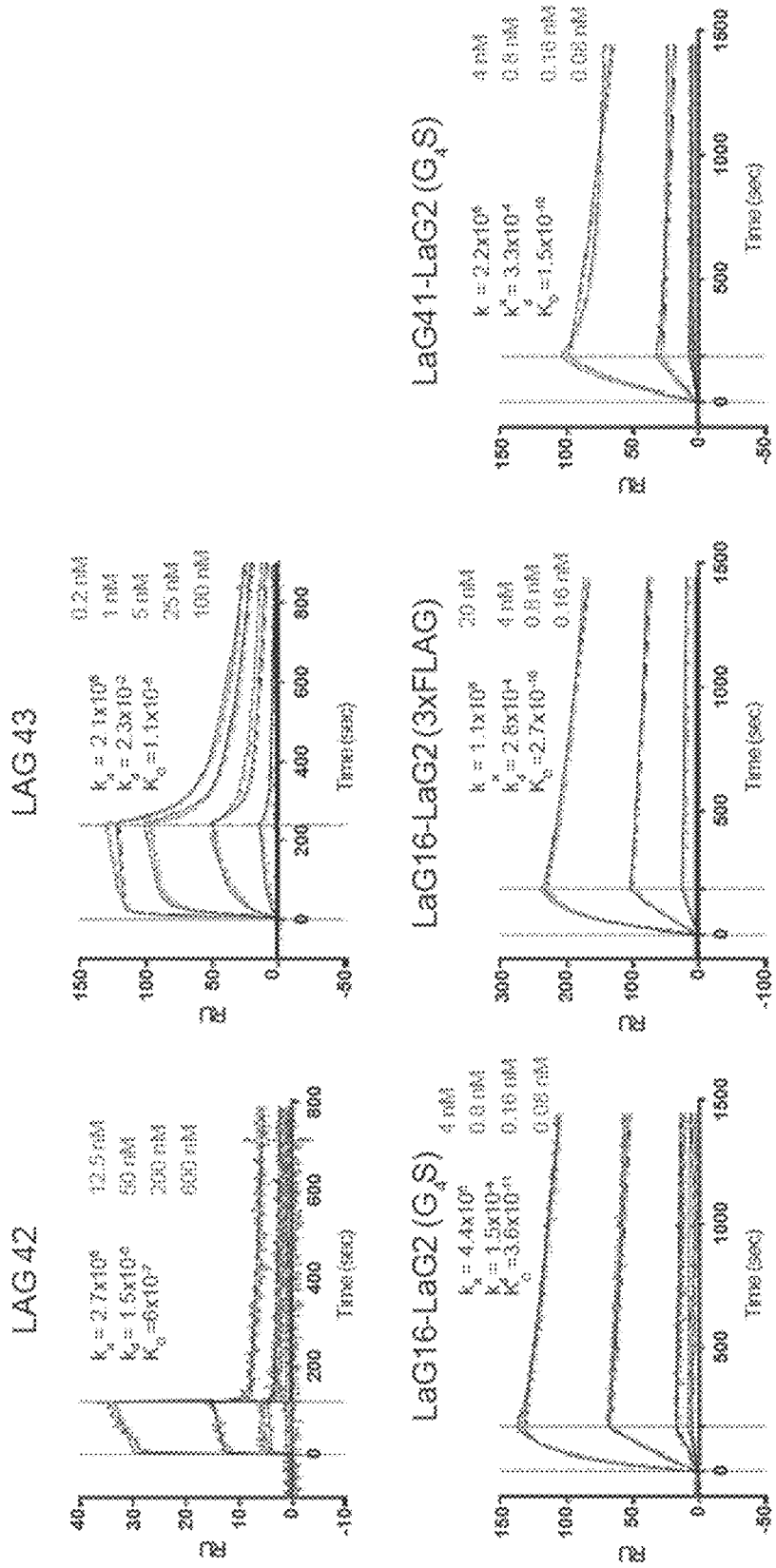
Figure 14:
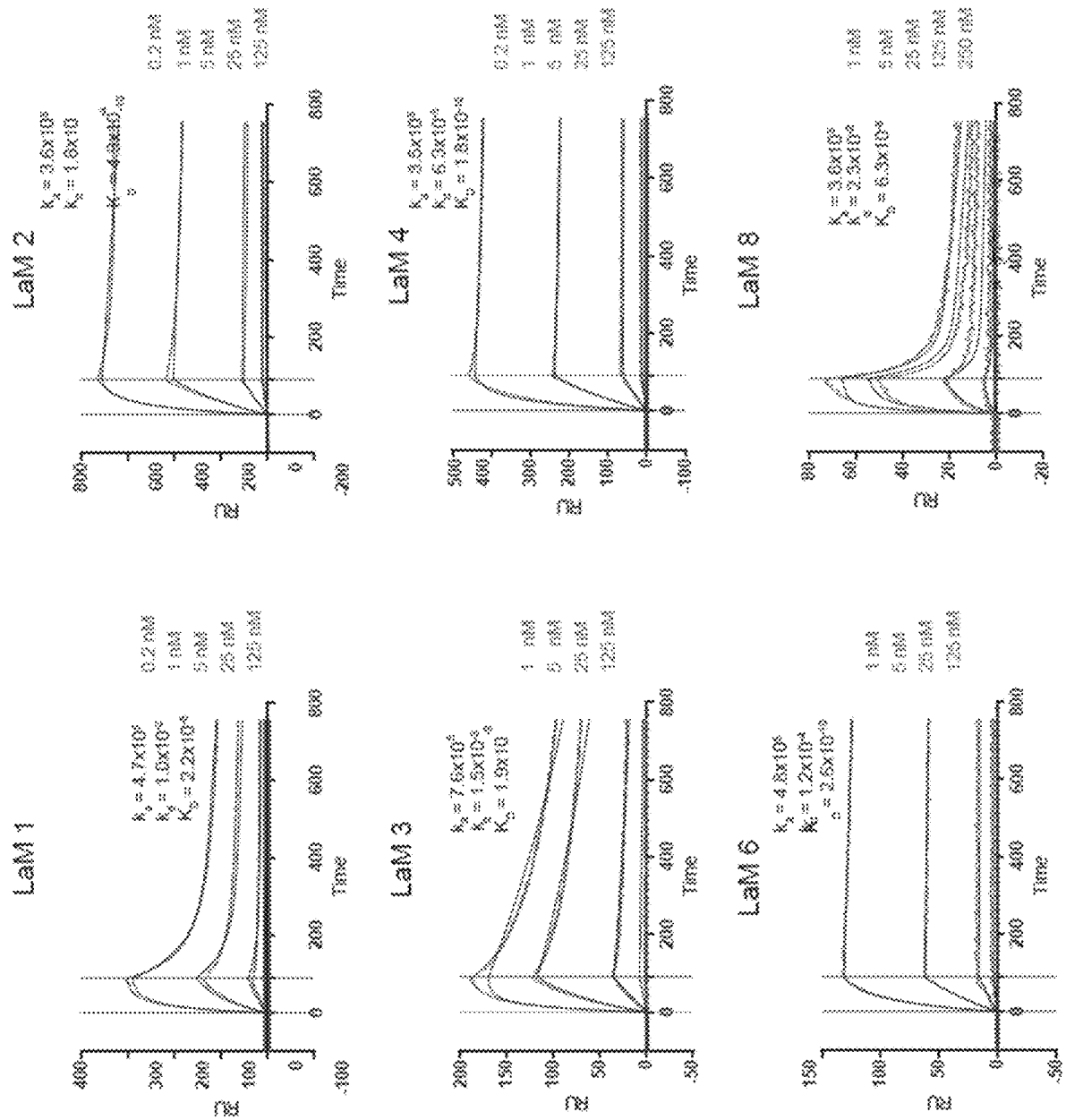
FIG. 14. SPR analysis of LaMs. SPR sensorgrams and kinetic constants are shown for LaM binding to immobilized mCherry, as in FIG. 13.

Codon optimized genes for these hits were synthesized and cloned into a bacterial expression vector. After expression, lysates were passed over antigen-coupled resin to identify nanobodies that displayed both robust expression and high, specific affinity (FIG. 10). From this pilot screen, we found 25 specific anti-GFP nanobodies out of 44 tested, and 6 anti-mCherry clones out of the 8 screened. Phylogenetic analysis of the verified nanobodies revealed significant sequence diversity among these clones (FIG. 12). While not directly analogous, the extremely high success rate of this single screening step (57-75%) is very favorable in comparison to the final panning and selection steps of phage display[12,14,27,28]. The affinity of these 25 GFP-binding nanobodies and 6 anti-mCherry nanobodies was further assessed by either surface plasmon resonance (SPR) or in vitro binding assays with immobilized nanobodies (FIGS. 13 and 14). For the larger repertoire of anti-GFP clones, these experiments revealed a wide range of affinities, with $K_d$s from 0.5 nM to over 20 μM (FIG. 6a), and identified 16 nanobodies with very high affinity binding (50 nM). Our SPR data also showed wide ranges of association and dissociation rates, indicating differences in binding kinetics (FIG. 13). As they were derived from a smaller number of high-confidence candidates, the $K_d$s of the six anti-mCherry nanobodies were consistently strong, ranging from 0.18 nM to 63 nM (FIG. 6b).

Specificity and efficacy of recombinantly produced nanobodies

Figure 3:
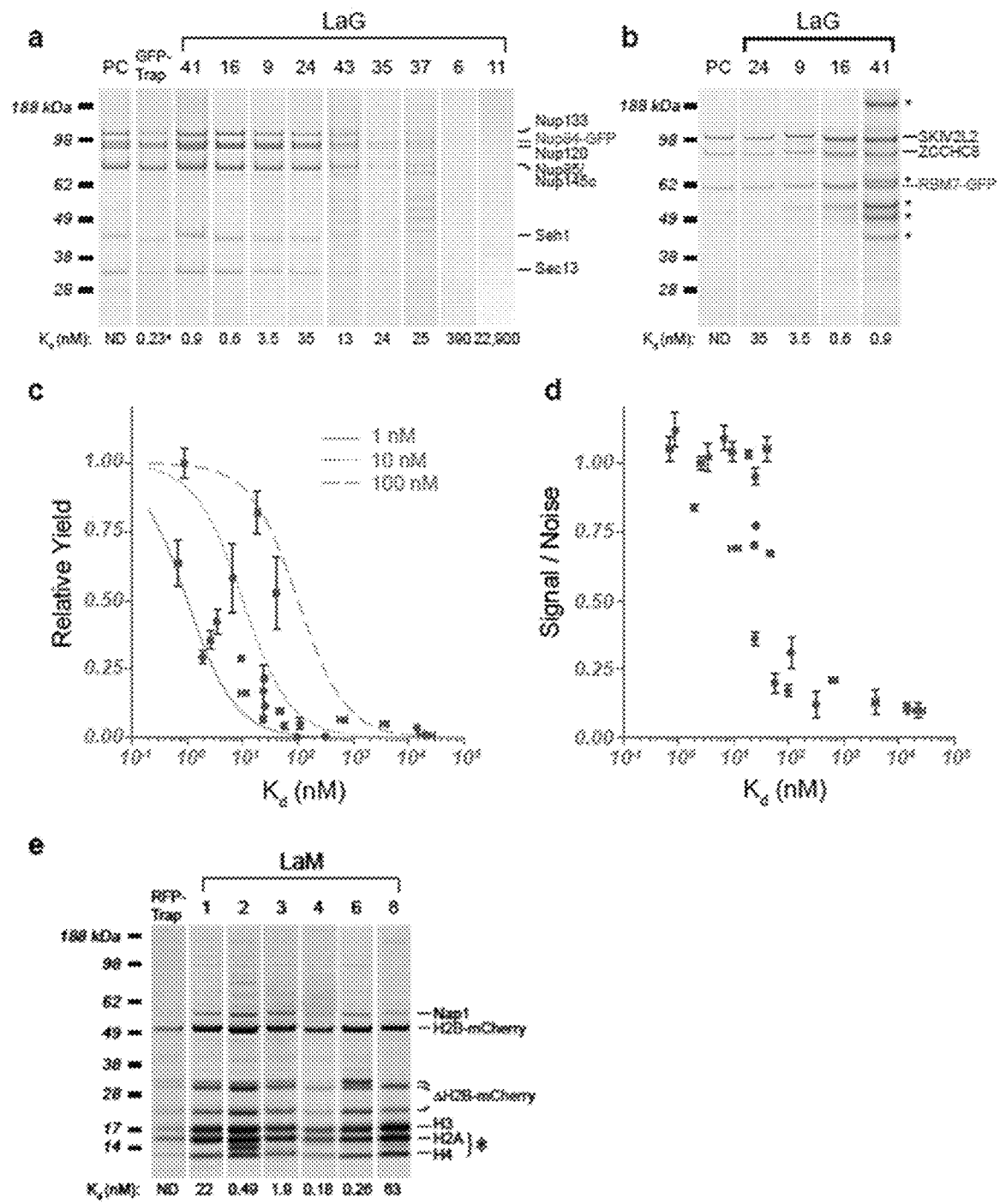
FIG. 3. GFP affinities and signal-to-noise range of recombinant LaG proteins. The numerically indicated LaGs, commercial GFP-Trap®, or polyclonal anti-GFP llama antibody (PC) were conjugated to magnetic Dynabeads, and used for affinity isolations of (a) S. cerevisiae Nup84-GFP or (b) RBM7-GFP from HeLa cells. Elutions were analyzed by SDS-PAGE, and duplicate Coomassie-stained bands identified by MS. Representative examples across a range of affinities are shown, and are labeled with the in vitro Kd for GFP as determined by SPR. (c) Relative yields of Nup84-GFP protein isolated from yeast affinity isolations using LaG-conjugated beads are plotted against the corresponding LaG's in vitro affinity for GFP (green circles). Theoretical curves of the expected fraction of ligand bound to an immobilized binding partner at various Kds are also shown, for three hypothetical ligand concentrations, covering the concentration range expected for typical cellular proteins in lysate (grey lines). (d) The relative signal to noise ratio of three known Nup84 complex components to a known contaminant region was similarly plotted against each LaG's Kd. (e) S. cerevisiae mCherry-HTB2 (histone H2B) was affinity isolated by LaMs or RFP-Trap® conjugated to magnetic Dynabeads. Elutions were analyzed by SDS-PAGE, and Coomassie-stained bands identified by MS. The asterisk indicates the location of LaM nanobody leakage from the Dynabeads. LaM lanes are labeled with the in vitro Kd for mCherry as determined by SPR.

We performed a variety of experiments to assess the utility of our nanobodies in affinity capture and subcellular localizations experiments. Thus, affinity capture experiments were performed on endogenous GFP- and mCherry-tagged proteins in yeast and human cells. All 25 positive GFP binders were used for the isolation of GFP-tagged Nup84, a structural nuclear pore complex component, in budding yeast (FIG. 3a)[29,30]. We plotted each LaG's observed $K_d$ against a quantification of either signal to background or yield from a Nup84-GFP affinity capture (FIGS. 3c and 3d, FIG. 6a). Almost all LaGs were able to pull down detectable amounts of Nup84-GFP and its associated proteins, and many performed as well or better than our best affinity-purified polyclonal antibodies. Similarly, while the single commercially available GFP-Trap® anti-GFP nanobody (ChromoTek GmbH) has a low reported $K_d$ of 0.59 nM[31], the performance of the highest-affinity LaGs, as judged by specificity and particularly yield in these pullouts, was comparable or in some cases better. Generally speaking though, a strong correlation is seen between low $K_d$ and both high signal to background and high yield. This correlation between yield and $K_d$ is broadly consistent with the relationship theoretically predicted for the percentage of a low abundance target bound in solution, when using hypothetical ligand concentrations estimated from typical abundances of yeast cellular proteins[32] (FIG. 3c). Our ability to compare structurally similar nanobodies raised against a single antigen provides a unique opportunity to demonstrate the importance of very low $K_d$ to high quality antibody performance in this type of application. Even nanobodies with $K_d$s around 10 nM, typically considered high affinity for an antibody, start displaying a precipitous decline in affinity purification performance. These findings highlight the importance of ultra-high affinity reagents, such as the nanobodies described here, for the high quality affinity captures required for proteomic and interactomic studies.

Affinity capture experiments were also performed on GFP-tagged Rbm7, a component of the human nuclear exosome, from HeLa cells (FIG. 3b)[4]. Many nanobodies demonstrated strong specificity for the targeted complex, comparable to performances seen with yeast-derived Nup84-GFP. However, differences in the amount of contaminants were seen for certain LaGs, notably LaG-41, from purifications in yeast versus HeLa cells (FIGS. 3a and 3b), despite high affinity for GFP ($K_d$=0.9 nM) and the efficient recovery of both tagged complexes. These results underscore how even high affinity reagents can give unpredictable background in certain cell types, demonstrating the utility of obtaining large repertoires of such affinity reagents so that at least one is likely to be optimal for any particular application. Similarly, Dynabead-conjugated LaMs were used to isolate mCherry-tagged histone H2B from yeast (FIG. 6e). For all six LaMs tested, the core nucleosome complex was efficiently isolated, demonstrating the affinity and specificity of this second group of nanobodies. Consistent with the low $K_d$s of all the identified LaMs, the yield and specificity of all affinity isolations were similarly high. Commercial RFP-Trap® nanobody (ChromoTek GmbH) was also tested in this experiment, and the overall yields were substantially lower.

Figure 4:
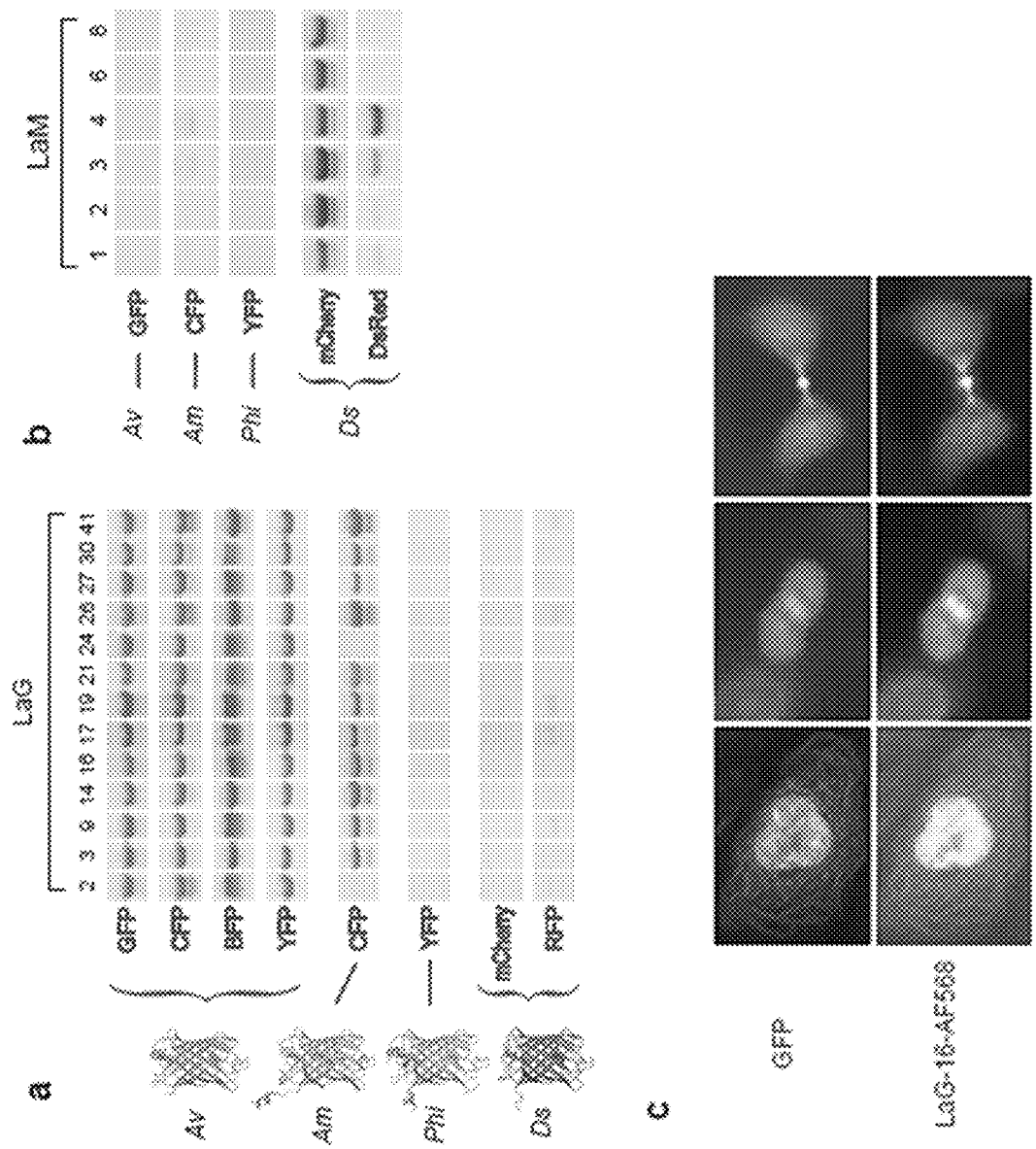
FIG. 4. Nanobody target specificity. (a) Thirteen high-affinity LaGs were conjugated to magnetic beads and incubated with various recombinant fluorescent proteins. All LaGs bound A. victoria (Av) GFP variants, while none bound mCherry or DsRed from Discosoma (Ds), or Phialidium (Phi) YFP. Mixed binding was observed for A. macrodactyla (Am) CFP. (b) Immobilized LaMs were similarly incubated with fluorescent proteins. All LaMs bound Discosoma mCherry, while none bound A. victoria GFP, A. macrodactyla CFP, or Phialidium YFP. Mixed binding was observed for DsRed. (c) An RPE1 cell line stably transfected with GFP-PRC1, a microtubule-associated protein, was stained with LaG16 conjugated to Alexa Fluor 568. Cells were visualized in the green (left) and red (right) channels. Representative cells from interphase (top), metaphase (middle), and telophase (bottom) were imaged.

To test their effectiveness in subcellular localizations, immunofluorescence microscopy was performed with a selection of the LaG repertoire. For a relatively low-abundance target protein with distinct subcellular distributions, we chose GFP-tagged PRC1, a protein associated with the nucleus and microtubules in interphase and the mitotic spindle in mitosis[33,34]. Tissue culture cells stably transfected with PRC1-GFP were fixed, and stained with a small subset of the lowest $K_d$ nanobodies conjugated to Alexa Fluor® 568. All gave similar specific localization, with a particularly strong signal from LaG-16 (FIG. 4c). This demonstrates that our nanobodies can prove effective in immunofluorescence microscopy, and it is thus likely that these reagents will prove useful in super-resolution microscopy studies[35]. We also compared the fluorescence spectra of GFP in the presence or absence of various LaGs to look for spectral shifts upon binding, as have previously been reported, and observed moderate increases in fluorescence for several LaGs, with a maximum increase in fluorescence intensity of approximately 60% (FIG. 15)[31].

One additional question of specificity we sought to address was the ability of our pool of nanobodies to recognize other fluorescent homologs of *Aequorea victoria* GFP and *Discosoma* mCherry. We tested the 13 highest affinity LaGs against a variety of fluorescent proteins: eGFP, two YFP variants, two CFP variants, BFP, mCherry, and DsRed (FIG. 4a). As expected, we found that none of these nanobodies bound DsRed or mCherry, two *Discosoma* sp.-derived proteins with low sequence identity to eGFP (<30%), or TurboYFP, derived from *Phialidium* sp., which has 53% sequence identity to eGFP[21,26,27]. All bound standard *Aequorea victoria*-derived CFP, YFP, and BFP variants (>96% eGFP identity). Interestingly, two LaGs did not bind a moderately divergent (78% eGFP identity) CFP sequence from *Aequorea macrodactyla*, while all others did[38]. These results indicate that while identified LaGs bind specifically to fluorescent proteins with high identity to eGFP, differential binding activities can be obtained through selection of variants from other species. As expected, our anti-mCherry LaM nanobodies bound to mCherry, but not to any form of GFP, YFP, or CFP tested (FIG. 4b). Interestingly, two LaMs (LaM-3 and LaM-4) bound to standard DsRed, from which mRFP1 and mCherry are derived. DsRed has approximately 80% sequence identity to mCherry, and is not recognized by the commercially available RFP-Trap® nanobody. Given the different fluorescent protein affinities observed with the LaG and LaM nanobodies, including specificity for AmCFP and DsRed, these reagents have diverse potential uses in differential labeling and affinity capture experiments from cells simultaneously expressing different fluorescently-tagged proteins.

Mapping of the Nanobody-Binding Epitopes on GFP

We identified the epitopes on GFP recognized by the twelve highest affinity LaGs using chemical shift perturbation, a well-established nuclear magnetic resonance (NMR) technique. This method allows the mapping of binding sites on a protein by following changes in its characteristic "fingerprint" spectrum (typically the $^{15}N^2H$ HSQC) occurring as a result of adding an unlabeled ligand into a $^{15}N$-labeled protein sample.

Figure 5:
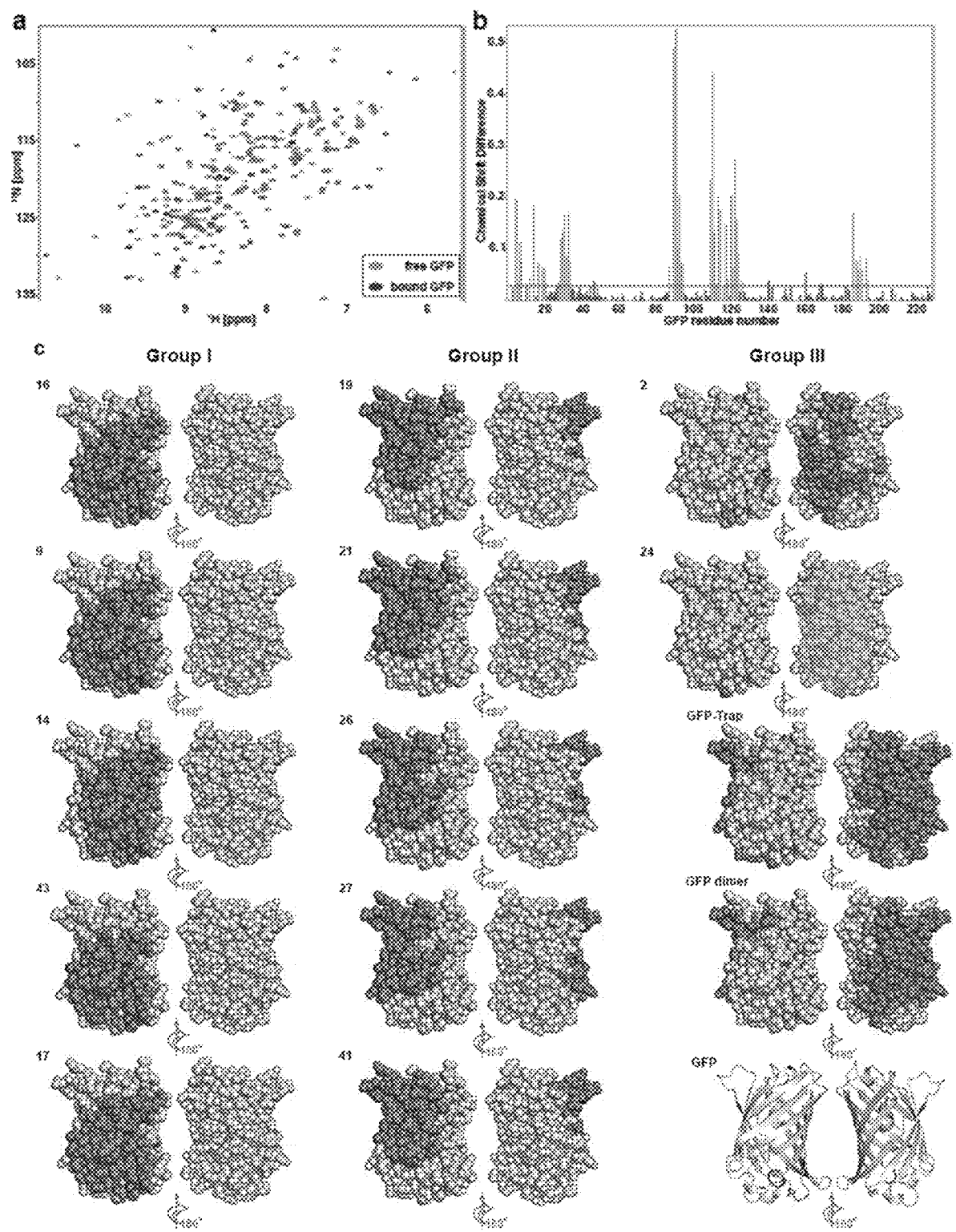
FIG. 5. Mapping of nanobody binding epitopes on GFP by NMR demonstrating that the nanobody repertoire produced has diverse epitope targets. (a) Overlay of 15N-1H HSQC spectra of 15N-labeled GFPuv alone (black) and in the presence of a 1:1 ratio LaG-16 (green). (b) A plot of the chemical shift difference of 15N-1H HSQC cross-peaks in the black (GFPuv alone) and the green (GFPuv in the presence of a 1:1 ratio LaG-16) spectra in (a) vs. GFPuv residue number. Residues with chemical shift difference >0.03 ppm (corresponding to the binding interface) are shown in green. (c) Binding epitopes of the 12 strongest binding nanobodies on GFPuv, shown in their respective epitope group type (groups I-III). For each nanobody, two opposite sides (via a 180° rotation along a vertical axis) of the GFPuv are shown, with the binding site of the respective nanobody colored green. All GFPuv molecules are presented in space-filling mode and have the same orientation in all panels. The 3 indented panels on the lowest right show the GFP-Trap® nanobody (top) binding epitope and dimerization site (middle) on GFPuv as well as its ribbon diagram depicting the secondary structure elements (bottom).
Figure 15:
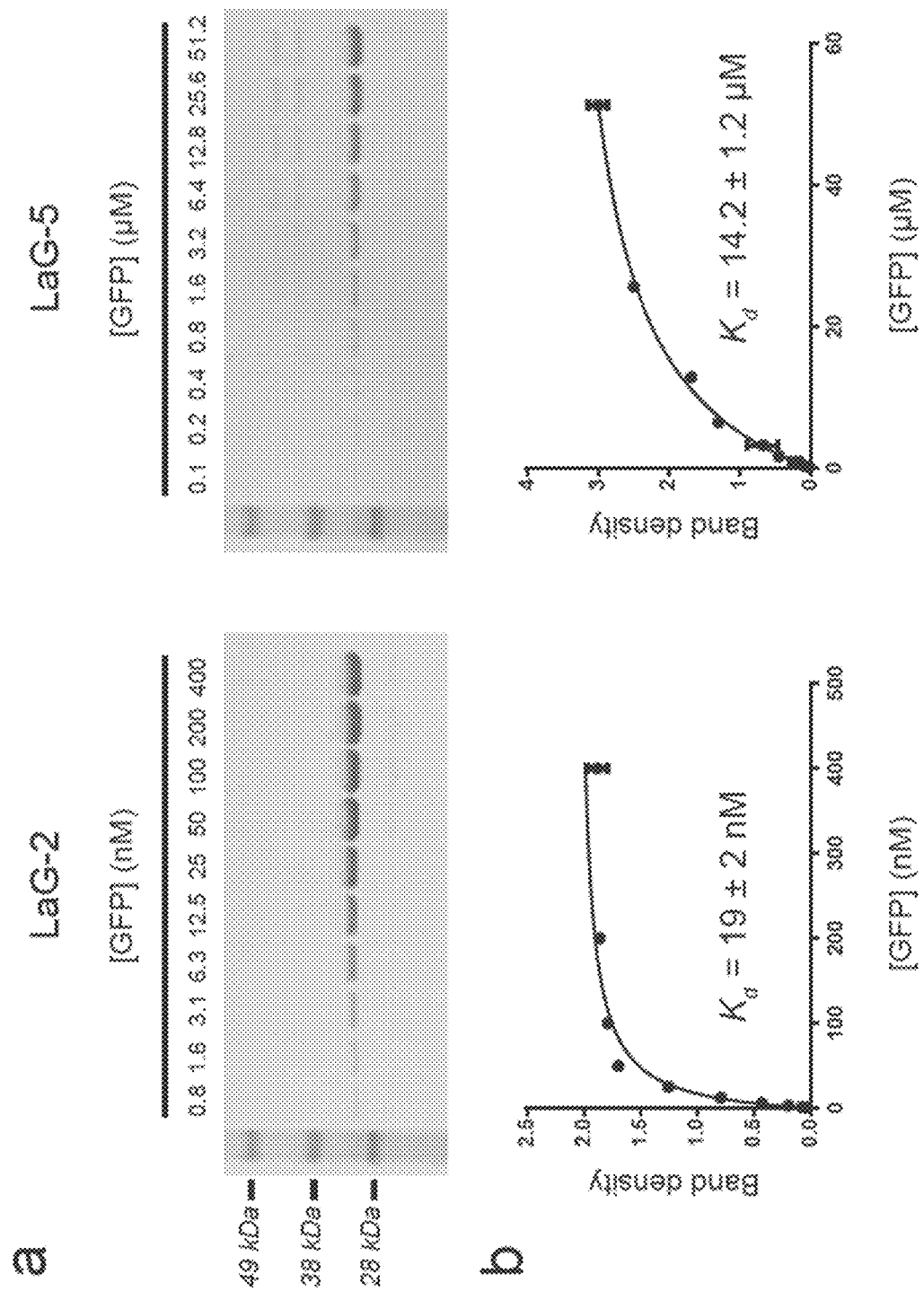
FIG. 15. $K_d$ determination by equilibrium bead binding. LaGs conjugated to magnetic Dynabeads were incubated with varying concentrations GFP. After incubation, beads were washed and bound protein was eluted with LDS. Elutions were run by SDS-PAGE and Coomassie stained (a). Band densities were quantified by ImageJ and plotted against concentrations, fit to equilibrium binding curves (b). Gel bands and plotted densities are shown for two representative LaGs.
Figure 16:
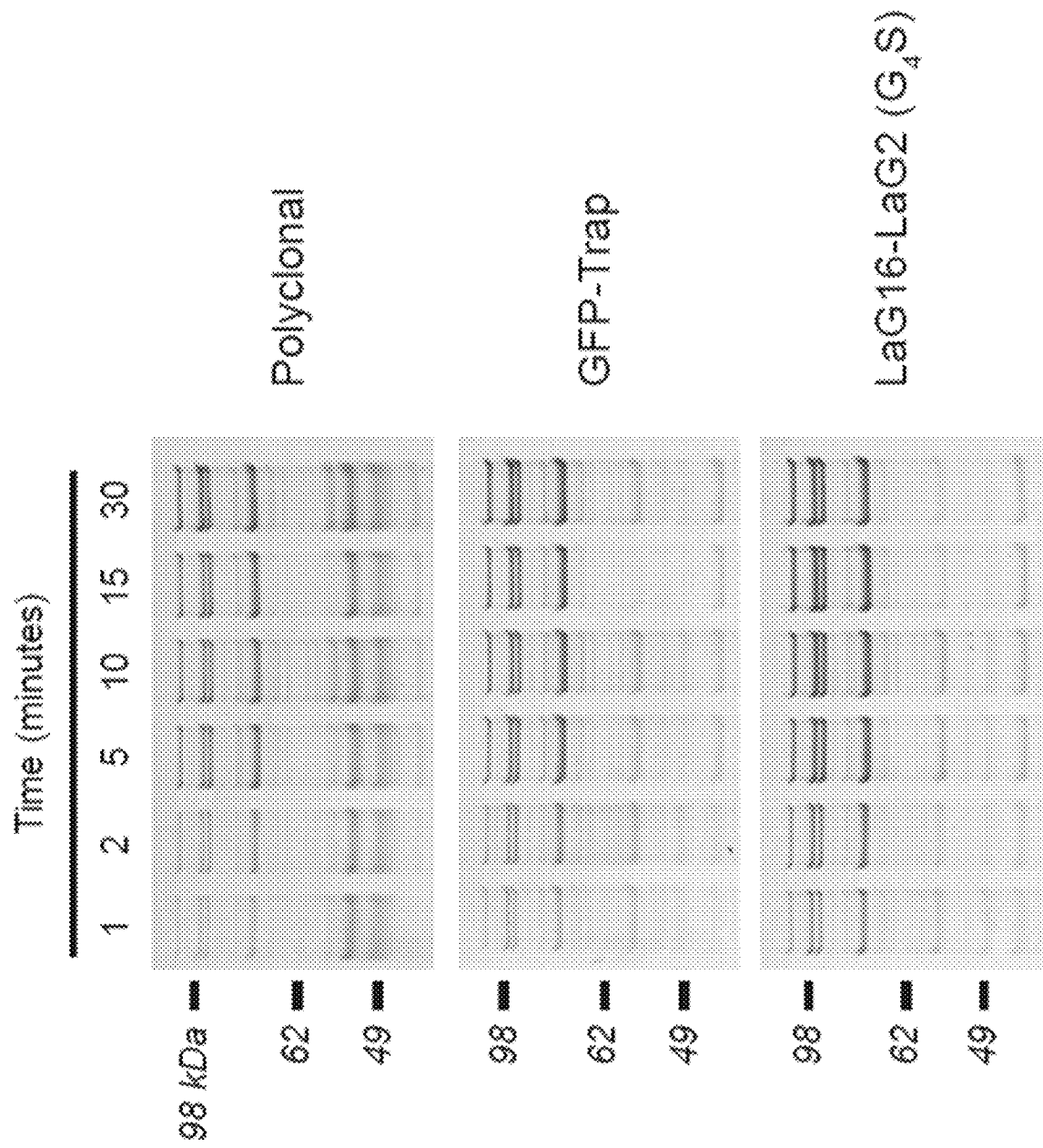
FIG. 16. Affinity isolations of yeast Nup84-GFP were performed using llama polyclonal anti-GFP, commercial GFP-Trap nanobody, or a LaG16-LaG2 dimer with a flexible glycine-rich linker ($G_4S$). The complex was isolated at various time points, elutions were analyzed by Coomassie staining after SDS-PAGE.

Because previous studies have already made backbone $^{15}N$-$^{1}H$ chemical shift assignments of the GFPuv variant[40,41] (closely related to standard eGFP with 97% sequence identity), we prepared $^{15}N$-labeled GFPuv, measured its $^{15}N$-$^{1}H$ HSQC spectrum and obtained the $^{15}N$-$^{1}H$ chemical shift assignments based on those published[40,41] (FIG. 15). We then prepared complexes between 12 high affinity LaGs and $^{15}N$-labeled GFPuv and measured their $^{15}N$-$^{1}H$ HSQC spectra. For 11 out of the 12 cases, we observed clear and specific changes in chemical shifts of a large percentage of cross-peaks compared to the $^{15}N$-$^{1}H$ HSQC spectrum of GFPuv alone (FIG. 5a). In the 12$^{th}$ case, LaG-24, the nanobody did not bind the GFPuv variant. Therefore, we conclude that LaG-24 binds on the face of GFP containing residues S99, T153 and A163—those mutated to obtain GFPuv (FIG. 5c-LaG-24)[42]. This conclusion was supported by the chemical shift assignment we were able to obtain for eGFP (data not shown).

A chemical shift difference was calculated for all spectra, and residues exhibiting a difference higher than 0.03 ppm were judged to be in the binding interface (FIG. 5b)[39,43]. All the identified epitopes corresponded to large interfaces comprising more than 50 amino acids, consistent with the high affinity binding observed (FIG. 6a). The binding epitopes of the nanobodies can be divided into 3 distinct groups, with closely overlapping epitopes for all nanobodies in each group (FIG. 5c and FIG. 6a). The binding site of group I, containing 5 nanobodies (LaG-16, LaG-9, LaG-14, LaG-43 and LaG-17) overlaps with the binding site of group II, also containing 5 nanobodies (LaG-19, LaG-21, LaG-26, LaG-27 and LaG-41), whereas the two group III nanobodies (LaG-2 and LaG-24) exhibit a binding epitope on the opposite side of the GFP molecule compared to groups I and II. As a control, we also used this NMR approach to determine the GFPuv binding site of the commercial GFP-Trap® nanobody, the structure of whose complex with GFP has been crystallographically determined (PDB ID 3K1K)[44], and showed that the NMR-mapped epitope matched the published results[42,44]. Comparing the binding epitopes of our nanobodies with that of GFP-Trap®, group I shows virtually no overlap with the GFP-Trap® binding site, group II has some small overlap, while group III, which binds on the same face of GFP, shows significant overlap (FIG. 5c).

Dimerized LaGs as Ultra-High Affinity Reagents

As NMR identified multiple epitopes for these 12 LaGs, we engineered heterodimers of LaGs with non-overlapping binding sites on GFP that could potentially bind with higher affinity. Pairs of LaGs from different binding site groups were genetically fused with different peptide linkers and recombinantly expressed. A LaG16-LaG2 fusion with a flexible glycine-rich linker showed the highest affinity by SPR, with a $K_d$ of 36 pM, approximately twenty-fold lower than either LaG alone. Notably, the off-rate of these dimers from GFP, expected to be the major difference in such bivalent binders, decreased almost ten-fold. Dimers of other LaGs or with a different linker (a 3×FLAG tag), displayed $K_d$s in the range of 100-200 pM. We also sought to determine whether the higher affinity of these dimers could result in significantly faster affinity isolations after conjugation to magnetic beads, compared to single nanobodies or polyclonal anti-GFP. We therefore performed time courses of yeast Nup84-GFP isolations and compared the relative yields of known Nup84 complex components. The LaG16-LaG2 dimer showed notably higher yields at earlier time points, reaching approximately 90% of maximum yield after only 10 minutes, and 80% after 5 minutes (FIG. 6b). Thus, these picomolar affinity reagents open the door for increasingly rapid affinity isolations, potentially allowing the capture of weakly or transiently associated complex components for interactome studies. In addition, their high avidity would allow for the detection of low abundance or trace antigens, such as is required for many diagnostic applications.

It will be apparent from the foregoing that the present disclosure provides for the production and generation of nanobodies and allows for the rapid generation of a large antibody repertoire against multiple epitopes in a chosen antigen. Notably, this approach identifies nanobody sequences directly from the source, animal serum. This takes advantage of the complex, natural selection processes occurring in the animal's immune system, avoiding intermediary expression systems, which we couple with non-naturally occurring expression systems to provide recombinant antibodies, including the cell cultures comprising the expression vectors and the expression vectors themselves. Thus, the disclosure ultimately allows for the facile and low-cost production of a comprehensive set of specific high affinity nanobodies for use in the isolation and characterization of target macromolecules, such as the GFP-tagged proteins shown here. GFP is one of the most widely used protein tags across all biomedical disciplines, in applications ranging from visualization to proteomics. The enormous number of existing strains and prior research making use of GFP-tagged proteins means that our improved reagents for the affinity isolation of this tag will be of immediate general use. Given the ease and speed of our approach, it is well-suited to the development of new nanobody reagents against various types of protein targets; for example, we have expanded the GFP approach using mCherry as described further herein. In addition to commonly used protein tags, difficult to tag proteins will also be used as antigens to generate directly targeted nanobodies. For example, many categories of viral proteins have proven resistant to standard genetic tagging techniques, and are prime candidates for nanobody development, in applications from proteomics to therapeutics and diagnostics[45,46]. Indeed, the versatility and potential of nanobodies is huge, as reflected by the interest of the research community[10,19,46,47]. Nanobodies are much smaller than antibodies, resistant to aggregation, and can be readily humanized[19,48,49]. They have great potential in drug development, as they can bind with great specificity and efficacy to disease targets such as tumor cells, either independently (as a monomer or an ultra-high affinity nanobody dimer), or as a fusion with other protein domains, molecules, or drugs[50-53]. Nanobodies have proven extremely successful in trials as both potential cancer diagnostics and cancer therapeutics. As demonstrated here, the ability of the present methods to quickly and easily identify large repertoires of high affinity bacterially-expressed nanobodies against a chosen target antigen has the potential to significantly advance a field that can otherwise take years to generate such reagents.

REFERENCES FOR THE FOREGOING DESCRIPTION

1 Cristea, I. M., Williams, R., Chait, B. T. & Rout, M. P. Fluorescent proteins as proteomic probes. *Molecular & cellular proteomics: MCP* 4, 1933-1941, doi:10.1074/mcp.M500227-MCP200 (2005).
2 Rigaut, G. et al. A generic protein purification method for protein complex characterization and proteome exploration. *Nature biotechnology* 17, 1030-1032, doi:10.1038/13732 (1999).
3 Ho, Y. et al. Systematic identification of protein complexes in *Saccharomyces cerevisiae* by mass spectrometry. *Nature* 415, 180-183, doi:10.1038/415180a (2002).
4 Domanski, M. et al. Improved methodology for the affinity isolation of human protein complexes expressed at near endogenous levels. *Biotechniques* 0, 1-6, doi:10.2144/000113864 (2012).
5 Gingras, A. C., Aebersold, R. & Raught, B. Advances in protein complex analysis using mass spectrometry. *J Physiol* 563, 11-21, doi:10.1113/jphysiol.2004.080440 (2005).
6 Cortez-Retamozo, V. et al. Efficient cancer therapy with a nanobody-based conjugate. *Cancer Res* 64, 2853-2857 (2004).
7 Hamers-Casterman, C. et al. Naturally occurring antibodies devoid of light chains. *Nature* 363, 446-448, doi:10.1038/363446a0 (1993).
8 Muyldermans, S. Nanobodies: Natural Single-Domain Antibodies. *Annual Review of Biochemistry* 82, 775-797, doi:10.1146/annurev-biochem-063011-092449 (2013).
9 Harmsen, M. M. & De Haard, H. J. Properties, production, and applications of camelid single-domain antibody fragments. *Appl Microbiol Biotechnol* 77, 13-22, doi:10.1007/s00253-007-1142-2 (2007).
10 Romer, T., Leonhardt, H. & Rothbauer, U. Engineering antibodies and proteins for molecular in vivo imaging.

Curr Opin Biotechnol 22, 882-887, doi:10.1016/j.copbio.2011.06.007 (2011).

11 Dumoulin, M. et al. Single-domain antibody fragments with high conformational stability. Protein Sci 11, 500-515, doi:10.1110/ps.34602 (2002).

12 Arbabi Ghahroudi, M., Desmyter, A., Wyns, L., Hamers, R. & Muyldermans, S. Selection and identification of single domain antibody fragments from camel heavy-chain antibodies. FEBS letters 414, 521-526 (1997).

13 Arbabi-Ghahroudi, M., Tanha, J. & MacKenzie, R. Prokaryotic expression of antibodies. Cancer Metastasis Rev 24, 501-519, doi:10.1007/s10555-005-6193-1 (2005).

14 Rothbauer, U. et al. Targeting and tracing antigens in live cells with fluorescent nanobodies. Nat Methods 3, 887-889, doi:nmeth953 [pii] 10.1038/nmeth953 (2006).

15 Muyldermans, S. et al. Camelid immunoglobulins and nanobody technology. Vet Immunol Immunopathol 128, 178-183, doi:10.1016/j.vetimm.2008.10.299 (2009).

16 Bird, R. E. et al. Single-chain antigen-binding proteins. Science 242, 423-426 (1988).

17 Skerra, A. & Pluckthun, A. Assembly of a functional immunoglobulin Fv fragment in Escherichia coli. Science 240, 1038-1041 (1988).

18 Worn, A. & Pluckthun, A. Stability engineering of antibody single-chain Fv fragments. Journal of molecular biology 305, 989-1010, doi:10.1006/jmbi.2000.4265 (2001).

19 Muyldermans, S. Nanobodies: natural single-domain antibodies. Annu Rev Biochem, doi:10.1146/annurev-biochem-063011-092449 (2013).

20 Scheid, J. F. et al. Sequence and structural convergence of broad and potent HIV antibodies that mimic CD4 binding. Science 333, 1633-1637, doi:10.1126/science.1207227 (2011)

21 Shagin, D. A. et al. GFP-like proteins as ubiquitous metazoan superfamily: evolution of functional features and structural complexity. Mol Biol Evol 21, 841-850, doi:10.1093/molbev/msh079 (2004).

22 Dorner, T. & Radbruch, A. Antibodies and B cell memory in viral immunity. Immunity 27, 384-392, doi:10.1016/j.immuni.2007.09.002 (2007).

23 Benner, R., Hijmans, W. & Haaijman, J. J. The bone marrow: the major source of serum immunoglobulins, but still a neglected site of antibody formation. Clin Exp Immunol 46, 1-8 (1981).

24 Becker, R. S. & Knight, K. L. Somatic diversification of immunoglobulin heavy chain VDJ genes: evidence for somatic gene conversion in rabbits. Cell 63, 987-997 (1990).

25 Knight, K. L. Restricted VH gene usage and generation of antibody diversity in rabbit. Annu Rev Immunol 10, 593-616, doi:10.1146/annurev.iy.10.040192.003113 (1992).

26 Butler, J. E. Immunoglobulin gene organization and the mechanism of repertoire development. Scand J Immunol 45, 455-462 (1997).

27 Conrath, K. E. et al. Beta-lactamase inhibitors derived from single-domain antibody fragments elicited in the camelidae. Antimicrob Agents Chemother 45, 2807-2812, doi:10.1128/AAC.45.10.2807-2812.2001 (2001).

28 Alvarez-Rueda, N. et al. Generation of llama single-domain antibodies against methotrexate, a prototypical hapten. Mol Immunol 44, 1680-1690, doi:10.1016/j.molimm.2006.08.007 (2007).

29 Brohawn, S. G., Partridge, J. R., Whittle, J. R. & Schwartz, T. U. The nuclear pore complex has entered the atomic age. Structure 17, 1156-1168, doi:10.1016/j.str.2009.07.014 (2009).

30 Fernandez-Martinez, J. et al. Structure-function mapping of a heptameric module in the nuclear pore complex. The Journal of Cell Biology 196, 419-434, doi:10.1083/jcb.201109008 (2012).

31 Kirchhofer, A. et al. Modulation of protein properties in living cells using nanobodies. Nature structural & molecular biology 17, 133-138, doi:10.1038/nsmb.1727 (2010).

32 Ghaemmaghami, S. et al. Global analysis of protein expression in yeast. Nature 425, 737-741, doi:10.1038/nature02046 (2003).

33 Mollinari, C. et al. PRC1 is a microtubule binding and bundling protein essential to maintain the mitotic spindle midzone. The Journal of Cell Biology 157, 1175-1186, doi:10.1083/jcb.200111052 (2002).

34 Subramanian, R., Ti, S. C., Tan, L., Darst, S. A. & Kapoor, T. M. Marking and Measuring Single Microtubules by PRC1 and Kinesin-4. Cell 154, 377-390, doi: 10.1016/j.cell.2013.06.021 (2013).

35 Ries, J., Kaplan, C., Platonova, E., Eghlidi, H. & Ewers, H. A simple, versatile method for GFP-based super-resolution microscopy via nanobodies. Nature Methods 9, 582-584, doi:10.1038/nmeth.1991 (2012).

36 Matz, M. V. et al. Fluorescent proteins from nonbioluminescent Anthozoa species. Nature biotechnology 17, 969-973, doi:10.1038/13657 (1999).

37 Shu, X., Shaner, N. C., Yarbrough, C. A., Tsien, R. Y. & Remington, S. J. Novel chromophores and buried charges control color in mFruits. Biochemistry 45, 9639-9647, doi:10.1021/bi0607731 (2006).

38 Xia, N. S. et al. Bioluminescence of Aequorea macrodactyla, a common jellyfish species in the East China Sea. Mar Biotechnol (NY) 4, 155-162, doi:10.1007/s10126-001-0081-7 (2002).

39 Goldflam, M., Tarrago, T., Gairi, M. & Giralt, E. NMR studies of protein-ligand interactions. Methods in molecular biology 831, 233-259, doi:10.1007/978-1-61779-480-3_14 (2012).

40 Georgescu, J., Rehm, T., Wiehler, J., Steipe, B. & Holak, T. A. Backbone H(N), N, C(alpha) and C(beta) assignment of the GFPuv mutant. Journal of biomolecular NMR 25, 161-162 (2003).

41 Khan, F., Stott, K. & Jackson, S. 1H, 15N and 13C backbone assignment of the green fluorescent protein (GFP). Journal of biomolecular NMR 26, 281-282 (2003).

42 Battistutta, R., Negro, A. & Zanotti, G. Crystal structure and refolding properties of the mutant F99S/M153T/V163A of the green fluorescent protein. Proteins 41, 429-437 (2000).

43 Zuiderweg, E. R. Mapping protein-protein interactions in solution by NMR spectroscopy. Biochemistry 41, 1-7 (2002).

44 Kirchhofer, A. et al. Modulation of protein properties in living cells using nanobodies. Nature structural & molecular biology 17, 133-138, doi:10.1038/nsmb.1727 (2010).

45 Vanlandschoot, P. et al. Nanobodies(R): new ammunition to battle viruses. Antiviral Res 92, 389-407, doi:10.1016/j.antiviral.2011.09.002 (2011).

46 Huang, L., Muyldermans, S. & Saerens, D. Nanobodies (R): proficient tools in diagnostics. Expert Rev Mol Diagn 10, 777-785, doi:10.1586/erm.10.62 (2010).

47 Revets, H., De Baetselier, P. & Muyldermans, S. Nanobodies as novel agents for cancer therapy. *Expert Opin Biol Ther* 5, 111-124, doi:10.1517/14712598.5.1.111 (2005).
48 Vincke, C. et al. General strategy to humanize a camelid single-domain antibody and identification of a universal humanized nanobody scaffold. *J Biol Chem* 284, 3273-3284, doi:10.1074/jbc.M806889200 (2009).
49 Els Conrath, K., Lauwereys, M., Wyns, L. & Muyldermans, S. Camel single-domain antibodies as modular building units in bispecific and bivalent antibody constructs. *J Biol Chem* 276, 7346-7350, doi:10.1074/jbc.M007734200 (2001).
50 Jahnichen, S. et al. CXCR4 nanobodies (VHH-based single variable domains) potently inhibit chemotaxis and HIV-1 replication and mobilize stem cells. *Proc Natl Acad Sci USA* 107, 20565-20570, doi:10.1073/pnas.1012865107 (2010).
51 Roovers, R. C. et al. A biparatopic anti-EGFR nanobody efficiently inhibits solid tumour growth. *Int J Cancer* 129, 2013-2024, doi:10.1002/ijc.26145 (2011).
52 Ulrichts, H. et al. Antithrombotic drug candidate ALX-0081 shows superior preclinical efficacy and safety compared with currently marketed antiplatelet drugs. *Blood* 118, 757-765, doi:10.1182/blood-2010-11-317859 (2011).

The following materials and methods illustrate techniques used to obtain results described herein.

Isolation of V$_H$H Antibodies

Llamas were immunized with recombinant GFP-His$_6$, or recombinant mCherry-His$_6$ through a subcutaneous injection of 5 mg of protein with CFA. Three additional injections of 5 mg protein, with IFA, were performed at three week intervals. Serum bleeds were obtained 10 days after the final injection. 2.5 ml of serum was diluted ten-fold in 20 mM sodium phosphate, pH 7.0, and incubated with Protein G-agarose resin for 30 min. The flow-through was then incubated for 30 min with Protein A-agarose resin. Both resins were washed with 20 mM sodium phosphate, pH 7.0, and bound VHH IgG was eluted with 100 mM acetic acid, pH 4.0 and 500 mM NaCl (Protein G resin) or 100 mM acetic acid, pH 3.5 and 150 mM NaCl (Protein A resin). These elutions were pooled and dialyzed into PBS. 3 mg of this VHH fraction was then incubated with Sepharose-conjugated GFP. This resin was washed with 10 mM sodium phosphate, pH 7.4 and 500 mM NaCl, followed by 1-4.5 M MgCl$_2$ in 20 mM Tris, pH 7.5, and then equilibrated in PBS. The resin was then digested with 0.3 mg/ml papain in PBS plus 10 mM cysteine, for 4 hours at 37° C. The resin was then washed with 1) 10 mM sodium phosphate, pH 7.4 and 500 mM NaCl 2) PBS plus 0.1% Tween-20 3) PBS 4) 0.1 M NH$_4$OAc, 0.1 mM MgCl$_2$, 0.02% Tween-20. Bound protein was then eluted for 20 min with 0.1 M NH$_4$OH and 0.5 mM EDTA, pH 8.0. These elutions were dried down in a Speed-Vac and resuspended in LDS plus 25 mM DTT. The samples were alkylated with iodoacetamide and run on a 4-12% Bis-Tris gel. The ~15 kDa band corresponding to the digested VHH region was then cut out and prepared for MS.

RT-PCR and DNA Sequencing

Bone marrow aspirates were obtained from immunized llamas concurrent with serum bleeds. Bone marrow plasma cells were isolated on a Ficoll gradient using Ficoll-Paque (GE Healthcare). RNA was isolated from approximately 1-6×10$^7$ cells using Trizol LS reagent (Life Technologies), according to the manufacturer's instructions. cDNA was reverse-transcribed using Ambion RETROscript (Life Technologies). A nested PCR was then performed with IgG specific primers. In the first step, CALL001 (5'-GTCCTGGCTGCTCTTCTACAAGG-3') and CALL002 (5'-GGTACGTGCTGTTGA ACTGTTCC-3') primers were used to amplify the IgG variable domain into the CH2 domain. The approximately 600-750 bp band from VHH variants lacking a CH1 domain was purified on an agarose gel. Next, for 454 sequencing, VHH regions were specifically reamplified using framework 1- and 4-specific primers with 5' 454 adaptor sequences:

```
454-VHH-forward (5'-CGTATCGCCTCCCTCGCGCCATCAGATGGC

T[C/G]A[G/T]GTGCAGCTGGTGGAGTCTGG-3' (SEQ ID NO: 6)

and 454-VHH-reverse (5'- CTATGCGCCTTGCCAGCCCGCTCAG

GGAGACGGTGACCTGGGT-3' SEQ ID NO: 7))

(adaptor sequences are underlined)¹.
```

The approximately 400 bp product of this reaction was gel purified, then sequenced on a 454 GS FLX system after emPCR amplification, on one Pico Titer Plate. For Illumina MiSeq sequencing, the second PCR was instead performed with random 12-mers replacing adaptor sequences, to aid in cluster identification: MiSeq-VHH-forward (5'-ATGGCT[C/G]A[G/T]GTGCAGCTGGTGGAGTCTGG-3' SEQ ID NO:8)) and MiSeq-VHH-reverse (5'-GGA-GACGGTGACCTGGGT-3' SEQ ID NO:9)). The product of this PCR was gel purified, ligated to MiSeq adaptors before library preparation using Illumina kits, and run on a MiSeq sequencer with 2×300 bp paired end reads.

Database Preparation

The protein sequence databases used for identification were prepared by translating sequencing reads in all 6 reading frames, and for each read the longest Open Reading Frame (ORF) was selected. The selected ORF was digested with trypsin in silico and a list of unique tryptic peptides of 7 amino acids or longer was constructed and saved in a FASTA file. It is important to construct a FASTA file only containing unique peptides because even though most search engines can handle some sequence redundancy, they are not well equipped to handle the extreme redundancy that is provided by next generation sequencing of the single chain antibody locus and search engines either become very slow or crash if presented with such an extreme redundancy.

Mass Spectrometry

Gel sections containing V$_H$H domains were excised, reduced with DTT (100 μL; 10 mM DTT, 100 mM ammonium bicarbonate) at 56° C. for 30 min, and alkylated with iodoacetamide (100 μL; 55 mM iodoacetamide, 100 mM ammonium bicarbonate) at 25° C. for 20 min in the dark. The dehydrated gel slices were then subjected to in-gel digestion with proteomic-grade trypsin (80 μL; 25 ng trypsin, 25 mM ammonium bicarbonate) (Promega) at 37° C. overnight. The gel was extracted once with extraction solution (140 μL; 67% acetonitrile, 1.7% formic acid). The resulting proteolytic digest was cleaned with a STAGE tip[2] and loaded onto a home-packed reverse phase C18 column (75 μm I.D., 15 μm tip) (New Objective) with a pressurized bomb. The loaded peptides were subsequently separated with a linear gradient (0% to 42% acetonitrile, 0.5% acetic acid, 120 min, 150 nL/min after flow splitting) generated by an Agilent 1260 HPLC and directly sprayed into an LTQ-Velos-Orbitrap mass spectrometer (Thermo Scientific) for analysis. In the mass spectrometer, a survey scan was carried out in the orbitrap (resolution=30,000, AGC target=1E6) followed by tandem MS in the ion trap (AGC target=5E3) of the top twenty most intense peaks. Tandem MS was carried out with collision induced dissociation (isolation width=2 Th, CE=35%, activation time=5 ms). Internal calibration was used for improved mass accuracy (lock mass m/z=371.1012). In order to scan more peptides, both predictive AGC and dynamic exclusion were enabled (Repeat counts: 2, repeat duration: 12 s, exclusion duration: 60 s). Single and unassigned charge species were excluded from tandem MS scans. The raw files were converted into mzXML format with ReAdW (version 4.3.1).

MS-Based Identification of VHH Sequences

The MS search was performed on the custom database of tryptic peptides using the X! Tandem search engine. Then, the identified peptides filtered by expectation value were mapped to the sequences translated from 454 reads (longest ORF only, as described above). The CDR regions were located within the sequence based on approximate position in the sequence and the presence of specific leading and trailing amino acids. For example, to locate the CDR3 region, the algorithm searched for the left anchor YXC (X representing any amino acid) between position 93 and 103 of the sequence, and the right anchor WG between position n-14 and n-4 of the sequence, where n is the length of the sequence. Once the peptides were mapped to the sequences and their CDR regions, a metric was calculated to rank each sequence as a potential candidate based on the bioinformatics evidence available. The factors included in the metric were: MS coverage and length of individual CDR regions with CDR3 carrying highest weight, overall coverage including framework region, and a count of the 454 reads producing the sequence. Finally, sequences with similar CDR3 regions were grouped together, allowing for the identification of the highest confidence sequence corresponding to a particular CDR3. A sequence was assigned to a group where its hamming distance to an existing member was 1, i.e. there was one amino acid difference in the sequence, and different groups that have one shared sequence were further combined. By choosing sequence hits from different groups for production, we maximized the overall sequence diversity of the candidate pool. The candidate list was displayed for manual inspection as an interactive HTML page with CDR regions annotated, peptide mapping information and the ranking metrics shown for each sequence. All algorithms described above were implemented in Perl.

Web-based application for nanobody sequence identification: "Llama-Magic" The pipeline that was used for identification of the Nanobody sequences has been automated and is accessed through a web-based interface which allows upload of FASTA files containing reads from High-throughput DNA sequencing. Once uploaded, the reads will be automatically translated and digested to create an MS searchable database of tryptic peptides, as described above. Next, the MS (mgf) files can be uploaded for a selected tryptic peptide sequence database, and the parent and fragment error can be chosen for the X! Tandem search. Once the mgf files are uploaded, the X! Tandem search will be executed and the matching peptides saved. Then (1) annotation of CDR regions, (2) mapping of the identified peptides and (3) ranking and grouping of candidates are performed automatically, producing an interactive display of the candidate list showing detailed information regarding each sequence and its corresponding rank. Llama-Magic is implemented in Perl, HTML and JavaScript. Manual inspection was performed to make sure a) long CDR3 peptides, which embrace both variable regions and framework regions, have fragmentation pattern within the variable regions; b) CDR3 peptides are unique enough (uniqueness score <100);

Cloning

Nanobody sequences were codon-optimized for expression in *E. coli* and cloned into pCR2.1 after gene synthesis (Eurofins MWG Operon), incorporating BamHI and XhoI restriction sites at 5' and 3' ends, respectively. A pelB leader sequence was cloned into pET21b at NdeI and BamHI restriction sites using complementary primers: 5'-TATGAAATACTTATTGCCTACGGCAGCCGCTGGATTGTT-ATTACTCGCGGCCCAGC CGGCC ATGGCTG-3' (SEQ ID NO:42) and 5'-GATCCAGC-CATGGCCGGCTGGGCCGCGAGTAATAACAAT-CCAGCGGCTGCCGTA GGCAA-TAAGTATTTCA-3' 3' (SEQ ID NO:43). Nanobody sequences were then subcloned into pET21b-pelB using BamHI and XhoI restriction sites, with primers also encoding a PreScission Protease cleavage site just before the C-terminal 6×His tag.

Purification of Nanobodies pelB-fused nanobodies were expressed under a T7 promoter in Arctic Express (DE3) cells (Agilent), induced with IPTG at a final concentration of 0.1 mM. Cells were induced for 18-20 hours at 12° C., then pelleted by a 10 min spin at 5000×g. The periplasmic fraction was then isolated by osmotic shock[3]. This fraction was bound to His-Select nickel affinity resin (Sigma), washed with His wash buffer (20 mM sodium phosphate pH 8.0, 1 M NaCl, 20 mM imidazole), and eluted with His elution buffer (20 mM sodium phosphate pH 8.0, 0.5 M NaCl, 0.3 M imidazole). The elution was then dialyzed into PBS.

Fluorescent Protein Binding Assays

2 µg of fluorescent protein was added to 50 µl of 2 mg/ml *E. coli* lysate diluted in binding buffer (20 mM HEPES, pH 7.4, 350 mM NaCl, 0.01% Tween-20, 0.1 M PMSF, 3 µg/ml pepstatin A). This was incubated with 25 µl of nanobody-Dynabead slurry. After a 30 minute incubation at 4° C., beads were washed with binding buffer and bound protein was eluted with 15 µl LDS. Elutions were run on a 4-12% Bis-Tris gel.

$K_d$ Determinations

SPR measurements were obtained on a Proteon XPR36 Protein Interaction Array System (Bio-Rad). Recombinant GFP or mCherry was immobilized on a ProteOn GLC sensor chip: the chip surface was first activated with 50 mM sulfo-NHS and 50 mM EDC, run at a flow-rate of 30 µl/min for 300 sec. The ligand was then diluted to 5 µg/ml in 10 mM sodium acetate, pH 5.0, and injected at 25 µl/min for 180 sec. Finally, the surface was deactivated by running 1 M ethanolamine-HCl (pH 8.5) at 30 µl/min for 300 sec. This led to immobilization of approximately 600-800 response units (RU) of ligand. $K_d$s of recombinant nanobodies were determined by injecting 4 or 5 concentrations of each protein, in triplicate, with a running buffer of 20 mM HEPES, pH 8.0/150 mM NaCl/0.01% Tween. Proteins were injected at 50 µl/min for 120 sec, or 100 µl/min for 90 sec, followed by a dissociation time of 600 sec. Between injections, residual bound protein was eliminated by regeneration with 4.5 M $MgCl_2$ in 10 mM Tris, pH 7.5, run at 100 µl/min for 36 sec. Binding sensorgrams from these injections were processed and analyzed using the ProteOn Manager software. Binding curves were fit to the data with a Langmuir model, using grouped $k_a$, $k_d$, and $R_{max}$ values.

Cell Culture and Fluorescence Microscopy

A stable GFP-PRC1 cell line in hTERT-RPE1 cells was cultured on coverslips in DMEM/F-12 media with 10% FBS and penicillin/streptomycin at 37° C. with 8% $CO_2$ in a humidified environment[4]. For immunofluorescence microscopy, cells were fixed in ice-cold methanol for 10 minutes. After blocking for 30 min with 1% FBS in PBS, the cells were incubated for 1 hour at room temperature with recombinant nanobody conjugated to Alexa Fluor 568 succinimidyl ester (Life Technologies), diluted to 5 µg/ml in PBS/1% FBS. Cells were washed with PBS/1% FBS, then mounted with ProLong Gold (Life Technologies).

Affinity isolations of tagged protein complexes

Recombinant nanobodies were conjugated to epoxy-activated magnetic Dynabeads (Life Technologies), with minor modifications to published IgG coupling conditions[5]. 10 µg recombinant protein was used per 1 mg of Dynabeads, with conjugations carried out in 0.1 M sodium phosphate, pH 8.0 and 1 M ammonium sulfate, with an 18-20 hour incubation at 30° C. Affinity isolations of yeast Nup84-GFP were carried out as previously described, using binding buffer consisting of 20 mM HEPES, pH 7.4, 500 mM NaCl, 2 mM $MgCl_2$, 0.1% CHAPS, 0.1M PMSF, and 3 µg/ml pepstatin A[5]. For each experiment, 50 µl of bead slurry was used with 0.5 g of yeast cells. Similar conditions were used for HTB2-mCherry isolations (from yeast with HTB2 genomically tagged at the C-terminus with mCherry[6]), except lysate was sonicated 4 times for 10 s before centrifugation, and the binding buffer consisted of 20 mM HEPES, pH 8.0, 300 mM NaCl, 110 mM KOAc, 0.1% Tween-20, 0.1% Triton X-100, 0.1M PMSF, and 3 µg/ml pepstatin A. Isolations of RBM7-LAP from HeLa cells were performed as previously described[7]. 10 µl of bead slurry was used with 100 mg of cells, using a binding buffer of 20 mM HEPES, pH 7.4, 300 mM NaCl, 0.5% Triton X-100, with cOmplete Protease Inhibitor, EDTA-free (Roche).

Fluorescence Spectra

Samples of recombinant GFP at 0.5 µM in PBS were mixed with either buffer or 10 µM of a LaG protein. Fluorescence spectra were obtained on a Synergy Neo (BioTek) microplate reader. Excitation spectra from 300 nm to 530 nm were taken at an emission wavelength of 560 nm, and emission spectra were measured from 450 nm to 600 nm at an excitation wavelength of 425 nm.

Phylogenetic Analysis

Phylogenetic trees and alignments were generated from LaG amino acid sequences using the Phylogeny.fr web service[8,9].

Mapping of Nanobody Binding Epitopes on GFP by NMR

Three variants of GFP were used in the preparation of NMR samples. GFP-His$_6$(eGFP), the variant used for immunization; GFPuv, the variant for which backbone $^{15}$N-$^1$H chemical shift assignments were available from BMRB file 5666[10] and a crystal structure was available from PBD ID 1B9C[11]; GFPuv_A206K (GFPuv_M), a monomeric version of GFPuv[12]. Table 1 summarizes the amino acid sequences of the three GFP variants. All NMR samples contained between 500 and 20 µM $^{15}$N-GFP either alone or in the presence of a 1-1.2 molar excess of LaG, 10 mM sodium phosphate buffer, pH 7.4, 150 mM NaCl and 90% $H_2O$/10% $D_2O$. All NMR spectra (2D HSQC) were measured at 310K on a Bruker Avance DPX-600 MHz spectrometer equipped with a TCI cryoprobe. Backbone $^1$H-$^{15}$N assignments of GFPuv were obtained from a comparison between a $^1$H-$^{15}$N HSQC spectrum of GFPuv alone and a simulated HSQC based on BMRB 5666[10]. Due to a very high similarity between the two, $^1$H-$^{15}$N backbone assignment of GFPuv was obtained for 97% of $^1$H-$^{15}$N backbone resonances for which assignment was available in BMRB5666. The accuracy of the GFPuv assignment was verified by mapping the binding site of a previously identified nanobody, GFP-Trap[13], on GFPuv. The crystal structure of the GFP/GFP-Trap complex is available in the PDB (PDB ID 3K1K)[13] and a comparison between the X-ray crystallography-derived binding site (obtained by analysis of 3K1K by PISA— 'Protein interfaces, surfaces and assemblies' service at the European Bioinformatics Institute (www.ebi.ac.uk/pdbe/prot_int/pistart.html)[14]) and the one determined by the chemical shift perturbation method, reveals they overlap, thereby confirming our assignment of GFPuv residues. Backbone $^1$H-$^{15}$N assignments of GFPuv_M were obtained from a comparison between a $^1$H-$^{15}$N HSQC spectrum of GFPuv and that of GFPuv_M. Assignment was verified by mapping the dimerization site of GFPuv and comparing it to the crystal structure of PBD ID 1B9C[11] (analyzed for interacting residues using PISA[14]).

All chemical shift differences were calculated using this formula:

$$CSD = \sqrt{\frac{\left(\frac{\Delta\delta N}{3}\right)^2 + \Delta\delta H^2}{2}}$$

where CSD is the total chemical shift difference and $\Delta\delta N$ and $\Delta\delta H$ are the chemical shift differences in the free and bound states between the amide nitrogens and protons, respectively. The CSD cutoff for binding site residues was 0.05 ppm for GFP-Trap binding site and for GFPuv dimerization site and 0.03 ppm for all LaG binding sites. All LaG binding site residues are listed in Table 2 and their respective $^1$H-$^{15}$N HSQC spectra are shown in overlaid with the $^1$H-$^{15}$N HSQC spectrum of the free GFPuv_M.

Tables

TABLE 1

Residues mutated in GFPuv vs. eGFP are marked in bold whereas residues mutated in GFPuv_M vs. GFPuv are marked in bold and italics ($A_{206}$ and $K_{206}$).

| | |
|---|---|
| wtGFP | MASKGEELFTGVVPILVELDGDVNGHKFSVSGEGEGDATY GKLTLKFICTTGKLPVPWPTLVTTFG$_{65}$YGVQCFA$_{72}$RYPD HMKQ$_{80}$HDFFKSAMPEGYVQERTIF$_{99}$FKDDGNYKTRAEVK FEGDTLVNRIELKGIDFKEDGNILGHKLEYNYNSHNVYI M$_{153}$ADKQKNGIKV$_{163}$NFKIRHNIEDGSVH$_{177}$LADHYQQNT PIGDGPVLLPDNHYLSTQSALSKDPNEKRDHMVLLEFVTA AGITHGMDELYKGLEVLFQGPSHHHHHH (SEQ ID NO: 1) |
| GFPuv | MSKGEELFTGVVPILVELDGDVNGHKFSVSGEGEGDATYG KLTLKFICTTGKLPVPWPTLVTTFS$_{65}$YGVQCFS$_{72}$RYPDH MKR$_{80}$HDFFKSAMPEGYVQERTIS$_{99}$FKDDGNYKTRAEVKFE GDTLVNRIELKGIDFKEDGNILGHKLEYNYNSHNVYIT$_{153}$ ADKQKNGIKA$_{163}$NFKIRHNIEDGSVQ$_{177}$LADHYQQNTPIGD GPVLLPDNHYLSTQS*A*$_{206}$LSKDPNEKRDHMVLLEFVTAAG ILEHHHHHH (SEQ ID NO: 2) |
| GFPuv_M | MSKGEELFTGVVPILVELDGDVNGHKFSVSGEGEGDATYG KLTLKFICTTGKLPVPWPTLVTTFSYGVQCFSRYPDHMKR HDFFKSAMPEGYVQERTISFKDDGNYKTRAEVKFEGDTLV NRIELKGIDFKEDGNILGHKLEYNYNSHNVYITADKQKNG IKANFKIRHNIEDGSVQLADHYQQNTPIGDGPVLLPDNHY LSTQS*K*$_{206}$LSKDPNEKRDHMVLLEFVTAAGILEHHHHHH (SEQ ID NO: 3) |

TABLE 2

Summary of binding site residues of the 12 strongest binding LaGs on GFPuv_M.

| | LaG | Binding epitope on GFPuv_M |
|---|---|---|
| Group I | 16 | 4-21; 28-34; 88-95; 110-127; 186-194 |
| | 9 | 3-21, 27-34, 86-95, 110-125, 186-194 |
| | 14 | 4-8, 12-22, 27-33, 84-97, 108-127, 186-194 |
| | 43 | 4-19, 30-35, 87-94, 110-125, 186-194 |
| | 17 | 4-20, 29-35, 87-95, 110-127, 186-194 |
| Group II | 19 | 12-19, 26-37, 42-51, 114-122, 207-221 |
| | 21 | 11-19, 26-36, 41-51, 114-123, 207-221 |
| | 26 | 10-15, 28-36, 41-51, 112-123, 210-224 |
| | 27 | 10-15, 28-51, 112-123, 210-224 |
| | 41 | 12-19, 27-36, 42-51, 113-122, 207-221 |
| Group III | 2 | 95-101, 135-140, 149-154, 162-176, 179-186, 194-202, 223-226 |
| | 24 | mutations in GFPuv: S72, N80, S99, T153, A163 |

The following references refer to the foregoing materials and methods:

1 Conrath, K. E. et al. Beta-lactamase inhibitors derived from single-domain antibody fragments elicited in the camelidae. *Antimicrob Agents Chemother* 45, 2807-2812, doi:10.1128/AAC.45.10.2807-2812.2001 (2001).

2 Rappsilber, J., Ishihama, Y. & Mann, M. Stop and go extraction tips for matrix-assisted laser desorption/ionization, nanoelectrospray, and LC/MS sample pretreatment in proteomics. *Anal Chem* 75, 663-670 (2003).

3 Skerra, A. & Pluckthun, A. Assembly of a functional immunoglobulin Fv fragment in *Escherichia coli*. *Science* 240, 1038-1041 (1988).

4 Subramanian, R., Ti, S. C., Tan, L., Darst, S. A. & Kapoor, T. M. Marking and Measuring Single Microtubules by PRC1 and Kinesin-4. *Cell* 154, 377-390, doi:10.1016/j.cell.2013.06.021 (2013).

5 Alber, F. et al. Determining the architectures of macromolecular assemblies. *Nature* 450, 683-694, doi:10.1038/nature06404 (2007).

6 Rout, M. P. et al. The yeast nuclear pore complex: composition, architecture, and transport mechanism. *The Journal of cell biology* 148, 635-651 (2000).

7 Domanski, M. et al. Improved methodology for the affinity isolation of human protein complexes expressed at near endogenous levels. *Biotechniques* 0, 1-6, doi:10.2144/000113864 (2012).

8 Dereeper, A., Audic, S., Claverie, J. M. & Blanc, G. BLAST-EXPLORER helps you building datasets for phylogenetic analysis. *BMC Evol Biol* 10, 8, doi:10.1186/1471-2148-10-8 (2010).

9 Dereeper, A. et al. Phylogeny.fr: robust phylogenetic analysis for the non-specialist. *Nucleic acids research* 36, W465-469, doi:10.1093/nar/gkn180 (2008).

10 Khan, F., Stott, K. & Jackson, S. 1H, 15N and 13C backbone assignment of the green fluorescent protein (GFP). *Journal of biomolecular NMR* 26, 281-282 (2003).

11 Battistutta, R., Negro, A. & Zanotti, G. Crystal structure and refolding properties of the mutant F99S/M153T/V163A of the green fluorescent protein. *Proteins* 41, 429-437 (2000).

12 Zacharias, D. A., Violin, J. D., Newton, A. C. & Tsien, R. Y. Partitioning of lipid-modified monomeric GFPs into membrane microdomains of live cells. *Science* 296, 913-916, doi:10.1126/science.1068539 (2002).

13 Kirchhofer, A. et al. Modulation of protein properties in living cells using nanobodies. *Nature structural & molecular biology* 17, 133-138, doi:10.1038/nsmb.1727 (2010).

14 Krissinel, E. & Henrick, K. Inference of macromolecular assemblies from crystalline state. *Journal of molecular biology* 372, 774-797, doi:10.1016/j.jmb.2007.05.022 (2007).

The following description provides an illustrative and non-limiting protocol for performing embodiments of this disclosure:

Camelid Immunizations (50-80 Days)

1) Prepare llama or alpaca animals for immunization with the purified antigen(s) of choice. 2) Immunize animals subcutaneously with a 1:1 mixture of Complete Freund's Adjuvant (CFA) and the antigen solution (0.1 to 5 mg of each antigen, depending on anticipated immunogenicity). 3) At 21 day intervals, administer three booster immunizations with a 1:1 mixture of Incomplete Freund's Adjuvant (IFA) and antigen (0.1 to 5 mg) (the number of booster immunizations can be varied). 4) 10 days after final booster, collect production serum bleeds (100 ml or more), and bone marrow aspirates (enough for 5 to 30 ml) from each animal.

Isolation of $V_HH$ IgG Fraction from Serum (1 Day)

5) Dilute 7.5 ml llama serum 1:9 with 67.5 ml 20 mM sodium phosphate, pH 7.0, filter with 0.22-µm filter 6) Add to 13 ml Protein G-agarose resin (Invitrogen 10-1243), equilibrated in 5 vol (65 ml) 20 mM sodium phosphate, pH 7.0. Incubate 30 min at room temperature on rotator. 7) Allow Protein G column to drain by gravity and collect flow-through. Then wash with 5 vol (65 ml) 20 mM sodium phosphate, pH 7.0. 8) Add Protein G flow-through to 13 ml Protein A-agarose resin (Invitrogen 10-1042), equilibrated in 5 vol (65 ml) 20 mM sodium phosphate, pH 7.0. Incubate 30 min at room temperature on rotator. 9) Collect flow-through from Protein A column. Wash with 5 vol (65 ml) 20 mM sodium phosphate, pH 7.0. 10) Elute from Protein G resin with 50 ml 100 mM acetic acid, pH 4.0/500 mM NaCl, and immediately neutralize with 5 ml 1 M Tris-HCl, pH 8.0. 11) Elute from Protein A resin with 50 ml 100 mM acetic acid, pH 3.5/150 mM NaCl, immediately neutralize with 5 ml 1 M Tris-HCl, pH 8.0. 12) Pool Protein A and Protein G elutions, and dialyze overnight into 4 L 1×PBS (4×1 L buffer changes, e.g. at 2, 2, 4, and 16 hr intervals) at 4° C. 13) Concentrate elutions to approximately 25 ml (typically 1-5 mg/ml), using 30 kDa MWCO Amicon Ultra-15 Centrifugal Filtration Units (Millipore), centrifuged at 5,000×g in a table-top centrifuge with swinging bucket rotor.

$V_HH$ IgG Affinity Purification (~2 Hrs) 14)

Conjugate antigen to Dynabeads M-270 epoxy (Life Technologies) according to manufacturer's instructions. Other types of magnetic beads, or CNBr-activated Sepharose can also be used. For Dynabeads, standard conditions for the conjugation use 10 µg of antigen per mg of beads, conjugated in 1 M ammonium sulfate and 0.1 M sodium phosphate, pH 8.0. After a 20-24 hr conjugation at 30° C., beads are washed with quick successive washes in 0.2 M glycine-HCl, pH 2.5, 10 mM Tris-HCl, pH 8.8, 100 mM triethylamine, and 1×PBS. This is followed by four 5 min washes with 1×PBS, a 5 min wash with 1×PBS+0.5% Triton, and a 15 min wash with 1×PBS+0.5% Triton. 15) Add 2-10 mg of VIM IgG to 25-50 mg Dynabeads (or ~100 ul of sepharose resin). Amounts can be scaled depending on size of antigen and strength of immune in an effort to obtain 1 µg or more of purified VHH. 16) Incubate 1 hr at room temperature on nutator. 17) Use a magnetic rack to collect beads, and remove VIM IgG solution. Wash beads 3× with 1 ml PBS.

Optional Papain Digest of Purified $V_HH$ IgG (1 Day) 18)

Resuspend beads in 100-300 µl papain digest solution by repeatedly pipetting—0.3 mg/ml papain (Sigma) in PBS/5 mM cysteine. 19) Incubate 4 hrs at 37° C., shaking at 1200 rpm on a Thermomixer. 20) Collect beads using a magnetic rack, and aspirate off the digest solution. 21) Wash twice with 1 ml PBS+0.1% Tween 22) Wash twice with 1 ml last wash buffer (0.1M NH$_4$OAc, pH 7.4/0.1 mM MgCl$_2$/0.02% Tween) 23) To elute, resuspend beads in 0.5 ml elution buffer (0.1M NH$_4$OH/10 mM EDTA, pH 8.0). Incubate 20 min at room temperature on rotator. 24) Collect elution from beads, repeat with an additional 0.5 ml. 25) Combine elutions and dry down in a Savant SpeedVac Concentrator 26) Resuspend samples in LDS loading buffer with 50 mM DTT, run on 4-12% Bis-Tris SDS-PAGE polyacrylamide gel (NuPAGE Novex, Life Technologies). Run at 200V for ~40 minutes with MES running buffer. 27) Fix and stain gels for 15 minutes in 0.5% Coomassie Brilliant Blue R-250/45% methanol/10% acetic acid. Destain in 16% methanol/10% acetic acid, changing destain solution three times after 15 minute incubations, or until fully destained.

Mass Spectrometry of VHH IgG (2 Days) 28)

Excise gel sections containing V$_H$H domains (at 14-30 kDa): Use an ophthalmic standard incision micro scalpel (FEATHER; PFM Medical) to cut the gel band into ~1 mm×1 mm pieces. Keep everything in a clean hood equipped with an air filter (e.g. AirClean 600) to avoid keratin contamination. 29) Destain the gel pieces in destaining solution (2×200 µL; 50% acetonitrile, 50 mM NH$_4$HCO$_3$) by shaking at 1500 rpm at 4° C. for 1 h. 30) Add pure acetonitrile (200 µL) to dehydrate the gel. The gel pieces should turn white. Dry the gel pieces in a Savant SpeedVac Concentrator. 31) Hydrate the dried gel pieces with 20 sequencing grade trypsin solution (12.5 ng/4 in 25 mM NH$_4$HCO$_3$; Promega). The gel pieces should turn transparent again. Cover the gel with an additional 60 µL of 25 mM NH$_4$HCO$_3$. Digest at 37° C. overnight, without shaking. 32) Remove and save the digestion solution in an Eppendorf tube at 4° C. Extract the gel pieces with extraction solution (2×70 µL 67% acetonitrile, 1.7% formic acid) by shaking at 4° C. for 1 h. The gel should shrink significantly. 33) Combine the digestion solution and extraction solution. Dry down to <50 µL in a SpeedVac Concentrator (it is essential to bring the organic content below 10%). 34) Clean the digest with a home-made C18 StageTip$_1$: Place the tip on the top of a 1.5 mL tube through an adaptor. Sequentially condition it with 50 µL methanol, 50 µL 70% acetonitrile+0.1% TFA, and 2×50 µL 0.1% TFA, by centrifugation at 2000 rpm for 1-2 min. 35) Load the digested peptides onto the tip and centrifuge at 2000 rpm for 5 min. Then wash 2× with 50 uL 0.5% acetic acid. Finally, sequentially elute with 50 µL 40% acetonitrile+0.5% acetic acid and 50 µL 80% acetonitrile+0.5% acetic acid. 36) Dry the eluate in a SpeedVac Concentrator. Resuspend the dried peptides by adding ~20 µL 0.5% acetic acid. Vortex the solution for 1 min then sonicate in a water sonication bath for 15 min. 37) Load ~⅓ of the solution on to a home-packed reverse phase C18 column (75 µm I.D., 15 µm tip, 5 cm resin) (New Objective) with a pressurized injection cell at 500 psi. 38) Connect the peptide-loaded C18 column to an HPLC system (e.g. Agilent 1200 series). Adjust the flow-rate through the column to ~150 nL/min with a flow splitter, and separate the peptides using a linear gradient (0% to 42% acetonitrile, 0.5% acetic acid, 120 min) directly sprayed into an LTQ-Velos-Orbitrap mass spectrometer (Thermo Scientific) for MS analysis. 39) The repetitive analytical cycle typically incorporates a high resolution mass scan in the Orbitrap (resolution=30K) followed by tandem MS scans in the ion trap of the 20 most intense peaks observed in each Orbitrap mass spectrum. Other settings of the mass spectrometer include: Spray voltage: 2-2.5 kV; Transfer capillary temperature: 275° C.; S-lens RF: 30% Dynamic exclusion time: 60 s; MS1 target: 1E6: MS1 maximum injection time: 500 ms; MS2 target: 5000; MS2 maximum injection time: 100 ms; Lock mass: m/z=371.1012; Preview mode: disabled; Charge species rejection: singly charged and unassigned; Minimum intensity for MS2: 1000; Isolation width: 2 Th; CID activation time: 5 ms; Normalized collision energy: 35%. 40) Analyze each sample three times to maximize the analysis depth. Convert all three instrument binary raw files from the same sample into a single MGF file by commonly used software (e.g. MM File Conversion), and upload to the a web server we designed.

Preparation of cDNA from Bone Marrow Aspirates (1 Day) 41)

Obtain bone marrow aspirates from immunized llamas, taken concurrently with serum bleeds. A 10-30 ml total volume is optimal. 42) Mix 9 parts RPMI 1640 medium plus 10% FBS with 1 part bone marrow aspirate. 43) In a 50 ml Falcon tube(s), overlay 1 part Ficoll-Paque (GE Healthcare) with 2 parts of the diluted aspirate. 44) Centrifuge Ficoll gradient (with brake deactivated) at 800×g for 40 minutes at room temperature (22° C.), in a table-top centrifuge with swinging bucket rotor. 45) Collect interface with lymphocytes and transfer to new tube. 46) Wash cells with 30 ml ice cold RPMI 1640 medium plus 10% FBS, and centrifuge at 300×g for 10 min at 4° C., in a table-top centrifuge with swinging bucket rotor. 47) Count cells with a hemocytometer, and resuspend in TRIzol (Life Technologies), using 1 ml per 1×10$_7$ cells. 48) Add 0.2 ml chloroform per 1 ml of TRIzol and shake tubes vigorously for 15 sec. 49) Incubate 3 minutes at room temperature. 50) Centrifuge 12,000×g in microcentrifuge for 15 min at 4° C. 51) Remove upper phase, transfer to new tube. 52) Add 5 glycogen, then 0.5 ml isopropanol per 1 ml TRIzol used. 53) Incubate 10 min at room temperature. 54) Centrifuge at 12,000×g for 10 min at 4° C. 55) Remove supernatant, and wash pellet with 1 ml 75% ethanol per 1 ml TRIzol used. 56) Vortex briefly, and centrifuge 7,500×g for 5 min at 4° C. 57) Air dry RNA, resuspend in nuclease-free H$_2$O. 58) Reverse transcribe RNA using Ambion RETROscript kit (Life Technologies): add 5 µg of RNA in 9 µl to 2 µl Oligo(dT). 59) Heat at 80° C. for 3 min. 60) Add 2 µl 10×RT buffer, 4 µl dNTP mix, 1 µl RNase inhibitor, and 1 µl MMLV-RT enzyme to reaction. 61) Incubate at 46° C. for 90 min. 62) Incubate at 92° C. for 10 min.

PCR Amplification and Sequencing of V$_H$H Sequences (1 Day) 63)

Perform the first step of a nested PCR with IgG specific primers CALL001 (5'-GTCCTGGCTGCTCTTCTA-CAAGG-3' (SEQ ID NO:4)) and CALL002 (5'-GGTACGTGCTGTTGA ACTGTTCC-3' (SEQ ID NO:5)): In a 100 µl volume with 1× ThermoPol reaction buffer, 2 mM MgSO$_4$, 0.2 mM dNTPs, and 0.5 µM CALL001 and CALL002 primers, combine 5 µL of the reverse transcription reaction and 2 µL of Deep Vent$_R$ polymerase. 64) After initial denaturation for 3 min at 94° C., amplify with 30 cycles: denature at 94° C. for 30 sec, anneal at 60° C. for 1 min, and extend at 72° C. for 50 sec. Run a final extension at 72° C. for 10 min. 65) Separate the PCR products by electrophoresis on a 1.2% agarose gel with TBE running buffer. Purify the approximately 600-750 bp band corresponding to VIM variant IgG. 66) With purified DNA as template, PCR amplify again using framework 1- and 4-specific primers. For 454 sequencing, adaptor sequences can be added: 454-VHH-forward (5'-CGTATCGCCTCCCTCGCGCCATCAG ATGGCT[C/G]A

[G/T]GTGCAGCTGGTGGAGTCTGG-3' (SEQ ID NO:6)) and 454-VHH-reverse (5'-CTATGCGCCTTGCCAGCCCGCTCAG GGA-GACGGTGACCTGGGT-3' (SEQ ID NO:7)) (adaptor sequences are underlined)$_2$. For Illumina MiSeq sequencing, a random 12-mer is added to aid cluster identification: MiSeq-VHH-forward (5'-ATGGCT[C/G]A[G/T]GTGCAGCTGGTGGAGTCTGG-3 (SEQ ID NO:8)') and MiSeq-VHH-reverse (5'-NNN GGA-GACGGTGACCTGGGT-3' (SEQ ID NO:9)). In a 100 µl volume with 1× ThermoPol reaction buffer, 2 mM MgSO$_4$, 0.2 mM dNTPs, and 0.5 µM of each primer, combine ~200 ng of purified product from the first PCR step and 2 µL of Deep Vent$_R$ polymerase. Repeat the PCR protocol from Step 64. 67) Separate the PCR product on an agarose gel as in Step 65, and gel purify the ~400 bp V$_H$H band. 68) For 454 sequencing, sequence PCR amplicon on a 454 GS FLX system after emPCR amplification, on one Pico Titer Plate. For MiSeq, ligate adaptors and generate library using Illumina kits, before sequencing with 2×300 bp paired end reads. 69) The high-throughput sequencing data is uploaded in FASTA form to the Llama Magic a web server we developed to generate candidate lists with MS data 70) The software will identify and rank candidate sequences according to sequence coverage and MS/sequencing abundance, so unique sequences can be selected from the top hits on this list.

Cloning and Screening Recombinant Nanobodies (~3-6 Days) 71)

Candidate sequences can be cloned by gene synthesis, after codon optimization for *E. coli*. For ease of cloning, in frame BamHI and XhoI restriction sites can be incorporated at 5' and 3' ends of the synthesized gene, respectively. 72) Subclone synthesized nanobody sequences into pET21b-pelB using BamHI and XhoI restriction sites. 73) To screen for expression and antigen binding, transform pET21b-pelB nanobody plasmids into Arctic Express (DE3) cells (Agilent) or BL21(DE3) cells. 74) Grow up 40 mL of transformed cells to OD ~0.7 and induce with IPTG at a final concentration of 0.1 mM. Induce for 18-20 hours at 12° C. (Arctic Express) or 18° C. (BL21(DE3)). 75) Harvest cells by spinning 10 min at 5,000×g at 4° C., remove media, and proceed directly to periplasmic purification. 76) Per 40 mL of original culture volume, resuspend pellet in 0.4 mL ice cold TES (0.2M Tris-HCl, pH 8.0, 0.5 mM EDTA, pH 8.0, 0.5 M sucrose). 77) Per 40 mL of original culture volume, add 0.6 ml of one part TES diluted with 4 parts ddH2O (ice cold). 78) Incubate on ice 30 min. 79) Centrifuge 30 min at 14,000 rpm in a microcentrifuge at 4° C. 80) Collect supernatants, add 110 µL of 10×TBT/NaCl (0.2 M HEPES, pH 7.4, 1.1 M potassium acetate, 20 mM MgCl$_2$, 1% Tween-20, 1.5 M NaCl). Save 10 µL for "Input" sample. Other buffers or salt strength can be substituted depending on desired binding affinity or application 81) Equilibrate 2.5 mg of Dynabeads conjugated to target antigen (above) with 1×TBT/NaCl (20 mM HEPES, pH 7.4, 110 mM potassium acetate, 2 mM MgCl$_2$, 0.1% Tween-20, 0.15 M NaCl). 82) Add supernatants to beads. Incubate for 1 hr, rotating at 4° C. 83) Collect beads on a magnetic rack, collect flow-through and wash 3× with 1 ml 1×TBT/NaCl. Save 10 µL of flow-through for "Flow-through" sample. 84) To elute, resuspend beads in 25 µL of 1×LDS (NuPAGE, Life Technologies). 85) Heat for 10 min at 75° C. Transfer LDS elution to new tube and add DTT to 50 mM. Heat for 10 min at 98° C. 86) Add 1×LDS/50 mM DTT to "Input" and "Flow-through" samples, and heat for 10 min at 98° C. 87) Run input, flow-through, and elution samples on 4-12% Bis-Tris gel (NuPAGE Novex, Life Technologies). Run at 200V for 40 min with MES running buffer. Stain in Coomassie blue (see Step 27), and select those nanobodies that express and bind well.

Large-Scale Purification of Recombinant Nanobodies (2 Days) 88)

Grow up 1-6 L of cells to OD ~0.7 and induce with IPTG at a final concentration of 0.1 mM. Induce for 18-20 hours at 12° C. (Arctic Express) or 18° C. (BL21(DE3)). 89) Harvest cells by spinning 10 min at 5,000×g at 4° C., remove media, and proceed directly to periplasmic purification. 90) Per 1 L of original culture volume, resuspend pellet in 10 ml ice cold TES (0.2 M Tris-HCl, pH 8.0, 0.5 mM EDTA, pH 8.0, 0.5 M sucrose). 91) Per 1 L of original culture volume, add 15 ml, ice cold, of one part TES diluted with 4 parts ddH2O (i.e. 3 ml TES plus 12 ml ddH2O). 92) Incubate on ice 30 min. 93) Spin 6000×g, 10 min at 4° C. 94) Take supernatant, spin 48,000×g, 15 min at 4° C. 95) Take supernatant, add 5 M NaCl to 0.15M. 96) Equilibrate Ni-NTA resin with 5 volumes binding buffer (20 mM Tris-HCl, pH 8.0, 0.15 M NaCl). 97) Incubate periplasmic sample with Ni-NTA resin for 30 min at 4° C. 98) Collect flow-through from column. 99) Wash with 6 column volumes Wash Buffer I (20 mM Tris-HCl, pH 8.0, 0.9 M NaCl). 100) Wash with 6 column volumes Wash Buffer II (20 mM Tris-HCl, pH 8.0, 0.15 M NaCl, 10 mM imidazole-HCl, pH 8.0). 101) Elute with 4 column volumes Elution Buffer (20 mM Tris-HCl, pH 8.0, 0.15 M NaCl, 250 mM imidazole-HCl, pH 8.0). 102) Assess elutions by SDS-PAGE, pool/concentrate as needed, and dialyze into desired buffer. Standard PBS-like buffers are suitable in most cases.

References for the immediately foregoing materials and methods:

1 Rappsilber, J., Ishihama, Y. & Mann, M. Stop and go extraction tips for matrix-assisted laser desorption/ionization, nanoelectrospray, and LC/MS sample pretreatment in proteomics. *Anal Chem* 75, 663-670 (2003).
2 Conrath, K. E. et al. Beta-lactamase inhibitors derived from single-domain antibody fragments elicited in the camelidae. *Antimicrob Agents Chemother* 45, 2807-2812, doi:10.1128/AAC.45.10.2807-2812.2001 (2001).

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method of detecting a protein comprising green fluorescent protein (GFP) comprising contacting a sample containing or suspected of containing the GFP with a dimer comprising distinct two distinct heavy chain antibodies, comprising SEQ ID NO:21 (LaG-16) and SEQ ID NO:10 (LaG2), wherein the dimer comprises a glycine-rich linker between the LaG-16 and LaG2, and detecting a complex of the dimer and the protein comprising the GFP.

2. The method of claim 1, wherein the glycine-rich linker comprises SEQ ID NO:44.

* * * * *